United States Patent
Guo et al.

(10) Patent No.: US 11,478,461 B2
(45) Date of Patent: Oct. 25, 2022

(54) [1.1.1] BICYCLO COMPOUNDS AS INDOLEAMINE 2,3-DIOXYGENASE INHIBITORS

(71) Applicant: Merck Sharp & Dohme Corp., Rahway, NJ (US)

(72) Inventors: Liangqin Guo, Monroe Township, NJ (US); Hongjun Zhang, Boston, MA (US); Ping Chen, Edison, NJ (US); Dane Clausen, Rahway, NJ (US); Xavier Fradera, Boston, MA (US); Yongxin Han, Needham, MA (US); Shuwen He, Fanwood, NJ (US); Xianhai Huang, Warren, NJ (US); Alexander Pasternak, Jamaica Plain, MA (US); Qinglin Pu, Needham, MA (US); Li Xiao, Cranbury, NJ (US); Feng Ye, Scotch Plains, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 17/047,247

(22) PCT Filed: Apr. 15, 2019

(86) PCT No.: PCT/US2019/027425
§ 371 (c)(1),
(2) Date: Oct. 13, 2020

(87) PCT Pub. No.: WO2019/204180
PCT Pub. Date: Oct. 24, 2019

(65) Prior Publication Data
US 2021/0393600 A1 Dec. 23, 2021

Related U.S. Application Data

(60) Provisional application No. 62/659,820, filed on Apr. 19, 2018.

(51) Int. Cl.
| | |
|---|---|
| A61K 31/44 | (2006.01) |
| A61K 45/06 | (2006.01) |
| C07C 237/22 | (2006.01) |
| C07C 255/60 | (2006.01) |
| C07D 213/75 | (2006.01) |

(Continued)

(52) U.S. Cl.
CPC ............ *A61K 31/44* (2013.01); *A61K 31/167* (2013.01); *A61K 31/17* (2013.01); *A61K 31/27* (2013.01); *A61K 31/337* (2013.01); *A61K 31/415* (2013.01); *A61K 31/42* (2013.01); *A61K 31/426* (2013.01); *A61K 31/4245* (2013.01); *A61K 31/437* (2013.01); *A61K 31/47* (2013.01); *A61K 31/472* (2013.01); *A61K 31/4965* (2013.01); *A61K 31/505* (2013.01); *A61K 45/06* (2013.01); *C07C 233/78* (2013.01); *C07C 233/79* (2013.01); *C07C 237/22* (2013.01); *C07C 255/60* (2013.01); *C07C 271/24* (2013.01); *C07C 271/36* (2013.01); *C07C 275/28* (2013.01); *C07C 275/30* (2013.01); *C07D 209/34* (2013.01); *C07D 213/75* (2013.01); *C07D 213/81* (2013.01); *C07D 215/48* (2013.01); *C07D 217/02* (2013.01); *C07D 217/26* (2013.01); *C07D 231/14* (2013.01); *C07D 237/28* (2013.01); *C07D 239/28* (2013.01); *C07D 239/42* (2013.01); *C07D 241/24* (2013.01); *C07D 261/08* (2013.01); *C07D 261/20* (2013.01);

(Continued)

(58) Field of Classification Search
None
See application file for complete search history.

(56) References Cited

U.S. PATENT DOCUMENTS

| | | |
|---|---|---|
| 2014/0275245 A1 | 9/2014 | Bunker |
| 2016/0075654 A1 | 3/2016 | Bunker et al. |

FOREIGN PATENT DOCUMENTS

| | | |
|---|---|---|
| WO | 2017040606 A1 | 3/2017 |
| WO | 2017106062 A1 | 6/2017 |

(Continued)

OTHER PUBLICATIONS

Database CA [Online] Dec. 13, 2018 (Dec. 13, 2018), Axten Jeffrey Michael: "Preparation of bicyclic bridged diamine derivatives as ATF4 pathway inhibitors for the treatment of diseases", XP55889515, retrieved from STN Database accession No. 170:95673 * the whole document *, (2 pages).

(Continued)

*Primary Examiner* — Kristin A Vajda
(74) *Attorney, Agent, or Firm* — Baerbel R. Brown; Catherine D. Fitch

(57) ABSTRACT

Disclosed herein are compounds of formula (I) which are inhibitors of an IDO enzyme: (I). Also disclosed herein are uses of the compounds in the potential treatment or prevention of an IDO-associated disease or disorder. Also disclosed herein are compositions comprising these compounds. Further disclosed herein are uses of the compositions in the potential treatment or prevention of an IDO-associated disease or disorder.

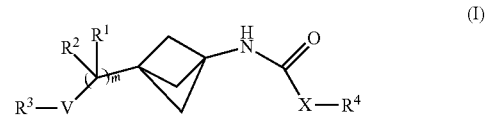

(I)

19 Claims, No Drawings

(51) Int. Cl.

| | |
|---|---|
| *C07C 271/36* | (2006.01) |
| *C07C 233/78* | (2006.01) |
| *C07C 271/24* | (2006.01) |
| *C07C 233/79* | (2006.01) |
| *C07D 213/81* | (2006.01) |
| *C07D 271/06* | (2006.01) |
| *C07D 239/28* | (2006.01) |
| *C07D 215/48* | (2006.01) |
| *C07C 275/30* | (2006.01) |
| *C07C 275/28* | (2006.01) |
| *C07D 239/42* | (2006.01) |
| *C07D 305/06* | (2006.01) |
| *C07D 261/08* | (2006.01) |
| *C07D 471/04* | (2006.01) |
| *C07D 261/20* | (2006.01) |
| *C07D 209/34* | (2006.01) |
| *C07D 277/56* | (2006.01) |
| *C07D 217/02* | (2006.01) |
| *C07D 231/14* | (2006.01) |
| *C07D 237/28* | (2006.01) |
| *C07D 241/24* | (2006.01) |
| *C07D 217/26* | (2006.01) |
| *A61K 31/167* | (2006.01) |
| *A61K 31/27* | (2006.01) |
| *A61K 31/4245* | (2006.01) |
| *A61K 31/47* | (2006.01) |
| *A61K 31/17* | (2006.01) |
| *A61K 31/505* | (2006.01) |
| *A61K 31/337* | (2006.01) |
| *A61K 31/437* | (2006.01) |
| *A61K 31/42* | (2006.01) |
| *A61K 31/426* | (2006.01) |
| *A61K 31/472* | (2006.01) |
| *A61K 31/415* | (2006.01) |
| *A61K 31/4965* | (2006.01) |

(52) U.S. Cl.
CPC ......... *C07D 271/06* (2013.01); *C07D 277/56* (2013.01); *C07D 305/06* (2013.01); *C07D 471/04* (2013.01)

(56) References Cited

FOREIGN PATENT DOCUMENTS

| | | | |
|---|---|---|---|
| WO | 2017157932 A1 | 9/2017 | |
| WO | WO-2017193063 A1 * | 11/2017 | ............... A61P 1/04 |
| WO | 2019090074 A1 | 5/2019 | |
| WO | 2019183589 A1 | 9/2019 | |

OTHER PUBLICATIONS

Database CA [Online] Aug. 16, 2018 (Aug. 16, 2018), Bacon Elizabeth M: "Pyrrolo[I,2-b]pyridazine derivatives as IRAK4 inhibitors and their preparation", XP55889500, Database accession No. 169:283570 * the whole document *, (2 pages).

Database CA [Online] May 9, 2019 (May 9, 2019), Martin Kathleen Ann: "Preparation of bicycloalkanecarboxamides and related compounds as modulators of the integrated stress pathway", XP55889486, retrieved from STN Database accession No. 170.596370 * the whole document * (3 pages).

Database CA [Online] Nov. 9, 2017 (Nov. 9, 2017), Sidrauski Camela: "Carboxamides as modulators of the integrated stress pathway and their preparation", XP55889480, retrieved from STN Database accession No. 167:552440 * the whole document *, (3 pages).

Kokhan, Serhii O. et al., Bicyclo[I.I.I]pentane-Derived Building Blocks for Click Chemistry, European Journal of Organic Chemistry, 2017, 6450-6456, 43.

* cited by examiner

[1.1.1] BICYCLO COMPOUNDS AS INDOLEAMINE 2,3-DIOXYGENASE INHIBITORS

CROSS REFERENCE TO RELATED APPLICATIONS

The present application is the 371 national phase application of International Application No. PCT/US2019/027425, filed Apr. 15, 2019, which claims the benefit of U.S. Provisional Application No. 62/659,820, filed Apr. 19, 2018, hereby incorporated by reference in its entirety.

BACKGROUND OF THE INVENTION

Tryptophan (Trp) is an essential amino acid required for the biosynthesis of proteins, niacin and the neurotransmitter 5-hydroxytryptamine (serotonin). The enzyme indoleamine 2,3-dioxygenase (IDO) catalyzes the first and rate limiting step in the degradation of L-tryptophan to N-formyl-kynurenine. In human cells, a depletion of Trp resulting from IDO activity is a prominent gamma interferon (IFN-γ)-inducible antimicrobial effector mechanism. IFN-γ stimulation induces activation of IDO, which leads to a depletion of Trp, thereby arresting the growth of Trp-dependent intracellular pathogens such as *Toxoplasma gondii* and *Chlamydia trachomatis*. IDO activity also has an antiproliferative effect on many tumor cells, and IDO induction has been observed in vivo during rejection of allogeneic tumors, indicating a possible role for this enzyme in the tumor rejection process (Daubener, et al, 1999, Adv. Exp. Med. Biol, 467: 517-24; Taylor, et al, 1991, FASEB J., 5: 2516-22).

It has been observed that HeLa cells co-cultured with peripheral blood lymphocytes (PBLs) acquire an immuno-inhibitory phenotype through up-regulation of IDO activity. A reduction in PBL proliferation upon treatment with interleukin-2 (IL2) was believed to result from IDO released by the tumor cells in response to IFN-γ secretion by the PBLs. This effect was reversed by treatment with 1-methyl-tryptophan (1-MT), a specific IDO inhibitor. It was proposed that IDO activity in tumor cells may serve to impair anti-tumor responses (Logan, et al, 2002, Immunology, 105: 478-87).

Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. For example, increased levels of IFNs and elevated levels of urinary Trp metabolites have been observed in autoimmune diseases; it has been postulated that systemic or local depletion of Trp occurring in autoimmune diseases may relate to the degeneration and wasting symptoms of these diseases. In support of this hypothesis, high levels of IDO were observed in cells isolated from the synovia of arthritic joints. IFNs are also elevated in human immunodeficiency virus (HIV) patients, and increasing IFN levels are associated with a worsening prognosis. Thus, it was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, Adv. Exp. Med. Biol, 294: 425-35). To this end, it has recently been shown that IDO inhibition can enhance the levels of virus-specific T cells and, concomitantly, reduce the number of virally-infected macrophages in a mouse model of HIV (Portula et al., 2005, Blood, 106: 2382-90).

IDO is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, Symp. Soc. Exp. Biol. 7: 320-38). Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to 1-MT, and a rapid, T cell-induced rejection of all allogeneic conception was observed. Thus, by catabolizing tryptophan, the mammalian conceptus appears to suppress T-cell activity and defends itself against rejection, and blocking tryptophan catabolism during murine pregnancy allows maternal T cells to provoke fetal allograft rejection (Moan, et al., 1998, Science, 281: 1191-3).

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003, Nature Med., 9: 1269-74). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Muller et al, 2005, Nature Med., 11: 312-9).

One mechanism contributing to immunologic unresponsiveness toward tumors may be presentation of tumor antigens by tolerogenic host APCs. A subset of human IDO-expressing antigen-presenting cells (APCs) that coexpressed CD 123 (IL3RA) and CCR6 and inhibited T-cell proliferation have also been described. Both mature and immature CD123-positive dendritic cells suppressed T-cell activity, and this IDO suppressive activity was blocked by 1-MT (Munn, et al, 2002, Science, 297: 1867-70). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs. Within the population of pDCs, the majority of the functional IDO-mediated suppressor activity segregated with a novel subset of pDCs coexpressing the B-lineage marker CD19. Thus, it was hypothesized that IDO-mediated suppression by pDCs in TDLNs creates a local microenvironment that is potently suppressive of host antitumor T cell responses (Munn, et al., 2004, J. Clin. Invest, 114(2): 280-90).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival. IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al, 2003, Trends Immunol, 24: 242-8). In states of persistent immune activation, availability of free serum Trp is diminished and, as a consequence of reduced serotonin production, serotonergic functions may also be affected (Wirleitner, et al., 2003, Curr. Med. Chem., 10: 1581-91).

In light of the experimental data indicating a role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression. [1.1.1] bicyclo compounds disclosed herein are useful in the potential treatment or prevention of IDO-related diseases.

SUMMARY OF THE INVENTION

Disclosed herein are novel [1.1.1] bicyclo compounds of formula (I) which are inhibitors of the IDO enzyme. Also disclosed herein are uses of these compounds in the potential treatment or prevention of an IDO-associated disease or disorder. Also disclosed herein are compositions comprising one or more of the compounds. Further disclosed herein are uses of these compositions in the potential prevention or treatment of an IDO-associated disease or disorder.

DETAILED DESCRIPTION OF THE INVENTION

Disclosed herein are compounds of formula (I), or a pharmaceutically acceptable salt thereof:

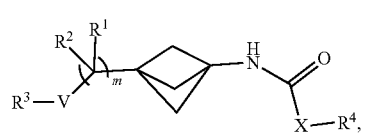

wherein:
m is 0 or 1;
V is selected from

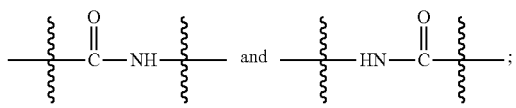

X is selected from a bond, O and $N(R^a)$; where $R^a$ is selected from hydrogen and $C_{1-6}$ alkyl; each occurrence of $R^1$ and $R^2$ is independently selected from:
  (i) hydrogen,
  (ii) $C_{1-6}$ alkyl, and
  (iii) $C_{3-6}$ cycloalkyl;
or alternatively, $R^1$ and $R^2$ together with the carbon to which they are attached form a $C_{3-6}$ cycloalkyl or a 4-6 membered heterocyclyl; wherein the $C_{3-6}$ cycloalkyl is optionally substituted with $C_{1-6}$ alkyl; and
each occurrence of $R^3$ and $R^4$ is independently selected from:
  (i) $C_{1-6}$ alkyl, optionally substituted with one to four substituents independently selected from halogen and phenyl,
  (ii) $C_{3-6}$ cycloalkyl,
  (iii) aryl, and
  (iv) heterocyclyl;
  wherein each of the phenyl of (i), aryl of (iii) and heterocyclyl of (iv) is optionally substituted with one to four substituents independently selected from:
    (a) halogen,
    (b) $C_{1-6}$ alkyl, optionally substituted with one to four halogens,
    (c) —O—$C_{1-6}$ alkyl, optionally substituted with one to four halogens,
    (d) $C_{3-6}$ cycloalkyl, optionally substituted with one to four halogens, and
    (e) —CN.

In one embodiment of formula (I), m is 0.
In one embodiment of formula (I), m is 1.
In one embodiment of formula (I), each occurrence of the aryl of $R^3$ and $R^4$ is independently selected from phenyl, naphthyl and bicyclo[4.2.0]octa-1,3,5-trienyl.
In one embodiment of formula (I), each occurrence of the aryl of $R^3$ and $R^4$ is independently selected from phenyl and naphthyl.
In one embodiment of formula (I), each occurrence of the aryl of $R^3$ and $R^4$ is phenyl.
In one embodiment of formula (I), each occurrence of the heterocyclyl of $R^3$ and $R^4$ is independently selected from furanyl, imidazolyl, isothiazolyl, isoxazolyl, oxadiazolyl, oxazolyl, pyranyl, pyrazinyl, pyrazolyl, pyridazinyl, pyridinyl, pyrimidinyl, pyrrolyl, tetrahydropyrazinyl, tetrahydropyridazinyl, tetrahydropyridinyl, tetrahydropyrimidinyl, tetrazolyl, thiadiazolyl, thiazolyl, thienyl, thiophenyl, triazolyl, imidazo[1,5-a]pyridinyl, indolinyl, indolizinyl, isoquinolinyl, pyrazolo[1,5-a]pyridinyl, quinolinyl, 4,5,6,7-tetrahydro-1,2-benzoxazolyl and triazolo[1,5-a]pyridinyl.
In one embodiment of formula (I), each occurrence of the heterocyclyl of $R^3$ and $R^4$ is independently selected from isoxazolyl, oxadiazolyl, pyrazinyl, pyrazolyl, pyridinyl, pyrimidinyl, thiazolyl, imidazo[1,5-a]pyridinyl, indolinyl, indolizinyl, isoquinolinyl, pyrazolo[1,5-a]pyridinyl, quinolinyl, 4,5,6,7-tetrahydro-1,2-benzoxazolyl and triazolo[1,5-a]pyridinyl.

In one embodiment of formula (I), one of the R³ and R⁴ is phenyl and the other is selected from phenyl, isoxazolyl, oxadiazolyl, pyrazinyl, pyrazolyl, pyridinyl, pyrimidinyl, thiazolyl, imidazo[1,5-a]pyridinyl, indolinyl, indolizinyl, isoquinolinyl, pyrazolo[1,5-a]pyridinyl, quinolinyl, 4,5,6,7-tetrahydro-1,2-benzoxazolyl and triazolo[1,5-a]pyridinyl.

In one embodiment of a compound of formula (I), the compound is of formula (Ia), or a pharmaceutically acceptable salt thereof:

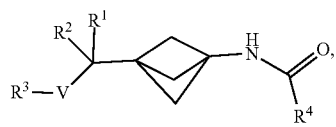

(Ia)

wherein each of V, R¹, R², R³ and R⁴ is as defined above for formula (I).

In one embodiment of a compound of formula (I), the compound is of formula (Ib), or a pharmaceutically acceptable salt thereof:

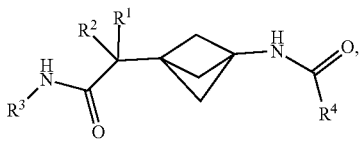

(Ib)

wherein each of R¹, R², R³ and R⁴ is as defined above for formula (I).

In one embodiment of a compound of formula (I), the compound is of formula (Ic), or a pharmaceutically acceptable salt thereof:

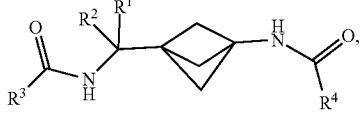

(Ic)

wherein each of R¹, R², R³ and R⁴ is as defined above for formula (I).

In one embodiment of a compound of formula (I), the compound is of formula (Id), or a pharmaceutically acceptable salt thereof:

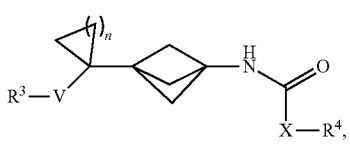

(Id)

wherein n is 1, 2 or 3; and each of V, X, R³ and R⁴ is as defined above for formula (I).

In one embodiment of a compound of formula (I), the compound is of formula (Ie), or a pharmaceutically acceptable salt thereof:

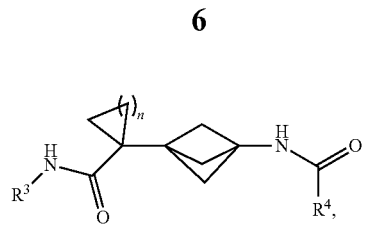

(Ie)

wherein n is 1, 2 or 3; and each of R³ and R⁴ is as defined above for formula (I).

In one embodiment of a compound of formula (I), the compound is of formula (If), or a pharmaceutically acceptable salt thereof:

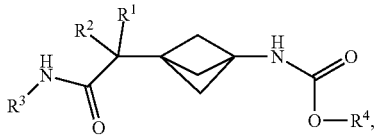

(If)

wherein:
n is 1, 2 or 3;
each of R¹, R² and R³ is as defined above for formula (I); and
R⁴ is selected from:
  (i) $C_{1-6}$ alkyl, optionally substituted with phenyl; and
  (ii) $C_{3-6}$ cycloalkyl.

In one embodiment of a compound of formula (I), the compound is of formula (Ig), or a pharmaceutically acceptable salt thereof:

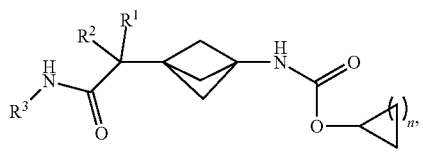

(Ig)

wherein:
n is 1, 2 or 3; and
each of R¹, R² and R³ is as defined above for formula (I).

In one embodiment of a compound of formula (I), the compound is of formula (Ih), or a pharmaceutically acceptable salt thereof:

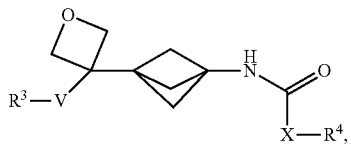

(Ih)

wherein:
each of V, X, R³ and R⁴ is as defined above for formula (I).

In one embodiment of a compound of formula (I), (Ia), (Ib), (Ic), (If) or (Ig): each occurrence of R¹ and R² is independently selected from:
  (i) hydrogen,
  (ii) $C_{1-6}$ alkyl, and
  (iii) $C_{3-6}$ cycloalkyl;
or alternatively, R¹ and R² together with the carbon to which they are attached form a $C_{3-6}$ cycloalkyl or a 4-6 membered saturated heterocyclyl; wherein the $C_{3-6}$ cycloalkyl is optionally substituted with $C_{1-6}$ alkyl.

In one embodiment of a compound of formula (I), (Ia), (Ib), (Ic), (If) or (Ig):
$R^1$ is hydrogen; and
$R^2$ is selected from:
(i) hydrogen, and
(ii) $C_{1-6}$ alkyl;
or alternatively, $R^1$ and $R^2$ together with the carbon to which they are attached form a $C_{3-6}$ cycloalkyl or oxetanyl; wherein the $C_{3-6}$ cycloalkyl is optionally substituted with methyl.

In one embodiment of a compound of formula (I), (Ia), (Ib), (Ic), (If) or (Ig):
$R^1$ is hydrogen; and
$R^2$ is methyl;
or alternatively, $R^1$ and $R^2$ together with the carbon to which they are attached form a $C_{3-6}$ cycloalkyl or oxetanyl.

In one embodiment of a compound of formula (I), (Ia), (Ib), (Ic), (Id), (Ie), (If), (Ig) or (Ih):
$R^3$ is selected from:
(i) phenyl,
(ii) naphthyl and
(iii) pyridinyl;
wherein each of the phenyl of (i), naphthyl of (ii) and pyridinyl of (iii) is optionally substituted with one to four substituents independently selected from:
(a) halogen, and
(b) $C_{1-6}$ alkyl.

In one embodiment of a compound of formula (I), (Ia), (Ib), (Ic), (Id), (Ie), (If), (Ig) or (Ih):
$R^3$ is selected from:
(i) phenyl, and
(ii) pyridinyl;
wherein each of the phenyl of (i) and pyridinyl of (ii) is optionally substituted with a halogen.

In one embodiment of a compound of formula (I), (Ia), (Ib), (Ic), (Id), (Ie), (If), (Ig) or (Ih):
$R^3$ is phenyl, optionally substituted with a halogen.

In one embodiment of a compound of formula (I), (Ia), (Ib), (Ic), (Id), (Ie) or (Ih): $R^4$ is selected from:
(i) phenyl,
(ii) naphthyl and
(iii) furanyl, imidazolyl, isothiazolyl, isoxazolyl, oxadiazolyl, oxazolyl, pyranyl, pyrazinyl, pyrazolyl, pyridazinyl, pyridinyl, pyrimidinyl, pyrrolyl, tetrahydropyrazinyl, tetrahydropyridazinyl, tetrahydropyridinyl, tetrahydro-pyrimidinyl, tetrazolyl, thiadiazolyl, thiazolyl, thienyl, thiophenyl, triazolyl, imidazo[1,5-a]pyridinyl, indolinyl, indolizinyl, isoquinolinyl, pyrazolo[1,5-a]pyridinyl, quinolinyl, 4,5,6,7-tetrahydro-1,2-benzoxazolyl and triazolo[1,5-a]pyridinyl;
wherein each of the phenyl of (i), naphthyl of (ii) and heterocyclyl of (iii) is optionally substituted with one to four substituents independently selected from:
(a) halogen, and
(b) $C_{1-6}$ alkyl, optionally substituted with one to four halogens,
(c) —O—$C_{1-6}$ alkyl, optionally substituted with one to four halogens,
(d) $C_{3-6}$ cycloalkyl, optionally substituted with one to four halogens, and
(e) —CN.

In one embodiment of a compound of formula (I), (Ia), (Ib), (Ic), (Id), (Ie) or (Ih): $R^4$ is selected from:
(i) phenyl,
(ii) naphthyl and
(iii) a heterocyclyl selected from isoxazolyl, oxadiazolyl, pyrazinyl, pyrazolyl, pyridinyl, pyrimidinyl, thiazolyl, imidazo[1,5-a]pyridinyl, indolinyl, indolizinyl, isoquinolinyl, pyrazolo[1,5-a]pyridinyl, quinolinyl, 4,5,6,7-tetrahydro-1,2-benzoxazolyl and triazolo[1,5-a]pyridinyl;
wherein each of the phenyl of (i), naphthyl of (ii) and heterocyclyl of (iii) is optionally substituted with one to three substituents independently selected from:
(a) halogen, and
(b) $C_{1-6}$ alkyl, optionally substituted with one to four halogens,
(c) —O—$C_{1-6}$ alkyl, optionally substituted with one to four halogens,
(d) $C_{3-6}$ cycloalkyl, optionally substituted with one to four halogens, and
(e) —CN.

In one embodiment of a compound of formula (I), (Ia), (Ib), (Ic), (Id), (Ie) or (Ih): $R^4$, when present, is selected from:
(i) phenyl, and
(ii) a heterocyclyl selected from isoxazolyl, oxadiazolyl, pyrazinyl, pyrazolyl, pyridinyl, pyrimidinyl, thiazolyl, imidazo[1,5-a]pyridinyl, indolinyl, indolizinyl, isoquinolinyl, pyrazolo[1,5-a]pyridinyl, quinolinyl, 4,5,6,7-tetrahydro-1,2-benzoxazolyl and triazolo[1,5-a]pyridinyl;
wherein each of the phenyl of (i) and heterocyclyl of (ii) is optionally substituted with one to three substituents independently selected from:
(a) halogen, and
(b) $C_{1-4}$ alkyl, optionally substituted with one to four halogens,
(c) —O—$C_{1-4}$ alkyl, optionally substituted with one to four halogens, and
(d) CN.

In one embodiment of a compound of formula (I), (Ia), (Ib), (Ic), (Id), (Ie), (If), (Ig) or (Ih):
each occurrence of $R^1$ and $R^2$, when present, is independently selected from:
(i) hydrogen,
(ii) $C_{1-6}$ alkyl, and
(iii) $C_{3-6}$ cycloalkyl;
or alternatively, when present, $R^1$ and $R^2$ together with the carbon to which they are attached form a $C_{3-6}$ cycloalkyl or a 4-6 membered heterocyclyl; wherein the $C_{3-6}$ cycloalkyl is optionally substituted with $C_{1-6}$ alkyl;
$R^3$ is selected from:
(i) phenyl,
(ii) naphthyl and
(iii) pyridinyl;
wherein each of the phenyl of (i), naphthyl of (ii) and pyridinyl of (iii) is optionally substituted with one to four substituents independently selected from:
(a) halogen, and
(b) $C_{1-6}$ alkyl; and
$R^4$, when present, is selected from:
(i) phenyl,
(ii) naphthyl and
(iii) a heterocyclyl selected from isoxazolyl, oxadiazolyl, pyrazinyl, pyrazolyl, pyridinyl, pyrimidinyl, thiazolyl, imidazo[1,5-a]pyridinyl, indolinyl, indolizinyl, isoquinolinyl, pyrazolo[1,5-a]pyridinyl, quinolinyl, 4,5,6,7-tetrahydro-1,2-benzoxazolyl and triazolo[1,5-a]pyridinyl;

wherein each of the phenyl of (i), naphthyl of (ii) and heterocyclyl of (iii) is optionally substituted with one to four substituents independently selected from:
  (a) halogen, and
  (b) $C_{1-6}$ alkyl, optionally substituted with one to four halogens,
  (c) —O—$C_{1-6}$ alkyl, optionally substituted with one to four halogens,
  (d) $C_{3-6}$ cycloalkyl, optionally substituted with one to four halogens, and
  (e) —CN.

In one embodiment of a compound of formula (I), (Ia), (Ib), (Ic), (Id), (Ie), (If), (Ig) or (Ih):
$R^1$, when present, is hydrogen;
$R^2$, when present, is selected from:
  (i) hydrogen, and
  (ii) $C_{1-6}$ alkyl;
or alternatively, when present, $R^1$ and $R^2$ together with the carbon to which they are attached form a $C_{3-6}$ cycloalkyl or a 4-6 membered saturated heterocyclyl; wherein the $C_{3-6}$ cycloalkyl is optionally substituted with $C_{1-6}$ alkyl;
$R^3$ is selected from:
  (i) phenyl, and
  (ii) pyridinyl;
  wherein each of the phenyl of (i) and pyridinyl of (ii) is optionally substituted with a halogen; and
$R^4$, when present, is selected from:
  (i) phenyl,
  (ii) naphthyl and
  (iii) a heterocyclyl selected from isoxazolyl, oxadiazolyl, pyrazinyl, pyrazolyl, pyridinyl, pyrimidinyl, thiazolyl, imidazo[1,5-a]pyridinyl, indolinyl, indolizinyl, isoquinolinyl, pyrazolo[1,5-a]pyridinyl, quinolinyl, 4,5,6,7-tetrahydro-1,2-benzoxazolyl and triazolo[1,5-a]pyridinyl;
  wherein each of the phenyl of (i), naphthyl of (ii) and heterocyclyl of (iii) is optionally substituted with one to four substituents independently selected from:
    (a) halogen, and
    (b) $C_{1-6}$ alkyl, optionally substituted with one to four halogens,
    (c) —O—$C_{1-6}$ alkyl, optionally substituted with one to four halogens, and
    (d) CN.

In one embodiment of a compound of formula (I), (Ia), (Ib), (Ic), (Id), (Ie), (If), (Ig) or (Ih):
$R^1$, when present, is hydrogen;
$R^2$, when present, is selected from:
  (i) hydrogen, and
  (ii) $C_{1-6}$ alkyl;
or alternatively, when present, $R^1$ and $R^2$ together with the carbon to which they are attached form a $C_{3-6}$ cycloalkyl or oxetanyl; wherein the $C_{3-6}$ cycloalkyl is optionally substituted with methyl;
$R^3$ is selected from:
  (i) phenyl, and
  (ii) pyridinyl;
  wherein each of the phenyl of (i) and pyridinyl of (ii) is optionally substituted with a halogen; and
$R^4$, when present, is selected from:
  (i) phenyl,
  (ii) naphthyl and
  (iii) a heterocyclyl selected from isoxazolyl, oxadiazolyl, pyrazinyl, pyrazolyl, pyridinyl, pyrimidinyl, thiazolyl, imidazo[1,5-a]pyridinyl, indolinyl, indolizinyl, isoquinolinyl, pyrazolo[1,5-a]pyridinyl, quinolinyl, 4,5,6,7-tetrahydro-1,2-benzoxazolyl and triazolo[1,5-a]pyridinyl;
  wherein each of the phenyl of (i), naphthyl of (ii) and heterocyclyl of (iii) is optionally substituted with one to four substituents independently selected from:
    (a) halogen, and
    (b) $C_{1-4}$ alkyl, optionally substituted with one to four halogens,
    (c) —O—$C_{1-4}$ alkyl, optionally substituted with one to four halogens, and
    (d) CN.

In one embodiment, the compound disclosed herein is selected from the group consisting of the compounds exemplified herein, for example, in Examples 1-154, or a pharmaceutically acceptable salt thereof.

Also disclosed herein is a pharmaceutical composition comprising a compound of formula (I), (Ia), (Ib), (Ic), (Id), (Ie), (If), (Ig) or (Ih), or a pharmaceutically acceptable salt thereof, and at least one pharmaceutically acceptable carrier.

Also disclosed herein is a method of inhibiting activity of indoleamine 2,3-dioxygenase (IDO) comprising contacting IDO with a compound of formula (I), (Ia), (Ib), (Ic), (Id), (Ie), (If), (Ig) or (Ih), or a pharmaceutically acceptable salt thereof.

Also disclosed herein is a method of inhibiting immunosuppression in a patient comprising administering to said patient an effective amount of a compound of formula (I), (Ia), (Ib), (Ic), (Id), (Ie), (If), (Ig) or (Ih), or a pharmaceutically acceptable salt thereof.

Also disclosed herein is a method of treating cancer, viral infection, depression, a neurodegenerative disorder, trauma, age-related cataracts, organ transplant rejection, or an autoimmune disease in a patient comprising administering to said patient an effective amount of a compound of formula (I), (Ia), (Ib), (Ic), (Id), (Ie), (If), (Ig) or (Ih), or a pharmaceutically acceptable salt thereof.

Also disclosed herein is a method of treating melanoma in a patient comprising administering to said patient an effective amount of a compound of formula (I), (Ia), (Ib), (Ic), (Id), (Ie), (If), (Ig) or (Ih), or a pharmaceutically acceptable salt thereof.

Further disclosed herein is a compound of formula (I), (Ia), (Ib), (Ic), (Id), (Ie), (If), (Ig) or (Ih), or a pharmaceutically acceptable salt thereof, for use in therapy. In one embodiment, disclosed herein is the use of a compound of formula (I), (Ia), (Ib), (Ic), (Id), (Ie), (If), (Ig) or (Ih), or a pharmaceutically acceptable salt thereof, for the preparation of a medicament for use in therapy.

As used herein, "alkyl" refers to both branched- and straight-chain saturated aliphatic hydrocarbon groups of 1 to 18 carbon atoms, or more specifically, 1 to 12 carbon atoms. Examples of such groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), sec-butyl (s-Bu), tert-butyl (t-Bu), isopentyl, and isohexyl. Alkyl groups may be optionally substituted with one or more substituents as defined herein. "$C_{1-6}$alkyl" refers to an alkyl group as defined herein having 1 to 6 carbon atoms.

"Aryl" refers to an aromatic monocyclic or multicyclic ring moiety comprising 6 to 14 ring carbon atoms, or more specifically, 6 to 10 ring carbon atoms. Monocyclic aryl rings include, but are not limited to, phenyl. Multicyclic rings include, but are not limited to, naphthyl and bicyclic rings wherein phenyl is fused to a $C_{5-7}$cycloalkyl or $C_{5-7}$cycloalkenyl ring. Aryl groups may be optionally substituted with one or more substituents as defined herein. Bonding can be through any of the carbon atoms of any ring.

"Cycloalkyl" refers to a monocyclic saturated carbocyclic ring having the specified number of carbon atoms. For example, $C_{3-6}$ cycloalkyl refers to a cycloalkyl group as defined herein having 3 to 6 carbon atoms. Examples of cycloalkyl include, but are not limited to, cyclopropyl, cyclobutyl, cyclopentyl, and cyclohexyl. Cycloalkyl groups may be optionally substituted with one or more substituents as defined herein.

"Halo" or "halogen" refers to fluoro, chloro, bromo or iodo, unless otherwise noted.

"Heterocycle" or "heterocyclyl" refers to a saturated, partially unsaturated or aromatic ring moiety having at least one ring heteroatom and at least one ring carbon atom. In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocyclic and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or aromatic. The heterocycle may be attached to the rest of the molecule via a ring carbon atom, a ring oxygen atom or a ring nitrogen atom. Non-limiting examples of heterocycles are described below.

In one embodiment, partially unsaturated and aromatic 4-7 membered monocyclic heterocyclyl moieties include, but are not limited to, 2,3-dihydro-1,4-dioxinyl, dihydrooxadiazolyl, dihydropyranyl, dihydropyrazinyl, dihydropyridazinyl, dihydropyridinyl, dihydropyrimidinyl, furanyl, imidazolyl, isothiazolyl, isoxazolyl, oxadiazolyl, oxazolyl, pyranyl, pyrazinyl, pyrazolyl, pyridazinyl, pyridinyl, pyrimidinyl, pyrrolyl, tetrahydropyrazinyl, tetrahydropyridazinyl, tetrahydropyridinyl, tetrahydropyrimidinyl, tetrazolyl, thiadiazolyl, thiazolyl, thienyl, thiophenyl, and triazolyl. In one embodiment, the heterocyclyl is selected from isoxazolyl, oxadiazolyl, pyrazinyl, pyrazolyl, pyridinyl, pyrimidinyl and thiazolyl.

In one embodiment, a heterocyclyl is a fused bicyclic ring moiety wherein a 4-6 membered heterocyclic ring comprising 1-4 heteroatoms selected from oxygen, sulfur and nitrogen and a 4-6 membered heterocyclic ring comprising 0-4 heteroatoms selected from oxygen, sulfur and nitrogen are connected through two atoms. Exemplary heterocycles of this type include, but are not limited to, azaindolyl, dihydronaphthyridinyl, imidazopyridinyl, indolinyl, indolizinyl, isoquinolinyl, naphthyridinyl, pteridinyl, purinyl, pyrazolo[1,5-a]pyridinyl, quinolinyl, quinolizinyl, tetrahydroindolizinyl, tetrahydronaphthyridinyl, tetrahydroquinolizinyl, 4,5,6,7-tetrahydro-1,2-benzoxazolyl and triazolo[1,5-a]pyridinyl. In one embodiment, the heterocyclyl is selected from imidazo[1,5-a]pyridinyl, indolinyl, indolizinyl, isoquinolinyl, pyrazolo[1,5-a]pyridinyl, quinolinyl, 4,5,6,7-tetrahydro-1,2-benzoxazolyl and triazolo[1,5-a]pyridinyl.

Such fused ring may be attached to the rest of the molecule via a carbon atom or a nitrogen atom on either ring. A heterocycle of this type includes a bicyclic ring comprising only one nitrogen as the sole heteroatom when the nitrogen is located at the bridgehead.

Heterocyclic groups may be optionally substituted with one or more substituents as defined herein.

"Optionally substituted" refers to "unsubstituted or substituted," and therefore, the generic structural formulas described herein encompass compounds containing the specified optional substituent(s) as well as compounds that do not contain the optional substituent(s). Each substituent is independently defined each time it occurs within the generic structural formula definitions.

Polymorphism

A compound of formula (I), (Ia), (Ib), (Ic), (Id), (Ie), (If), (Ig) or (Ih), including a salt or solvate thereof, may exist in crystalline form, non-crystalline form, or a mixture thereof. A compound or a salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound of formula (I), (Ia), (Ib), (Ic), (Id), (Ie), (If), (Ig) or (Ih).

Optical Isomers—Diastereomers—Geometric Isomers—Tautomers

Included herein are various isomers of the compounds of formula (I), (Ia), (Ib), (Ic), (Id), (Ie), (If), (Ig) or (Ih). The term "isomers" refers to compounds that have the same composition and molecular weight but differ in physical and/or chemical properties. The structural difference may be in constitution (geometric isomers) or in the ability to rotate the plane of polarized light (stereosiomers).

With regard to stereoisomers, a compound of formula (I), (Ia), (Ib), (Ic), (Id), (Ie), (If), (Ig) or (Ih) may have one or more asymmetric carbon atom and may occur as a racemic mixture or as individual enantiomers or diastereomers. All such isomeric forms are included herein, including mixtures thereof. If a compound of formula (I), (Ia), (Ib), (Ic), (Id), (Ie), (If), (Ig) or (Ih) contains a double bond, the substituent may be in the E or Z configuration. If a compound of formula (I), (Ia), (Ib), (Ic), (Id), (Ie), (If), (Ig) or (Ih) contains a disubstituted cycloalkyl, the cycloalkyl substituent may have a cis- or trans-configuration. All tautomeric forms are also intended to be included.

Any asymmetric atom (e.g., carbon) of a compound of formula (I), (Ia), (Ib), (Ic), (Id), (Ie), (If), (Ig) or (Ih) can be present in racemic mixture or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

A compound of formula (I), (Ia), (Ib), (Ic), (Id), (Ie), (If), (Ig) or (Ih) can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of the final compounds of the examples or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds can also be resolved by chiral chromatography, e.g., high pressure liquid chromatography (HPLC) using a chiral adsorbent.

Some of the compounds described herein may exist with different points of attachment of hydrogen, referred to as tautomers. For example, compounds including carbonyl —$CH_2C(O)$— groups (keto forms) may undergo tautomerism to form hydroxyl —$CH=C(OH)$— groups (enol forms). Both keto and enol forms, individually as well as mixtures thereof, are included within the scope of the present invention.

Isotopic Variations Compounds of formula (I), (Ia), (Ib), (Ic), (Id), (Ie), (If), (Ig) or (Ih) include unlabeled forms, as well as isotopically labeled forms. Isotopically labeled compounds have structures depicted by the formulas given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, sulfur, fluorine, iodine and chlorine, such as $^2H$ (i.e., Deuterium or "D"), $^3H$ $^{11}C$, $^{13}C$, $^{14}C$, $^{13}N$, $^{15}N$, $^{15}O$, $^{17}O$, $^{18}O$, $^{32}P$, $^{35}S$ $^{18}F$, $^{123}I$, $^{125}I$, and $^{36}Cl$. The invention includes $^3H$, $^{11}C$, $^{13}C$, $^{14}C$, $^{15}N$, $^{15}N$, $^{15}O$, $^{17}O$, $^{18}O$, $^{32}P$, $^{35}S$, $^{18}F$, $^{123}I$, $^{125}I$ and $^{36}Cl$. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, substitution with positron emitting isotopes, such as $^{11}C$, $^{18}F$, $^{15}O$ and $^{13}N$, may be particularly desirable for PET or SPECT studies.

Isotopically-labeled compounds of formula (I), (Ia), (Ib), (Ic), (Id), (Ie), (If), (Ig) or (Ih) can generally be prepared by conventional techniques known to those skilled in the art. Furthermore, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index.

Pharmaceutically Acceptable Salts

The term "pharmaceutically acceptable salt" refers to a salt prepared from a pharmaceutically acceptable non-toxic base or acid, including inorganic or organic base and inorganic or organic acid. Salts derived from inorganic bases include aluminum, ammonium, calcium, copper, ferric, ferrous, lithium, magnesium, manganic salts, manganous, potassium, sodium, zinc, and the like. Particular embodiments include ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound of formula (I), (Ia), (Ib), (Ic), (Id), (Ie), (If), (Ig) or (Ih) is basic, a salt may be prepared from a pharmaceutically acceptable non-toxic acid, including an inorganic and organic acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, trifluoroacetic acid (TFA) and the like. Particular embodiments include the citric, hydrobromic, hydrochloric, maleic, phosphoric, sulfuric, fumaric, tartaric and trifluoroacetic acids. It will be understood that, as used herein, references to the compounds disclosed herein are meant to also include pharmaceutically acceptable salts thereof.

Methods of Use

Compounds disclosed herein can inhibit activity of the enzyme indoleamine-2,3-dioxygenase (IDO). For example, the compounds disclosed herein can potentially be used to inhibit activity of IDO in cell or in an individual in need of modulation of the enzyme by administering an effective amount of a compound. Further disclosed herein are methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound or composition provided herein. Methods of measuring tryptophan levels and tryptophan degradation are routine in the art.

Also disclosed herein are methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, viral replication, etc.

Also disclosed herein are methods of treating diseases associated with activity or expression, including abnormal activity and/or overexpression, of IDO in an individual (e.g., patient) by administering to the individual in need of such treatment an effective amount or dose of a compound disclosed herein or a pharmaceutical composition thereof. Example diseases can include any disease, disorder or condition that may be directly or indirectly linked to expression or activity of the IDO enzyme, such as over expression or abnormal activity. An IDO-associated disease can also include any disease, disorder or condition that may be prevented, ameliorated, or cured by modulating enzyme activity. Examples of IDO-associated diseases include cancer, viral infection such as HIV and HCV, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosusor. Example cancers potentially treatable by the methods herein include cancer of the colon, pancreas, breast, prostate, lung, brain, ovary, cervix, testes, renal, head and neck, lymphoma, leukemia, melanoma, and the like. The compounds of the invention may also be useful in the treatment of obesity and ischemia. As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound disclosed herein includes the administration of a compound of the present invention to an individual or patient, such as a human, as well as, for example, introducing a compound of the invention into a sample containing a cellular or purified preparation containing the IDO enzyme.

A subject administered with a compound disclosed herein, or a pharmaceutically acceptable salt thereof, is generally a mammal, such as a human being, male or female. A subject also refers to cows, sheep, goats, horses, dogs, cats, rabbits, rats, mice, fish, and birds. In one embodiment, the subject is a human.

As used herein, the terms "treatment" and "treating" refer to all processes wherein there may be a slowing, interrupting, arresting, controlling, or stopping of the progression of a disease or disorder that may be associated with IDO enzyme activity. The terms do not necessarily indicate a total elimination of all disease or disorder symptoms. The terms also include the potential prophylactic therapy of the mentioned conditions, particularly in a subject that is predisposed to such disease or disorder.

The terms "administration of" and or "administering a" compound should be understood to include providing a compound described herein, or a pharmaceutically acceptable salt thereof, and compositions of the foregoing to a subject.

The amount of a compound administered to a subject is an amount sufficient to inhibit IDO enzyme activity in the subject. In an embodiment, the amount of a compound can be an "effective amount", wherein the subject compound is administered in an amount that will elicit a biological or medical response of a tissue, system, animal or human that is being sought by a researcher, veterinarian, medical doctor or other clinician. An effective amount does not necessarily include considerations of toxicity and safety related to the administration of a compound. It is recognized that one skilled in the art may affect physiological disorders associated with an IDO enzyme activity by treating a subject presently afflicted with the disorders, or by prophylactically treating a subject likely to be afflicted with the disorders, with an effective amount of a compound disclosed herein, or a pharmaceutically acceptable salt thereof.

An effective amount of a compound will vary with the particular compound chosen (e.g. considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen. Typical daily dosages for oral administration, to a human weighing approximately 70 kg would range from about 0.1 mg to about 2 grams, or more specifically, 0.1 mg to 500 mg, or even more specifically, 0.2 mg to 100 mg, of a compound of formula (I), (Ia), (Ib), (Ic), (Id), (Ie), (If), (Ig) or (Ih).

One embodiment of the present invention provides for a method of treating a disease or disorder associated with IDO enzyme activity comprising administration of an effective amount of a compound of formula (I), (Ia), (Ib), (Ic), (Id), (Ie), (If), (Ig) or (Ih) to a subject in need of treatment thereof. In one embodiment, the disease or disorder associated with an IDO enzyme is a cell proliferation disorder.

In one embodiment, disclosed herein is the use of a compound of formula (I), (Ia), (Ib), (Ic), (Id), (Ie), (If), (Ig) or (Ih) in a therapy. The compound may be useful in a method of inhibiting IDO enzyme activity in a subject, such as a mammal in need of such inhibition, comprising administering an effective amount of the compound to the subject.

In one embodiment, disclosed herein is a pharmaceutical composition comprising a compound of formula (I), (Ia), (Ib), (Ic), (Id), (Ie), (If), (Ig) or (Ih), or a pharmaceutically acceptable salt thereof, for use in potential treatment of a disorder or disease related to IDO enzyme activity.

Compositions

The term "composition" as used herein is intended to encompass a dosage form comprising a specified compound in a specified amount, as well as any dosage form which results, directly or indirectly, from combination of a specified compound in a specified amount. Such term is intended to encompass a dosage form comprising a compound of formula (I), (Ia), (Ib), (Ic), (Id), (Ie), (If), (Ig) or (Ih), or a pharmaceutically acceptable salt thereof, and one or more pharmaceutically acceptable carriers or excipients. Accordingly, the compositions of the present invention encompass any composition made by admixing a compound of the present invention and one or more pharmaceutically acceptable carrier or excipients. By "pharmaceutically acceptable" it is meant the carriers or excipients are compatible with the compound disclosed herein and with other ingredients of the composition.

In one embodiment, disclosed herein is a composition comprising a compound of formula (I), (Ia), (Ib), (Ic), (Id), (Ie), (If), (Ig) or (Ih), or a pharmaceutically acceptable salt thereof, and one or more pharmaceutically acceptable carriers or excipients. The composition may be prepared and packaged in bulk form wherein an effective amount of a compound of the invention can be extracted and then given to a subject, such as with powders or syrups. Alternatively, the composition may be prepared and packaged in unit dosage form wherein each physically discrete unit contains an effective amount of a compound of formula (I), (Ia), (Ib), (Ic), (Id), (Ie), (If), (Ig) or (Ih). When prepared in unit dosage form, the composition of the invention typically contains from about 0.1 mg to 2 grams, or more specifically, 0.1 mg to 500 mg, or even more specifically, 0.2 mg to 100 mg, of a compound of formula (I), (Ia), (Ib), (Ic), (Id), (Ie), (If), (Ig) or (Ih), or a pharmaceutically acceptable salt thereof.

A compound disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the invention are prepared using techniques and methods known to those skilled in the art. Some methods commonly used in the art are described in Remington's Pharmaceutical Sciences (Mack Publishing Company).

In one embodiment, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example polylactic acid, polepsilon caprolactone, polyhydroxy butyric acid, polyorthoesters, polyacetals, polydihydropyrans, polycyanacrylates and cross-linked or amphipathic block copolymers of hydrogels.

In one embodiment, the invention is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the invention in a suitably flavored aqueous solution; while elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the invention is directed to compositions for parenteral administration. Compositions adapted for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

A compound disclosed herein may be used in combination with one or more other active agents, including but not limited to, other anti-cancer agents, that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

When a compound disclosed herein is used contemporaneously with one or more other active agents, a composition containing such other active agents in addition to the compound disclosed herein is contemplated. Accordingly, the compositions of the present invention include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as a combined preparation include a composition comprising a compound of formula (I), (Ia), (Ib), (Ic), (Id), (Ie), (If), (Ig) or (Ih) and one or more other active agent(s) together in the same pharmaceutical composition, or a compound of formula (I), (Ia), (Ib), (Ic), (Id), (Ie), (If), (Ig) or (Ih) and one or more other therapeutic agent(s) in separate form, e.g. in the form of a kit.

The weight ratio of a compound disclosed herein to a second active agent may be varied and will depend upon the effective dose of each agent. Generally, an effective dose of each will be used. Thus, for example, when a compound disclosed herein is combined with another agent, the weight ratio of the compound disclosed herein to the other agent will generally range from about 1000:1 to about 1:1000, such as about 200:1 to about 1:200. Combinations of a compound disclosed herein and other active agents will generally also be within the aforementioned range, but in each case, an effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, the invention provides a composition comprising a compound of formula (I), (Ia), (Ib), (Ic), (Id), (Ie), (If), (Ig) or (Ih) and at least one other therapeutic agent as a combined preparation for simultaneous, separate or sequential use in therapy. In one embodiment, the therapy is the treatment of a disease or disorder associated with IDO enzyme activity.

In one embodiment, the invention provides a kit comprising two or more separate pharmaceutical compositions, at least one of which contains a compound of formula (I), (Ia), (Ib), (Ic), (Id), (Ie), (If), (Ig) or (Ih). In one embodiment, the kit comprises means for separately retaining said compositions, such as a container, divided bottle, or divided foil packet. An example of such a kit is a blister pack, as typically used for the packaging of tablets, capsules and the like.

A kit disclosed herein may be used for administering different dosage forms, for example, oral and parenteral, for administering the separate compositions at different dosage intervals, or for titrating the separate compositions against one another. To assist with compliance, a kit of the invention typically comprises directions for administration.

Disclosed herein is a use of a compound of formula (I), (Ia), (Ib), (Ic), (Id), (Ie), (If), (Ig) or (Ih) for treating a disease or disorder associated with IDO enzyme activity, wherein the medicament is prepared for administration with another active agent. The invention also provides the use of another active agent for treating a disease or disorder associated with an IDO enzyme, wherein the medicament is administered with a compound of formula (I), (Ia), (Ib), (Ic), (Id), (Ie), (If), (Ig) or (Ih).

The invention also provides the use of a compound of formula (I), (Ia), (Ib), (Ic), (Id), (Ie), (If), (Ig) or (Ih) for treating a disease or disorder associated with IDO enzyme activity, wherein the patient has previously (e.g. within 24 hours) been treated with another active agent. The invention also provides the use of another therapeutic agent for treating a disease or disorder associated with IDO enzyme activity, wherein the patient has previously (e.g. within 24 hours) been treated with a compound of formula (I), (Ia), (Ib), (Ic), (Id), (Ie), (If), (Ig) or (Ih). The second agent may be applied a week, several weeks, a month, or several months after the administration of a compound disclosed herein.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f] [1,2,4]triazin-6-yloxy)propan-2-yl)-2-aminopropanoate, also known as BMS-582664), motesanib (N-(2,3-dihydro-3,3-dimethyl-1H-indoi-6-yl)-2-[(4-pyridinyimethyj)amino]-3-pyfidinecarboxamide. and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX and MYLERAN), carboplatin (sold under the tradename PARAPLATIN), lomustine (also known as CCNU, sold under the tradename CeeNU), cisplatin (also known as CDDP, sold under the tradenames PLATINOL and PLATINOL-AQ), chlorambucil (sold under the tradename LEUKERAN), cyclophosphamide (sold under the tradenames CYTOXAN and NEOSAR), dacarbazine (also known as DTIC, DIC and imidazole carboxamide, sold under the tradename DTIC-DOME), altretamine (also known as hexamethylmelamine (HMM) sold under the tradename HEXALEN), ifosfamide (sold under the tradename IFEX), procarbazine (sold under the tradename MATULANE), mechlorethamine (also known as nitrogen mustard, mustine and mechloroethamine hydrochloride, sold under the tradename MUSTARGEN), streptozocin (sold under the tradename ZANOSAR), thiotepa (also known as thiophosphoamide, TESPA and TSPA, and sold under the tradename THIOPLEX).

Examples of anti-tumor antibiotics include, but are not limited to, doxorubicin (sold under the tradenames ADRIAMYCIN and RUBEX), bleomycin (sold under the tradename LENOXANE), daunorubicin (also known as dauorubicin hydrochloride, daunomycin, and rubidomycin hydrochloride, sold under the tradename CERUBIDINE), daunorubicin liposomal (daunorubicin citrate liposome, sold under the tradename DAUNOXOME), mitoxantrone (also known as DHAD, sold under the tradename NOVANTRONE), epirubicin (sold under the tradename ELLENCE), idarubicin (sold under the tradenames IDAMYCIN, IDAMYCIN PFS), and mitomycin C (sold under the tradename MUTAMYCIN).

Examples of anti-metabolites include, but are not limited to, claribine (2-chlorodeoxyadenosine, sold under the tradename LEUSTATIN), 5-fluorouracil (sold under the tradename ADRUCTL), 6-thioguanine (sold under the tradename PURINETHOL), pemetrexed (sold under the tradename ALIMTA), cytarabine (also known as arabinosylcytosine (Ara-C), sold under the tradename CYTOSAR-U), cytarabine liposomal (also known as Liposomal Ara-C, sold under the tradename DEPOCYT), decitabine (sold under the tradename DACOGEN), hydroxyurea (sold under the tradenames HYDREA, DROXIA and MYLOCEL), fludarabine (sold under the tradename FLUDARA), floxuridine (sold under the tradename FUDR), cladribine (also known as 2-chlorodeoxyadenosine (2-CdA) sold under the tradename LEUSTATIN), methotrexate (also known as amethopterin, methotrexate sodium (MTX), sold under the tradenames RHEUMATREX and TREXALL), and pentostatin (sold under the tradename NIPENT).

Examples of retinoids include, but are not limited to, alitretinoin (sold under the tradename PANRETIN), tretinoin (all-trans retinoic acid, also known as ATRA, sold under the tradename VESANOID), Isotretinoin (13-c/s-retinoic acid, sold under the tradenames ACCUTANE, AMNESTEEM, CLARAVIS, CLARUS, DECUTAN, ISOTANE, IZOTECH, ORATANE, ISOTRET, and SOTRET), and bexarotene (sold under the tradename TARGRETIN).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments. Examples of PD-1 antagonists include, but are not limited to, pembrolizumab (sold under the tradename KEYTRUDA) and nivolumab (sold under the tradename OPDIVO).

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename TRISENOX), asparaginase (also known as L-asparaginase, and *Erwinia* L-asparaginase, sold under the tradenames ELSPAR and KIDROLASE).

EXPERIMENTAL

The following examples are intended to be illustrative only and not limiting in any way. Abbreviations used are those conventional in the art or the following.
ACN acetonitrile
Boc tert-butyloxycarbonyl
Bu butyl
° C. degree Celsius
DCM dichloromethane
DEAD diethyl azodicarboxylate
DIEA diisopropylethylamine
DMA dimethylamine
DMAP 4-dimethylaminopyridine
DME dimethoxyethane
DMEA N,N-dimethylethylamine
DMF N,N-dimethylformamide
DMP dimethyl pimelimidate
DMSO dimethylsulfoxide
DPPA diphenylphosphoryl azide
EtOAc ethyl acetate
EtOH ethanol
g gram
h hour(s)
HATU (1-[Bis(dimethylamino)methylene]-1H-1,2,3-triazolo[4,5-b]pyridinium 3-oxide hexafluorophosphate)
HPLC high pressure liquid chromatography
kg kilogram
L liter
LAH lithium aluminium hydride
LC liquid chromatography
LC-MS, LCMS liquid chromatography and mass spectrometry
LDA lithium diisopropyl amide
MeOH methanol
MS mass spectrometry
MTBE methyl tert-butyl ether
min minutes
mL or ml milliliter(s)
m/z mass to charge ratio
nm nanometer
nM nanomolar
N normal
RT or rt room temperature
sat. saturated
TEA triethylamine
TFA trifluoroacetic acid
THF tetrahydrofuran
TMS trimethylsilyl
TMSOK potassium trimethylsilanolate
TosMIC toluenesulfonylmethyl isocyanide

GENERAL SYNTHETIC SCHEMES

The compounds of formula (I), (Ia), (Ib), (Ic), (Id), (Ie), (If), (Ig) or (Ih) may be prepared by methods known in the art of organic synthesis as set forth in part by the following synthetic schemes and synthetic procedures and conditions for the illustrative intermediates and examples.

In the schemes described below, it is well understood that protecting groups for sensitive or reactive groups are employed where necessary in accordance with general principles of chemistry. Protecting groups are manipulated according to standard methods of organic synthesis (T. W. Greene and P. G. M. Wuts, "Protective Groups in Organic Synthesis", 3rd edition, Wiley, N Y 1999). These groups are removed at a convenient stage of the compound synthesis using methods that are readily apparent to those skilled in the art.

The compounds described herein may be made from commercially available starting materials or synthesized using known organic, inorganic, and/or enzymatic processes.

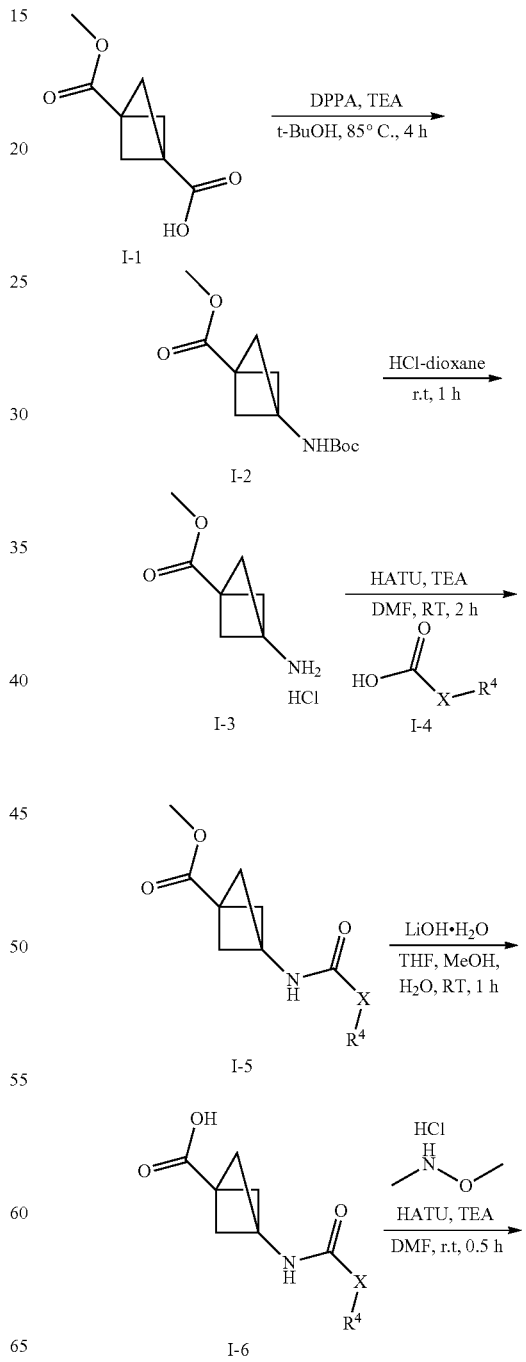

Scheme 1

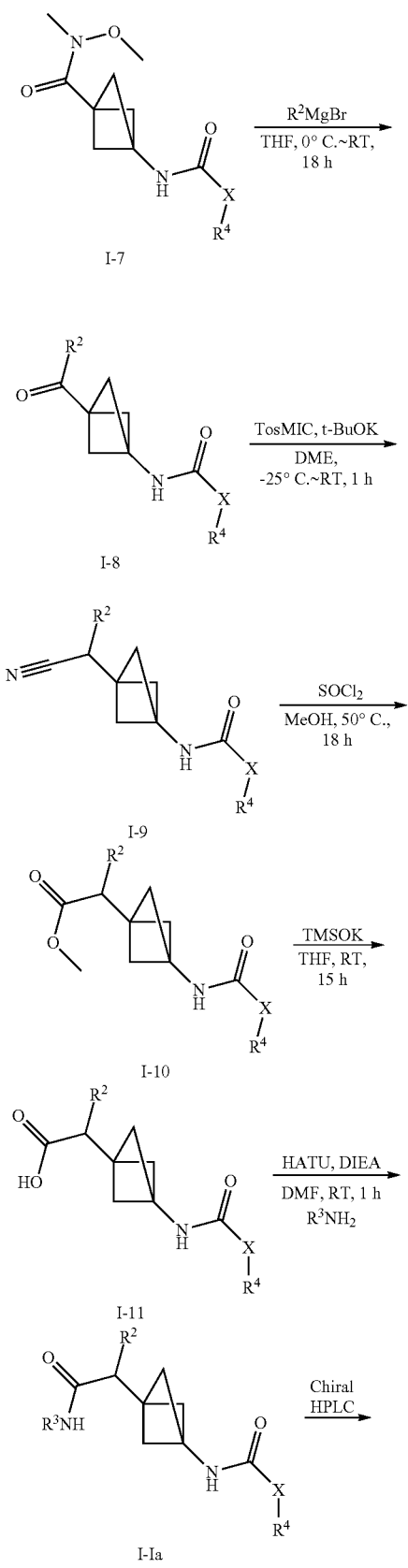

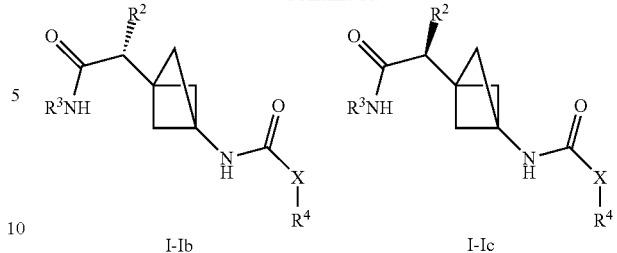

According to Scheme 1, commercially available 3-(methoxycarbonyl)bicyclo[1.1.1]pentane-1-carboxylic acid can be subjected to a Curtius rearrangement, for example by treatment with diphenylphosphoryl azide, trimethylamine and tert-butanol, to afford the corresponding tert-butoxycarbonyl protected amine I-2. The tert-butoxycarbonyl protecting group in intermediate I-2 can be removed by treatment with HCl (as shown), or in other ways, such as by treatment with trifluoroacetic acid. The revealed amine in intermediate I-3 can be converted to an amide I-5 by reaction with a carboxylic acid I-4 using an amide coupling agent such as 1-[bis(dimethylamino)methylene]-1H-1,2,3-triazolo[4,5-b]pyridinium 3-oxide hexafluorophosphate in the presence of an amine such as trimethylamine.

Alternatively, amides I-5 can be prepared by a reaction with acid chlorides in the presence of a base such as trimethylamine. Carbamates or ureas of the formula I-5 can be prepared, for example, by reaction with alkyl chloroformates, or isocyanates, respectively. Hydrolysis of the methyl ester group can be achieved in a wide variety of ways, including, for example, by treatment with lithium hydroxide. The resulting carboxylic acids I-6 can be converted to the corresponding N-methoxy-N-methyl amides I-7 by amide coupling with N,O-dimethylhydroxylamine, using an amide coupling reagent such as 1-[bis(dimethylamino)methylene]-1H-1,2,3-triazolo[4,5-b]pyridinium 3-oxide hexafluorophosphate in the presence of an amine such as trimethylamine.

Treatment of amides I-7 with methyl magnesium Grignard reagent or another alkyl Grignard reagent provides ketones I-8. The ketones I-8 can, in turn, be converted to nitriles I-9 by treatment with toluenesulfonylmethyl isocyanide and potassium tert-butoxide. The resulting nitriles I-9 can be transformed to the corresponding methyl esters I-10 by treatment with anhydrous hydrogen chloride in methanol, which can be readily prepared by the addition of thionyl chloride to anhydrous methanol. Hydrolysis of the methyl esters can be achieved in many ways, including for example, by treatment with potassium trimethylsilanolate. The resulting carboxylic acids I-11 can be converted to racemic amides of the formula I-Ia by reaction with an amine in the presence of an amide coupling reagent such as 1-[bis(dimethylamino)methylene]-1H-1,2,3-triazolo[4,5-b]pyridinium 3-oxide hexafluorophosphate in the presence of an amine such as trimethylamine. Racemic amides I-Ia can be separated into the corresponding single enantiomers by preparative chiral HPLC.

Scheme 2

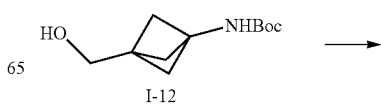

I-12

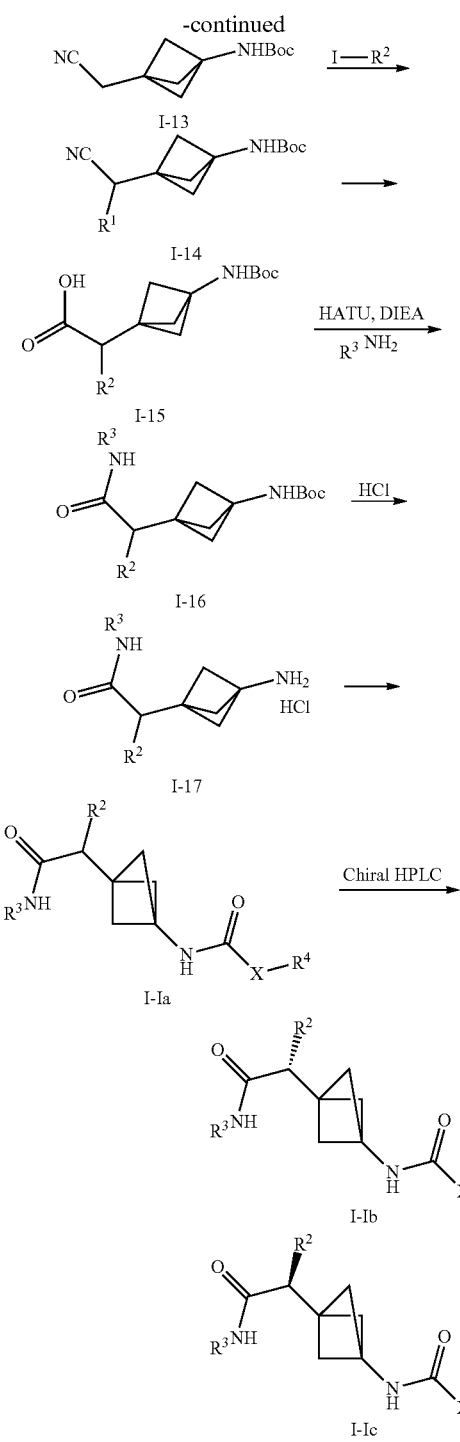

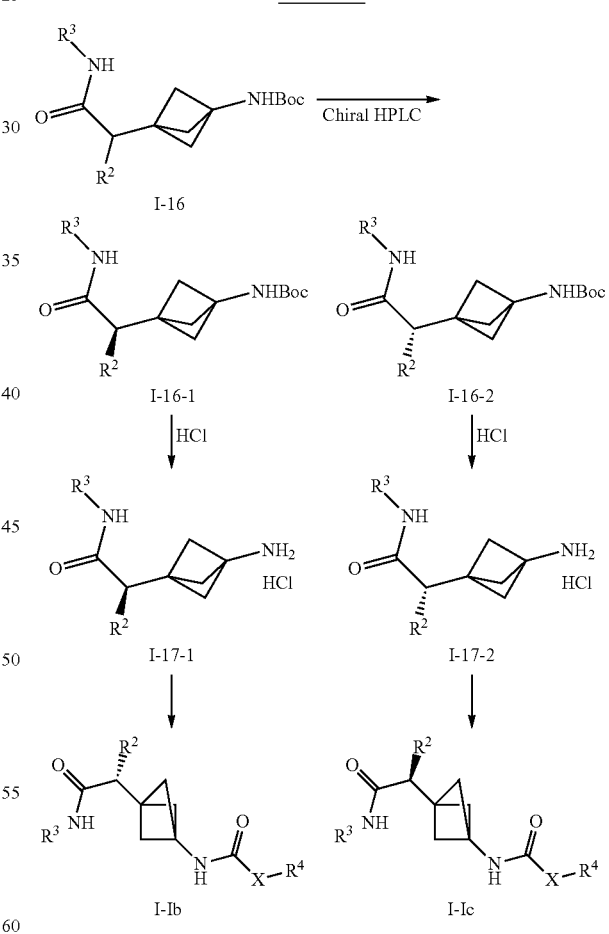

I-14. Hydrolysis of the nitrile group of intermediate I-14 can be achieved in a variety of ways, including by treatment with aqueous potassium hydroxide in a solvent such as ethanol.

The resulting carboxylic acids I-15 can be converted to amides I-16 using amines and any of a number of amide coupling reagents, for example 1-[bis(dimethylamino)methylene]-1H-1,2,3-triazolo[4,5-b]pyridinium 3-oxide hexafluorophosphate in the presence of a base such as diisopropylethylamine. The tert-butoxycarbonyl protective group present in amides I-16 may be removed with an acid such as hydrogen chloride or trifluoroacetic acid to afford amines I-17. Amines I-17, in turn, may be coupled with acid chlorides in the presence of a base, or with carboxylic acids using an amide coupling reagent such as 1-[bis(dimethylamino)methylene]-1H-1,2,3-triazolo[4,5-b]pyridinium 3-oxide hexafluorophosphate to give compounds of the formula I-Ia. Carbamates and ureas of the formula I-Ia may be obtained by treatment of amines I-17 with alkyl chloroformates and isocyanates, respectively. As described in Scheme 1, racemic compounds of the formula I-Ia may be separated to two single enantiomers I-Ib and I-Ic by preparative chiral chromatography.

Alternatively, compounds of formula I-Ia, I-Ib and I-Ic may be prepared according to Scheme 2. Commercially available alcohol I-12 can be converted to the corresponding nitrile I-13 in a variety of ways, for example, by step-wise treatment with methanesulfonyl chloride and trimethylamine to make the mesylate, followed by reaction of the mesylate with sodium cyanide in a solvent such as DMF. Alkylation to the nitrile group of I-13 can be accomplished by initial treatment with two equivalents of a base, such as lithium bis(trimethylsilyl) amide, followed by the addition of an alkyl halide, such as iodomethane to afford compounds In a modification of Scheme 2, compounds of the formula I-Ib and I-Ic can be alternatively prepared in chiral form by initial preparative chiral HPLC separation of the enantiomers of intermediate I-16 to afford single enantiomers I-16-1 (first eluting peak) and I-16-2 (second eluting peak). These can be carried out in the same fashion as described in Scheme 2 to give compounds I-Ib and I-Ic directly without the need for any further separation.

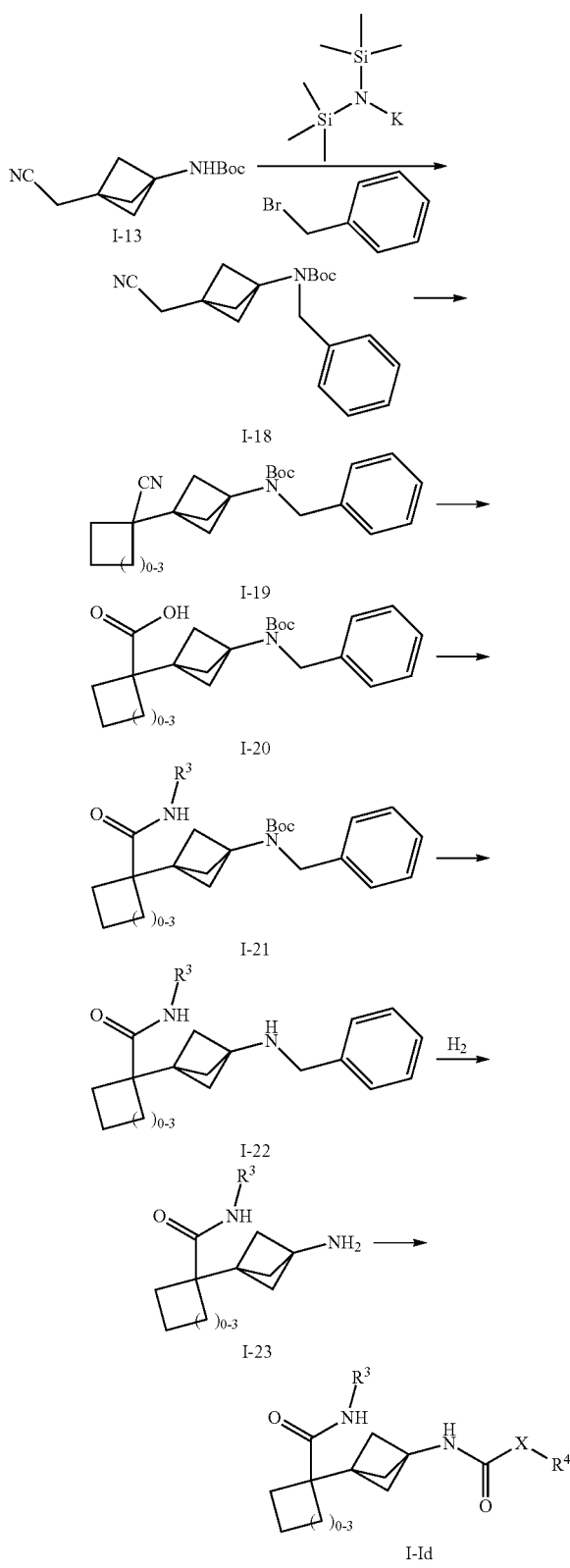

Compounds of formula I-Id may be prepared according to Scheme 3. Intermediate I-13 (Scheme 2) is converted to N-benzyl intermediate I-18 by treatment with a base, such as potassium bis(trimethylsilyl) amide, and benzyl bromide. Cycloalkyl intermediates I-19 of various ring sizes can then be formed by the treatment of I-18 with at least two equivalents of base, such as lithium bis(trimethylsilyl) amide and a dihalo alkyl reagent such as 1,3-dibromopropane. Hydrolysis of the nitrile group present in intermediates I-19 can be achieved in a variety of ways, for example, by warming with aqueous potassium hydroxide solution in a solvent such as ethanol. The resulting acids I-20 can be converted to the corresponding amides I-21 by reaction with amines in the presence of any of a number of amide coupling reagents, such as 1-[bis(dimethylamino)methylene]-1H-1,2,3-triazolo[4,5-b]pyridinium 3-oxide hexafluorophosphate, and a base, for example diisopropylethylamine.

The tert-butoxycarbonyl protective group present in amides I-21 is removed as described previously with acid (e.g., hydrogen chloride or trifluoroacetic acid) to give benzyl amines I-22. The benzyl group present in amines I-22 can be removed by hydrogenolysis, using for example, hydrogen gas in the presence of a catalyst such as palladium (II) hydroxide in an appropriate solvent to provide the primary amines I-23. The primary amines I-23 can be converted to the amides of the formula I-Id by a reaction with acid chlorides and a base like triethylamine, or by reaction with carboxylic acids in the presence of an amide coupling reagent and base, as described in Scheme 2.

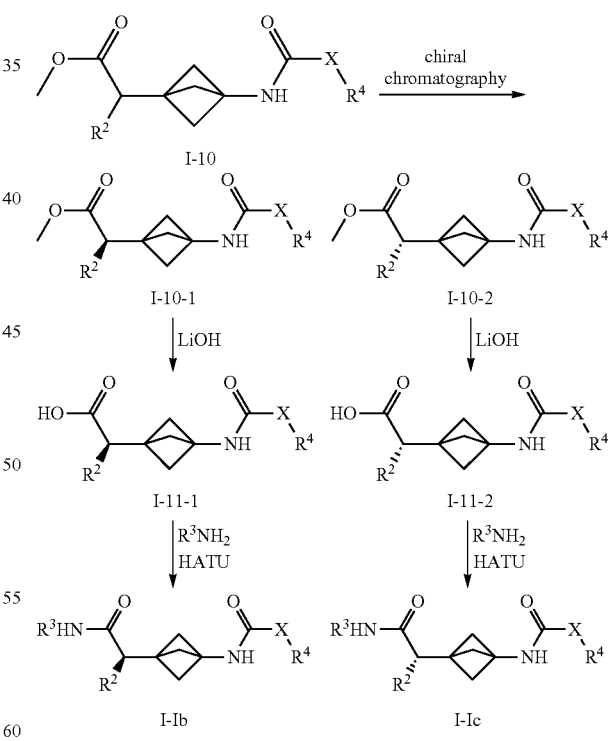

Compounds of formulae I-Ib and I-Ic can also be prepared by a variant of Scheme 1 wherein the chiral resolution step occurs at an earlier stage. According to Scheme 4, methyl ester I-10 (Scheme 1) can be resolved by preparative chiral chromatography. The resulting single enantiomer methyl esters I-10-1 and I-10-2 can be processed in a similar fashion to that described in Scheme 1. Hydrolysis, for example, by treating with lithium hydroxide or another base affords the single enantiomer acids I-11-1 and I-11-2. Subsequent amide formation by reaction with an amine and an amide coupling reagent in the presence of a base such as diisopropylethylamine provides compounds of I-Ib and I-Ic.

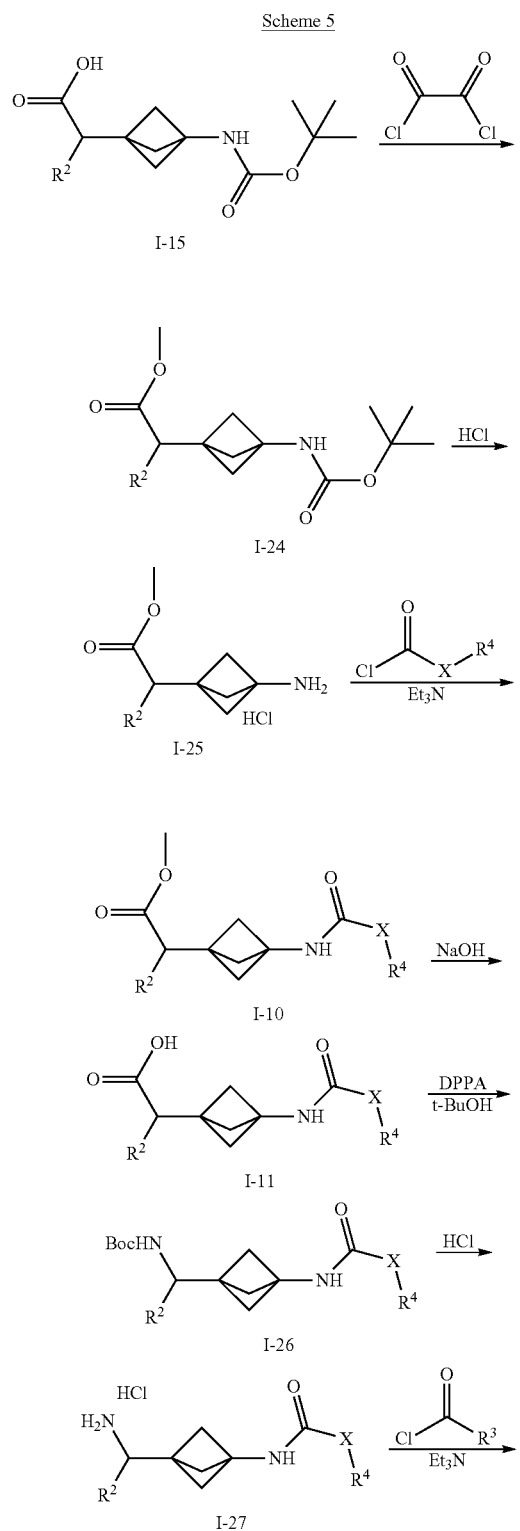

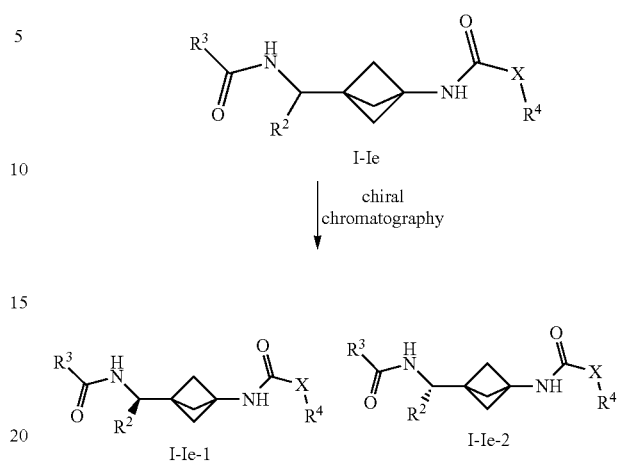

Compounds of the formulae I-Ie, I-Ie-1, and I-Ie-2 may be prepared according to Scheme 5. Carboxylic acid I-15 can be converted to the methyl ester in a variety of ways, including by conversion to the acid chloride with oxalyl chloride and treatment with methanol, or by treatment with trimethylsilyldiazomethane. The tert-butoxycarbonyl protective group of the resulting methyl ester I-24 may be removed by treatment with an acid such as hydrogen chloride or trifluoroacetic acid to afford the primary amine I-25. Amide coupling of amine I-25 can be accomplished by reaction with an acid chloride in the presence of a base such as trimethylamine, or by reaction with a carboxylic acid in the presence of an amide coupling reagent and a base, as described in the previous Schemes.

Subsequent hydrolysis of the methyl ester present in compounds I-10 with a base such as sodium hydroxide affords the carboxylic acids I-11. Curtius rearrangement of the carboxylic acids, for example by treatment with diphenylphosphoryl azide, trimethylamine and tert-butanol provides the tert-butoxycarbonyl protected amine I-26. Removal of the tert-butoxycarbonyl group can be achieved by treatment with acid, for example hydrogen chloride or trifluoroacetic acid, giving the amine I-27. Amide coupling of I-27 to afford amides I-Ie can be accomplished with an acid chloride in the presence of a base such as trimethylamine, or with a carboxylic acid in the presence of an amide coupling reagent and base such as trimethylamine, as described in the previous Schemes. The individual enantiomers of the formula I-Ie-1 and I-Ie-2 may then be obtained by separation using preparative chiral chromatography.

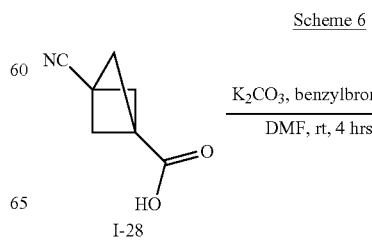

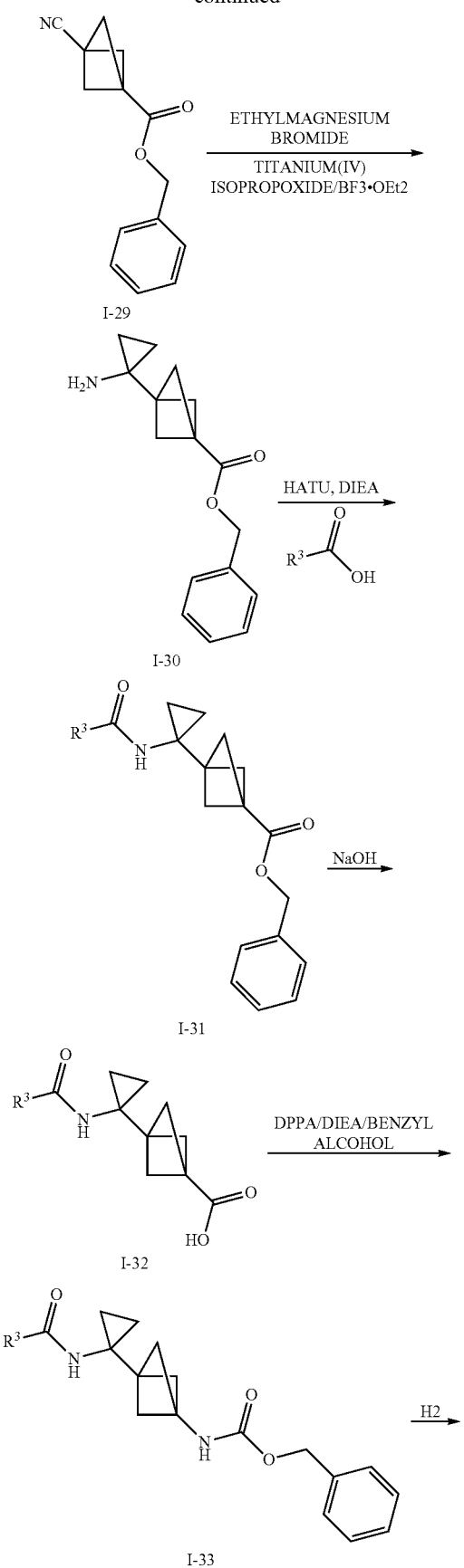

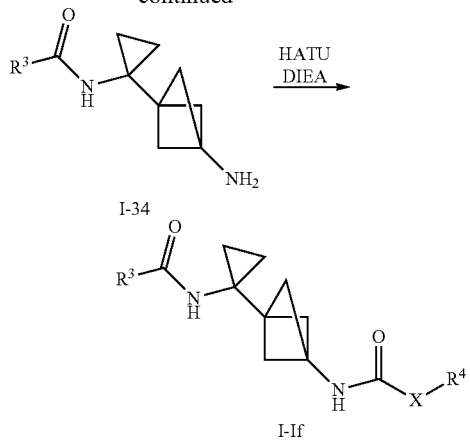

Compounds of the formula I-If may be prepared, for example, according to Scheme 6. Commercially available carboxylic acid I-28 may be protected as its benzyl ester by, for example, treatment with benzyl bromide in the presence of potassium carbonate in a solvent such as DMF. The nitrile group in compound I-29 may be converted to aminocyclopropyl by treatment with ethyl magnesium bromide in the presence of titanium (IV) isporopoxide and boron trifluoride etherate. By using other alkyl magnesium bromides, substituted cyclopropyl groups may be obtained. For example n-propyl magnesium bromide provides methylcyclopropylamine.

The resulting amine in compound I-30 may be converted to amides I-31 in a variety of ways, including by reaction with carboxylic acids in the presence of an amide coupling reagent and a base such as diisopropylethylamine, as described in previous Schemes. Hydrolysis of the benzyl esters I-31 may be achieved by treatment with a base such as sodium hydroxide, or by hydrogenolysis in the presence of a catalyst. Carboxylic acids I-32 can be converted to the corresponding benzyloxycarbonyl protected amines by employing a Curtius rearrangement using diphenyl phosphoryl azide, trimethylamine, and benzyl alcohol. The benzyloxycarbonyl protective group present in compound I-33 may be removed by hydrogenolysis using hydrogen gas and a catalyst such as palladium on carbon. The resulting amines I-34 may be subjected to various amide coupling conditions as described in the previous Schemes to afford compounds of the formula I-If.

Examples

Examples 1 and 2. 3-Chloro-N-(3-(1-((4-fluorophenyl)amino)-1-oxopropan-2-yl)bicyclo[1.1.1]pentan-1-yl)benzamide (Separated Enantiomers)

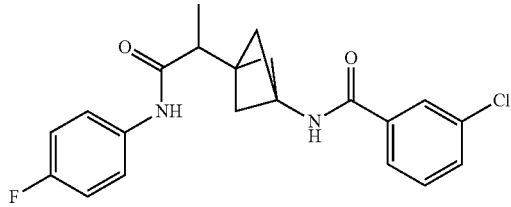

Step 1. Methyl 3-((tert-butoxycarbonyl)amino)bicyclo[1.1.1]pentane-1-carboxylate

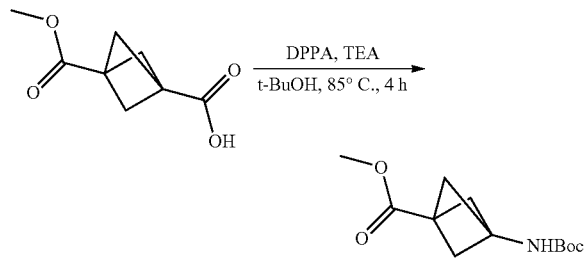

To a stirred solution of 3-(methoxycarbonyl)bicyclo[1.1.1]pentane-1-carboxylic acid (1.0 g, 5.88 mmol) in t-BuOH (20 mL) were successively added TEA (1.5 mL, 10.8 mmol) and DPPA (2.10 g, 7.6 mmol) at RT. After addition, the reaction was stirred at 85° C. for 4 h. The reaction was cooled down, and concentrated at reduced pressure, the residue was purified by silica gel chromatography (SiO$_2$, petroleum ether/EtOAc=10:1) to afford the title compound as a solid. $^1$H NMR (400 MHz, CDCl$_3$) δ 4.95 (br s, 1H), 3.69 (s, 3H), 2.29 (s, 6H), 1.45 (s, 9H).

Step 2. Methyl 3-aminobicyclo[1.1.1]pentane-1-carboxylate Hydrochloride

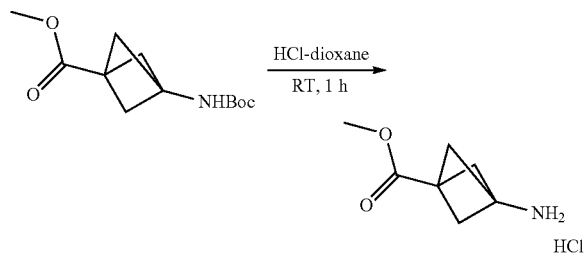

To a flask containing methyl 3-((tert-butoxycarbonyl)amino)bicyclo[1.1.1]pentane-1-carboxylate (480 mg, 1.99 mmol) was added HCl (4M in dioxane, 5 mL) and the mixture was stirred at RT for 1 h. The solvent was removed under reduced pressure to afford the title compound as a solid. The crude product was used in the next step directly without further purification. $^1$H NMR (400 MHz, CD$_3$OD) δ 3.70 (s, 3H), 2.35 (s, 6H).

Step 3. Methyl 3-(3-chlorobenzamido)bicyclo[1.1.1]pentane-1-carboxylate

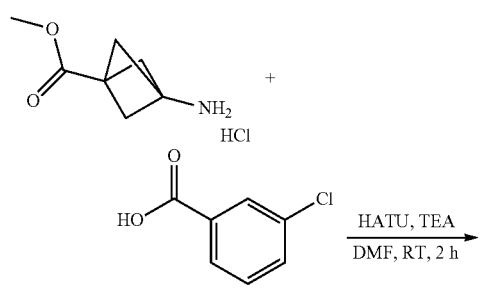

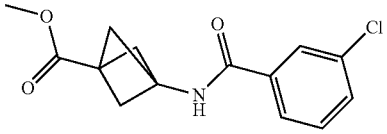

To a mixture of methyl 3-aminobicyclo[1.1.1]pentane-1-carboxylate hydrochloride (320 mg, 1.80 mmol) in DCM (10 mL) at RT was added 3-chlorobenzoic acid (282 mg, 1.80 mmol), HATU (685 mg, 1.80 mmol) and TEA (2.0 mL, 14.4 mmol) and the reaction was stirred for 2 h. After removing the solvent under reduced pressure, the residue was purified by silica gel chromatography (SiO$_2$, petroleum ether/EtOAc=2:1) to afford the title compound as a solid. $^1$H NMR (400 MHz, CDCl$_3$) δ 7.72 (t, J=1.8 Hz, 1H), 7.62 (d, J=8.0 Hz, 1H), 7.46-7.50 (m, 1H), 7.34-7.40 (m, 1H), 6.50 (br s, 1H), 3.71 (s, 3H), 2.48 (s, 6H); MS (ESI) m/z: 279.9 [M+H$^+$]

Step 4. 3-(3-Chlorobenzamido)bicyclo[1.1.1]pentane-1-carboxylic acid

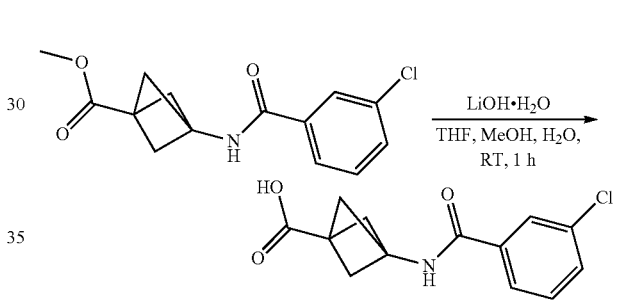

To a solution of methyl 3-(3-chlorobenzamido)bicyclo[1.1.1]pentane-1-carboxylate (240 mg, 0.86 mmol) in MeOH (3 mL)/THF (3 mL)/H$_2$O (1.5 mL) was added lithium hydroxide hydrate (180 mg, 4.3 mmol), and the reaction was stirred at RT for 1 h. The majority of the solvent was removed under reduced pressure. The residue was suspended in H$_2$O and neutralized with 3M HCl. The precipitate was collected and dried in vacuo to afford the title compound as a solid. $^1$H NMR (400 MHz, DMSO-d$_6$) δ 12.47 (br s, 1H), 9.20 (s, 1H), 7.87 (d, J=1.8 Hz, 1H), 7.79 (d, J=7.8 Hz, 1H), 7.58-7.62 (m, 1H), 7.47-7.52 (m, 1H), 2.28 (s, 6H); MS (ESI) m/z: 266.0 [M+H$^+$]

Step 5. 3-(3-Chlorobenzamido)-N-methoxy-N-methylbicyclo[1.1.1]pentane-1-carboxamide

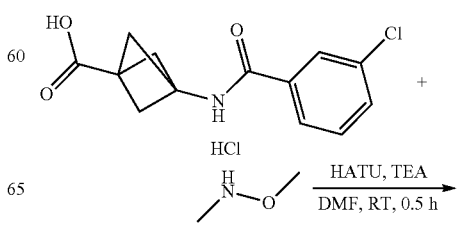

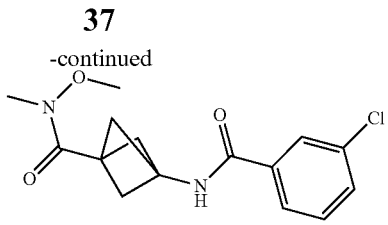

To a solution of 3-(3-chlorobenzamido)bicyclo[1.1.1]pentane-1-carboxylic acid (200 mg, 0.75 mmol) in DMF (5 mL) was added N,O-dimethylhydroxylamine hydrochloride (74 mg, 0.76 mmol), HATU (286 mg, 0.75 mmol) and TEA (0.84 mL, 6.0 mmol) at RT and the reaction was stirred for 0.5 h. The reaction mixture was diluted with H$_2$O and extracted with EtOAc. The organic layers were separated, washed with brine, dried over Na$_2$SO$_4$, and concentrated in vacuo. The residue was purified by silica gel chromatography (DCM/MeOH=20:1) to afford the title compound as a solid. $^1$H NMR (400 MHz, CDCl$_3$) δ 8.01 (s, 1H), 7.72-7.76 (m, 1H), 7.63 (d, J=8.0 Hz, 1H), 7.45-7.49 (m, 1H), 7.33-7.40 (m, 1H), 6.68 (br s, 1H), 3.69 (s, 3H), 3.20 (s, 3H), 2.95 (s, 2H), 2.88 (s, 2H), 2.80 (s, 1H), 2.52 (s, 6H); MS (ESI) m/z: 309.1 [M+H$^+$]

Step 6. N-(3-Acetylbicyclo[1.1.1]pentan-1-yl)-3-chlorobenzamide

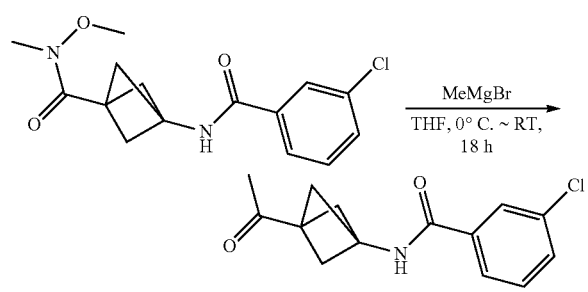

To a solution of 3-(3-chlorobenzamido)-N-methoxy-N-methylbicyclo[1.1.1]pentane-1-carboxamide (370 mg, 1.20 mmol) in THF (8 mL) was added methyl magnesium bromide (0.60 ml, 1.80 mmol, 3 M in diethyl ether) at 0° C. Then the reaction mixture was stirred at RT for 14 h. The reaction was quenched with sat. NH$_4$Cl and extracted with EtOAc. The combined organics were dried over Na$_2$SO$_4$, filtered, and concentrated to afford the title compound as a solid. $^1$H NMR (400 MHz, CDCl$_3$) δ 7.71-7.76 (m, 1H), 7.62 (d, J=7.8 Hz, 1H), 7.47 (dd, J=8.0, 0.8 Hz, 1H), 7.33-7.40 (m, 1H), 6.63 (br s, 1H), 2.44 (s, 6H), 2.18 (s, 3H); MS (ESI) m/z: 264.0 [M+H$^+$]

Step 7. 3-Chloro-N-(3-(1-cyanoethyl)bicyclo[1.1.1]pentan-1-yl)benzamide

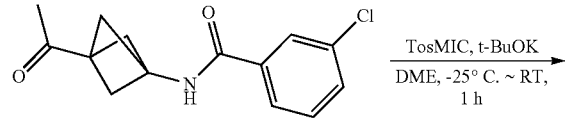

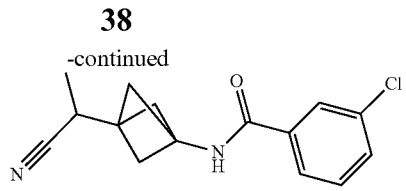

To TosMIC (416 mg, 2.130 mmol) is added a solution of N-(3-acetylbicyclo[1.1.1]pentan-1-yl)-3-chlorobenzamide (260 mg, 0.99 mmol) in 1,2-dimethoxyethane (3 mL). The reaction mixture was cooled to −25° C., followed by the addition of potassium 2-methylpropan-2-olate (3.12 mL, 3.12 mmol) (1 M in THF) dropwise. The reaction mixture was kept stirring at −25° C. for 30 min, then at RT for 1 h. The reaction mixture was neutralized by 3 M HCl to pH=7, and extracted with EtOAc. The organic layers were collected, washed with brine, dried over Na$_2$SO$_4$, and concentrated in vacuo. The residue was purified by prep-TLC (Petroleum ether/EtOAc=2:1) to afford the title compound as a solid.

Step 8. Methyl 2-(3-(3-chlorobenzamido)bicyclo[1.1.1]pentan-1-yl)propanoate

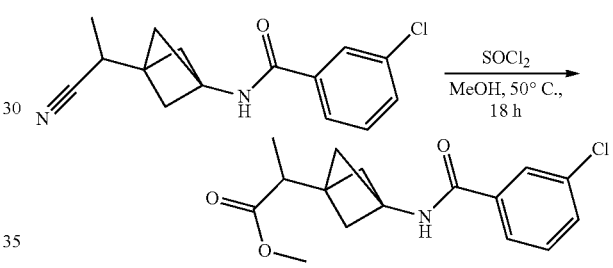

To a solution of 3-chloro-N-(3-(1-cyanoethyl)bicyclo[1.1.1]pentan-1-yl)benzamide (450 mg, 1.64 mmol) in methanol (5 mL) was slowly added SOCl$_2$ (1 mL) at 0° C. Then the reaction was heated to reflux for 18 h. The reaction mixture was concentrated under reduced pressure. The residue was purified by prep-TLC (Petroleum ether/EtOAc=3:1) to afford the title compound as an oil. MS (ESI) m/z: 308.1 [M+H$^+$]

Step 9. 2-(3-(3-chlorobenzamido)bicyclo[1.1.1]pentan-1-yl)propanoic Acid

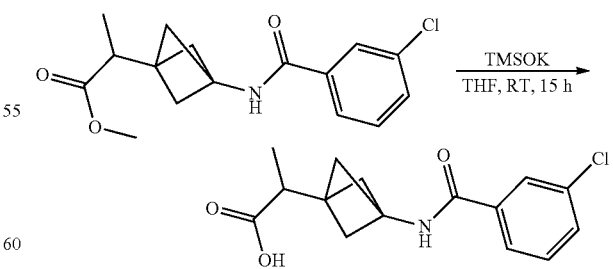

To a solution of methyl 2-(3-(3-chlorobenzamido)bicyclo[1.1.1]pentan-1-yl)propanoate (150 mg, 0.49 mmol) in THF (7.5 mL) was added TMSOK (125 mg, 0.98 mmol) at RT and the reaction mixture was kept stirring at RT for 15 h. Then the mixture was acidified with 0.4 M HCl (in dioxane)

Step 10. 3-Chloro-N-(3-(1-((4-fluorophenyl)amino)-1-oxopropan-2-yl)bicyclo[1.1.1]pentan-1-yl)benzamide (Separated Enantiomers)

to pH=6. The solvent was removed in vacuo to afford the title compound as a solid, which was used directly without further purification. MS (ESI) m/z: 294.1 [M+H⁺]

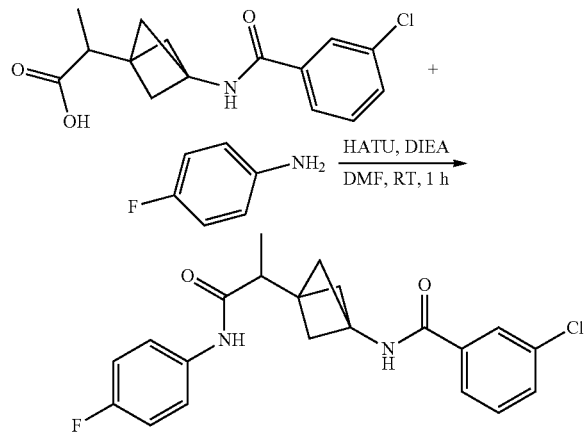

To a solution of 2-(3-(3-chlorobenzamido)bicyclo[1.1.1]pentan-1-yl)propanoic acid (143 mg, 0.49 mmol) in DMF (3 mL) at RT were added HATU (222 mg, 0.58 mmol), 4-fluoroaniline (81 mg, 0.73 mmol) and DIEA (0.34 mL, 1.95 mmol), and the reaction mixture was kept stirring at RT for 1 h. The reaction mixture was purified by reverse phase HPLC (H$_2$O/CH$_3$CN containing 0.1% TFA) to afford the title compound as a racemic solid. Chiral SFC separation (Chiralcel OD 250*30, Mobile phase: 0.1% NH$_3$H$_2$O EtOH afforded two enantiomers:

Ex. 1: Enantiomer 1 (first peak) $^1$H NMR (400 MHz, CD$_3$OD) δ 7.79 (d, J=1.4 Hz, 1H), 7.70 (d, J=7.8 Hz, 1H), 7.49-7.59 (m, 3H), 7.37-7.46 (m, 1H), 6.98-7.09 (m, 2H), 2.76 (q, J=6.8 Hz, 1H), 2.04-2.14 (m, 6H), 1.17 (d, J=6.8 Hz, 3H); MS (ESI) m/z: 387.0 [M+H⁺];

Ex. 2: Enantiomer 2 (second peak): $^1$H NMR (400 MHz, CD$_3$OD) δ 7.80 (t, J=1.6 Hz, 1H), 7.71 (dd, J=7.8, 0.88 Hz, 1H), 7.49-7.58 (m, 3H), 7.38-7.45 (m, 1H), 6.99-7.09 (m, 2H), 2.77 (q, J=6.8 Hz, 1H), 2.05-2.14 (m, 6H), 1.17 (d, J=6.8 Hz, 3H); MS (ESI) m/z: 387.1 [M+H⁺].

Example 3. 3-Chloro-N-(3-(1-((4-fluorophenyl)carbamoyl)cyclobutyl) bicyclo [1.1.1] pentan-1-yl) Benzamide

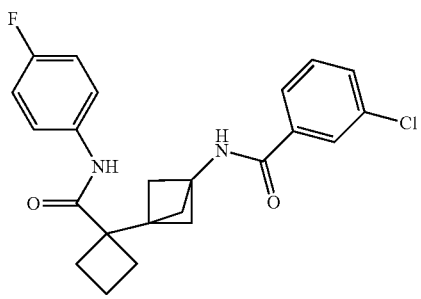 [SMILES: O=C(NC12CC(C3(C(=O)Nc4ccc(F)cc4)CCC3)(C1)C2)c1cccc(Cl)c1]

Step 1: Tert-butyl (3-(cyanomethyl) bicyclo [1.1.1] pentan-1-yl) carbamate

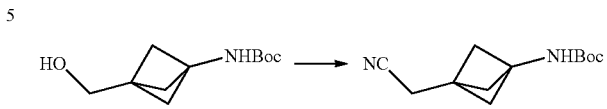

To a solution of tert-butyl (3-(hydroxymethyl)bicyclo[1.1.1]pentan-1-yl)carbamate (1.1 g, 5.16 mmol) in DCM (17.2 ml) at 0° C. was added triethyl amine (0.86 ml, 6.2 mmol) and methane sulfonyl chloride (0.42 ml, 5.42 mmol). The mixture was stirred at 0° C. for 1 h, then diluted with DCM and sat NaHCO$_3$ solution. The organic layer was separated, washed with brine, dried over MgSO$_4$, and concentrated. The residue was taken up in 15 ml of DMF followed by the addition of NaCN (1.01 g, 20.6 mmol). The mixture was stirred at 60° C. for 4 h. The reaction mixture was cooled down, diluted with sat. NaHCO$_3$ aqueous solution, and extracted with EtOAc. The organic layer was separated, washed with brine, dried over MgSO$_4$, and concentrated. The residue was purified by flash chromatography (40 g silica column, 0-50% ethyl acetate/hexanes) to afford the title compound as a solid.

Step 2: Tert-butyl benzyl (3-(cyanomethyl) bicyclo [1.1.1] pentan-1-yl) carbamate

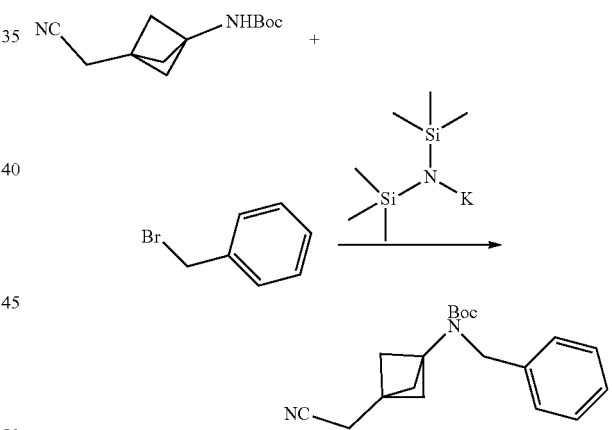

To a solution of tert-butyl (3-(cyanomethyl) bicyclo [1.1.1] pentan-1-yl) carbamate (1.09 g, 4.90 mmol) in THF (16.4 ml) at −78° C. was added potassium bis (trimethylsilyl) amide (5.88 ml, 5.88 mmol). The resulting reaction mixture was stirred for 15 min, followed by the addition of benzyl bromide (0.64 ml, 5.39 mmol). Then cooling bath was removed, and the reaction mixture was allowed to warm up to RT and stirred for 1 h. The mixture was quenched by the addition of H$_2$O and diluted with EtOAc. The organic layer was separated and the aqueous layer was further extracted with EtOAc (2×). The combined organics were washed with brine, dried over MgSO$_4$, and concentrated. The residue was purified by flash chromatography (40 g silica column, 0-50% ethyl acetate/hexanes) to afford the title compound as an oil.

Step 3: Tert-butyl Benzyl (3-(1-cyanocyclobutyl) bicyclo [1.1.1] pentan-1-yl) carbamate

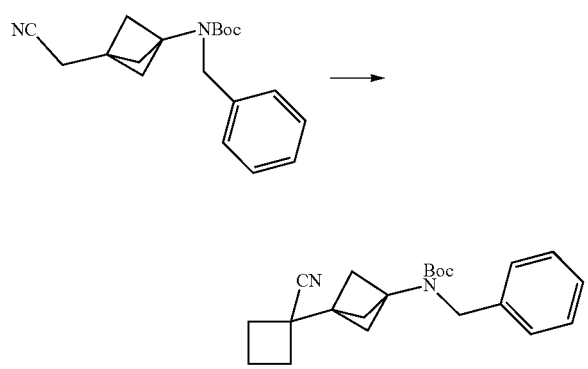

To a solution of tert-butyl benzyl (3-(cyanomethyl) bicyclo [1.1.1] pentan-1-yl) carbamate (635 mg, 2.03 mmol) in THF (6.8 mL) at −78° C. was added lithium bis (trimethylsilyl) amide (4.47 ml, 4.47 mmol). The mixture was stirred at −78° C. for 20 min, then 1, 3-dibromopropane (248 µl, 2.44 mmol) was added. Then cooling bath was removed and the reaction mixture was stirred at RT for 60 min. The mixture was diluted with H₂O and extracted with EtOAc. The organic layer was separated, washed with brine, dried over MgSO₄, and concentrated. The residue was purified by flash chromatography (24 g silica column, 0-100% EtOAc/hexanes) to afford the title compound as an oil.

Step 4: 1-(3-(Benzyl (tert-butoxycarbonyl) amino) bicyclo [1.1.1] pentan-1-yl) cyclobutanecarboxylic acid

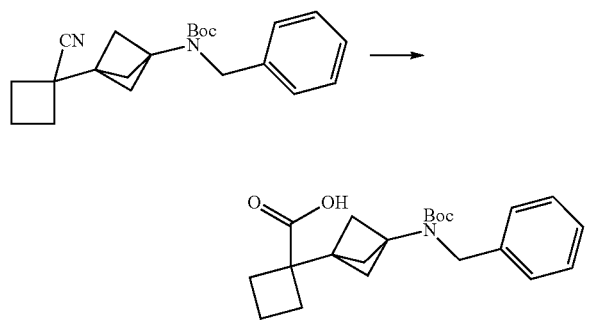 [SMILES: CC(C)(C)OC(=O)N(Cc1ccccc1)C12CC(C3(C#N)CCC3)(C1)C2 ; CC(C)(C)OC(=O)N(Cc1ccccc1)C12CC(C3(C(=O)O)CCC3)(C1)C2]

To a 20 ml of microwave reaction vial was added potassium hydroxide powder (2.37 g, 42.3 mmol), water (5.29 mL) and a solution of tert-butyl benzyl(3-(1-cyanocyclobutyl)bicyclo[1.1.1]pentan-1-yl) carbamate (373 mg, 1.06 mmol) in EtOH (5.29 mL). The resulting solution was heated up to 100° C. and stirred for 48 h. The reaction mixture was then cooled down, neutralized with 1N HCl to pH=3-4. The mixture was extracted with EtOAc, and the combined organics were washed with brine, dried over MgSO₄, and concentrated. The residue was purified by flash chromatography (24 g silica column, 0-50% EtOAc/hexanes) to afford the title compound as an oil.

Step 5: Tert-butyl benzyl (3-(1-((4-fluorophenyl) carbamoyl) cyclobutyl) bicyclo [1.1.1] pentan-1-yl) carbamate

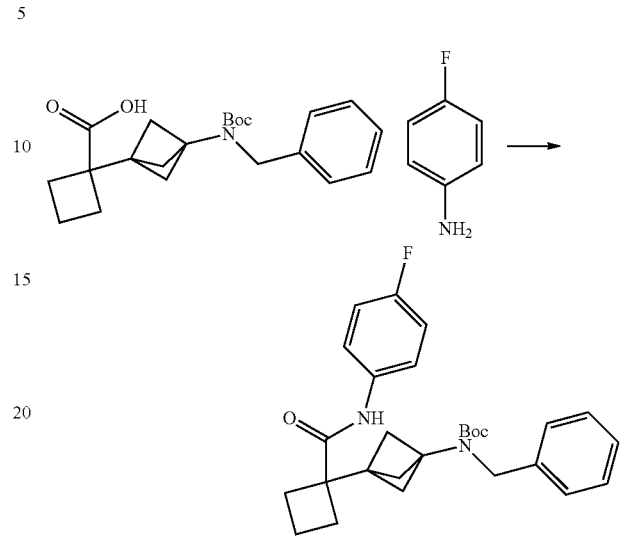

To a solution of 1-(3-(benzyl (tert-butoxycarbonyl) amino) bicyclo [1.1.1] pentan-1-yl) cyclobutanecarboxylic acid (295 mg, 0.79 mmol) in DMF (3.97 mL) was added 4-fluoroaniline (151 µl, 1.59 mmol), HATU (393 mg, 1.03 mmol) and Hunig's base (416 µl, 2.38 mmol). The mixture was stirred at RT overnight. The reaction mixture was diluted with sat. NaHCO₃ aqueous solution and extracted with EtOAc. The organic layer was separated, washed with H₂O, brine, dried over MgSO₄, and concentrated. The residue was purified by flash chromatography (24 g silica column, 0-50% EtOAc/hexanes) afford the title compound as an oil.

Step 6: 1-(3-(Benzyl amino) bicyclo [1.1.1] pentan-1-yl)-N-(4 fluorophenyl) cyclobutanecarboxamide

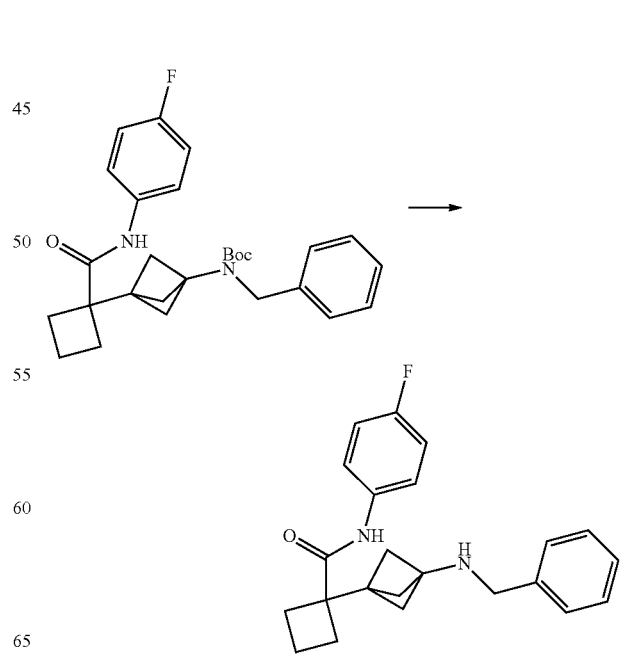

To a solution of tert-butyl benzyl (3-(1-((4-fluorophenyl) carbamoyl) cyclobutyl) bicyclo [1.1.1] pentan-1-yl) carbamate (354 mg, 0.76 mmol) in dioxane (1.5 mL) was added HCl in dioxane (4.0M, 1.0 mL). The mixture was stirred at RT overnight. The mixture was concentrated and diluted with Sat.NaHCO₃ aqueous solution, extracted with 25% isopropanol in chloroform (3×), dried over MgSO₄ and concentrated to afford the title compound as an oil.

Step 7: 1-(3-Aminobicyclo [1.1.1] pentan-1-yl)-N-(4-fluorophenyl) cyclobutane-1-carboxamide

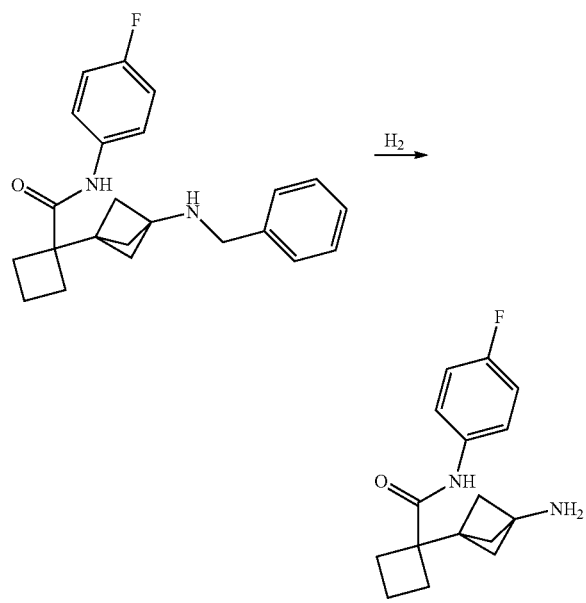

To a solution of 1-(3-(benzylamino) bicyclo [1.1.1] pentan-1-yl)-N-(4-fluorophenyl) cyclobutanecarboxamide (220 mg, 0.60 mmol) in THF (755 μl) and EtOAc (755 μl) was added palladium (II) hydroxide (20% on carbon) (30 mg, 0.043 mmol). The resulting reaction mixture was degassed and stirred at RT under H₂ balloon overnight. Then the reaction mixture was filtered through a Celite cartridge and rinsed with ethyl acetate, concentrated to afford the title compound as a solid.

Step 8: 3-Chloro-N-(3-(1-((4-fluorophenyl) carbamoyl) cyclobutyl) bicyclo [1.1.1] pentan-1-yl) benzamide (Ex. 3)

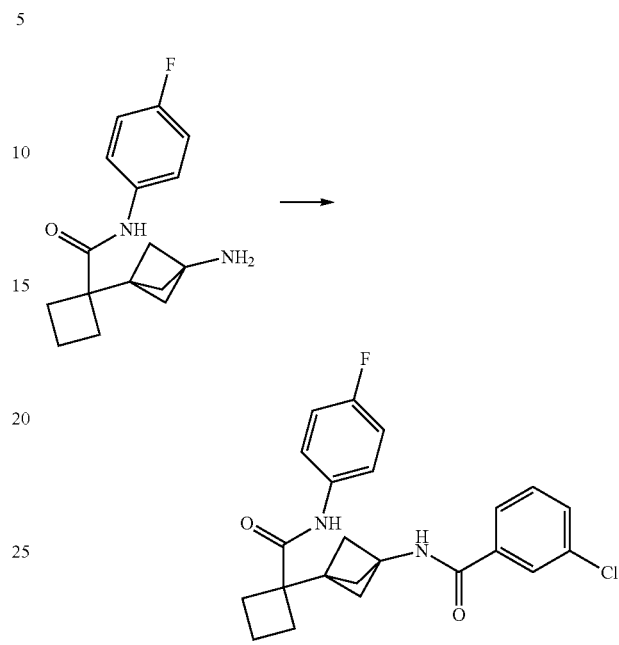

To a solution of 1-(3-aminobicyclo[1.1.1]pentan-1-yl)-N-(4-fluorophenyl)cyclobutanecarboxamide (38 mg, 0.14 mmol) in THF (1 ml) was added triethylamine (0.077 ml, 0.55 mmol) and 3-chlorobenzoyl chloride (36.4 mg, 0.21 mmol). The mixture was stirred at RT for 2 h. The reaction mixture was diluted sat. NaHCO₃ aqueous solution, and extracted with EtOAc. The organic layer was separated, washed with brine, dried over MgSO₄, and concentrated. The residue was purified by flash chromatography (12 g silica column, 0-50% EtOAc/hexanes) to afford the title compound as a powder. LCMS: 413.1 [M+H]⁺; ¹H NMR (499 MHz, DMSO-d₆) δ 9.24 (s, 1H), 9.10 (s, 1H), 7.87 (s, 1H), 7.78 (d, J=7.6 Hz, 1H), 7.64 (dd, J=8.4, 5.2 Hz, 2H), 7.59 (d, J=7.8 Hz, 1H), 7.49 (t, J=7.8 Hz, 1H), 7.14 (t, J=8.7 Hz, 2H), 2.35 (q, J=9.8 Hz, 2H), 2.07 (d, J=9.5 Hz, 2H), 2.01 (s, 6H), 1.81-1.64 (m, 2H).

The following compounds in Table 1 were prepared by following similar procedures used for the synthesis of Example 3.

TABLE 1

| Ex. # | Structure | Chemical Name | Mass [M + H]⁺ |
|---|---|---|---|
| Ex. 4 | (structure shown) | 3-cyano-N-(3-(1-((4-fluorophenyl)carbamoyl)cyclobutyl)bicyclo[1.1.1]pentan-1-yl)benzamide | 404.1 |

Example 5. 3,4-Dichloro-N-(3-(1-((4-fluorophenyl)carbamoyl)cyclobutyl)bicyclo[1.1.1]pentan-1-yl)benzamide

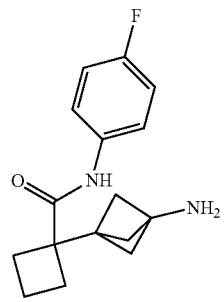

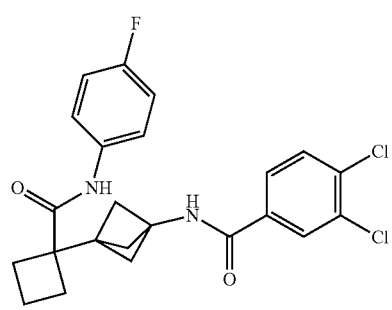

To a solution of 1-(3-aminobicyclo[1.1.1]pentan-1-yl)-N-(4-fluorophenyl)cyclobutanecarboxamide (38 mg, 0.14 mmol) in THF (1 ml) was added Et₃N (0.077 ml, 0.55 mmol) and 3,4-dichlorobenzoyl chloride (44 mg, 0.21 mmol). The mixture was stirred at RT for 2 h. The reaction mixture was diluted with sat. NaHCO₃, and extracted with EtOAc. The organic layer was separated, washed with brine, dried over MgSO₄, and concentrated. The residue was purified by flash chromatography (0-50% EtOAc/hexanes) to give the title compound as a solid. LCMS: 447 [M+H]⁺; ¹H NMR (499 MHz, DMSO-d₆)¹H NMR (499 MHz, DMSO-d₆) δ 9.23 (s, 1H), 9.17 (s, 1H), 8.07 (s, 1H), 7.81 (d, J=8.4 Hz, 1H), 7.75 (d, J=8.4 Hz, 1H), 7.64 (dd, J=8.7, 5.1 Hz, 2H), 7.14 (t, J=8.8 Hz, 2H), 2.35 (q, J=9.4 Hz, 2H), 2.01 (s, 8H), 1.88-1.57 (m, 2H).

Examples 6 and 7. 3-Chloro-N-(3-(1-((4-chlorophenyl)amino)-1-oxopropan-2-yl)bicyclo[1.1.1]pentan-1-yl) Benzamide (Separated Enantiomers)

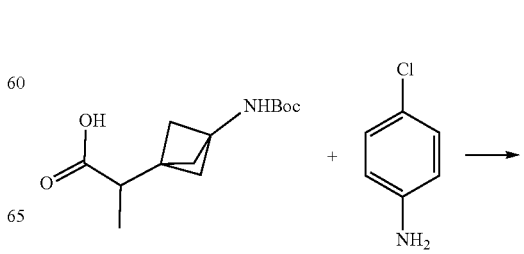

Step 1: Tert-butyl (3-(1-cyanoethyl) Bicycle [1.1.1]pentan-1-yl) carbamate

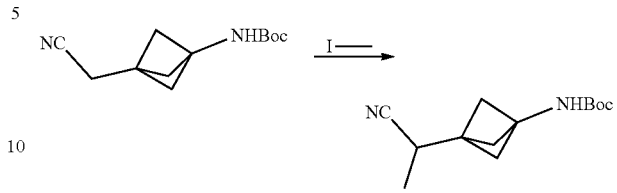

To a solution of tert-butyl (3-(cyanomethyl) bicyclo[1.1.1] pentan-1-yl) carbamate (1.12 g, 5.04 mmol) in THF (6 ml) at −30° C. was added lithium bis (trimethylsilyl) amide (11.1 ml, 11.1 mmol). The mixture was stirred at −30° C. for 20 min, and then the solution of methyl iodide (0.32 ml, 5.0 mmol) in 1 ml of THF was added dropwise. After addition, the reaction mixture was stirred under around −20° C. for 30 min. The reaction mixture was diluted with sat. NaHCO₃, and extracted with EtOAc. The organic layer was separated, washed with brine, dried over MgSO₄, and concentrated. The residue was purified by flash chromatography (0-50% EtOAc/hexanes) to afford the title compound as a solid.

Step 2: 2-(3-((Tert-butoxycarbonyl) amino) bicyclo[1.1.1] pentan-1-yl) Propanoic

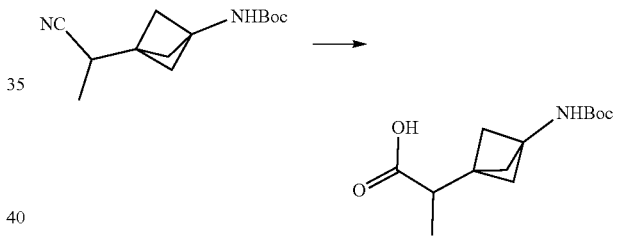

To a microwave reaction vial was added KOH (950 mg, 16.9 mmol), H₂O (2.1 mL), followed by a solution of tert-butyl (3-(1-cyanoethyl) bicyclo [1.1.1] pentan-1-yl) carbamate (100 mg, 0.42 mmol) in EtOH (2.1 mL). The resultant solution was heated at 100° C. for 18 h. The mixture was cooled down, neutralized with 1N HCl to pH 3-4. The mixture was extracted with 25% IPA in chloroform twice. The combined organics were washed with brine, dried over MgSO₄, and concentrated to afford the title compound as a solid. This material was used directly for next step.

Step 3: Tert-butyl (3-(1-((4-chlorophenyl) amino)-1-oxopropan-2-yl) bicyclo [1.1.1] pentan-1-yl) carbamate -continued

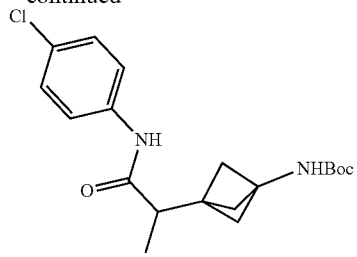

To a solution of 2-(3-((tert-butoxycarbonyl) amino) bicyclo [1.1.1] pentan-1-yl) propanoic acid (108 mg, 0.423 mmol) in DMF (1.5 ml) was added 4-chloroaniline (108 mg, 0.846 mmol), HATU (209 mg, 0.55 mmol) and DIEA (0.30 ml, 1.69 mmol). The mixture was stirred at RT overnight. The reaction mixture was diluted with sat. NaHCO$_3$, and extracted with EtOAc. The organic layer was separated, washed with water, brine, dried over MgSO$_4$, and concentrated. The residue was purified by flash chromatography (24 g silica column, 0-50% EtOAc/hexanes) to afford the title compound as a solid.

Step 4: 2-(3-Aminobicyclo [1.1.1] pentan-1-yl)-N-(4-chlorophenyl) Propanamide Hydrochloride

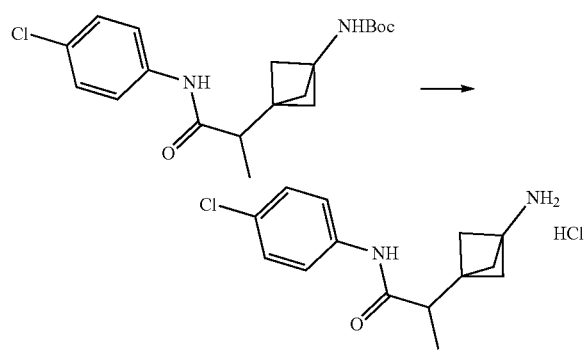

To a solution of tert-butyl (3-(1-((4-chlorophenyl) amino)-1-oxopropan-2-yl) bicyclo [1.1.1] pentan-1-yl) carbamate (25 mg, 0.069 mmol) in dioxane (0.5 ml) was added HCl (4.0M in dioxane, 1.0 ml). The mixture was stirred at RT overnight. Then the resulting mixture was concentrated under reduced pressure to afford the title compound as a solid. The resulting product was used for next step without further purification.

Step 5: 3-Chloro-N-(3-(1-((4-chlorophenyl) amino)-1-oxopropan-2-yl) bicyclo [1.1.1] pentan-1-yl) Benzamide

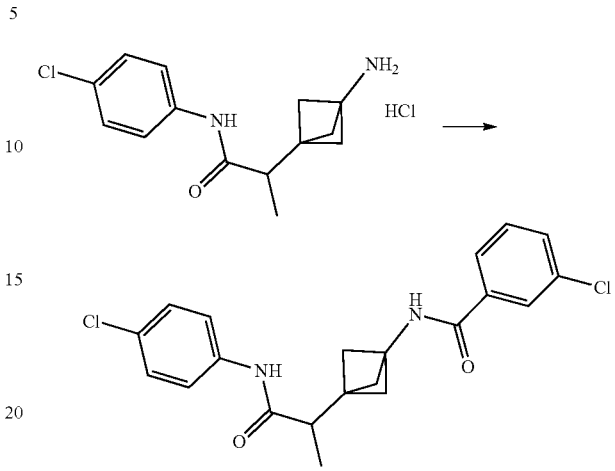

To a solution of 2-(3-aminobicyclo[1.1.1]pentan-1-yl)-N-(4-chlorophenyl)propanamide hydrochloride (18 mg, 0.068 mmol) in THF (1 ml) was added triethylamine (0.5 ml, 3.59 mmol) and 3-chlorobenzoyl chloride (17.8 mg, 0.10 mmol). The mixture was stirred at RT for 20 min. The reaction mixture was diluted with sat. NaHCO$_3$ solution and extracted with EtOAc. The organic layer was separated, washed with brine, dried over MgSO$_4$, and concentrated. The residue was purified by flash chromatography (12 g silica column, 0-50% EtOAc/hexanes) to afford the title compound as a solid.

The racemic 3-chloro-N-(3-(1-((4-chlorophenyl)amino)-1-oxopropan-2-yl)bicyclo [1.1.1] pentan-1-yl) benzamide was submitted to chiral SFC separation (Column Lux-4, 21×250, Condition MeOH+0.25% DMEA) to afford two separate enantiomers as solids.

Ex. 6 (peak 1): LCMS: 404.1 [M+H]$^+$; $^1$H NMR (499 MHz, DMSO-d$_6$) δ 9.95 (s, 1H), 9.07 (s, 1H), 7.87 (s, 1H), 7.78 (d, J=7.6 Hz, 1H), 7.63 (d, J=8.5 Hz, 2H), 7.59 (d, J=7.7 Hz, 1H), 7.48 (t, J=7.8 Hz, 1H), 7.36 (d, J=8.5 Hz, 2H), 2.74 (d, J=6.7 Hz, 1H), 2.01-1.90 (m, 6H), 1.07 (q, J=6.6 Hz, 3H).

Ex. 7 (peak 2): LCMS: 404.1 [M+H]$^+$; $^1$H NMR (499 MHz, DMSO-d$_6$) δ 9.95 (s, 1H), 9.07 (s, 1H), 7.87 (s, 1H), 7.78 (d, J=7.6 Hz, 1H), 7.63 (d, J=8.5 Hz, 2H), 7.59 (d, J=7.7 Hz, 1H), 7.48 (t, J=7.8 Hz, 1H), 7.36 (d, J=8.5 Hz, 2H), 2.74 (d, J=6.7 Hz, 1H), 2.01-1.90 (m, 6H), 1.07 (q, J=6.6 Hz, 3H).

The following compounds in Table 2 were prepared using similar procedures described for Examples 6 and 7.

TABLE 2

| Ex. # | Structure | Chemical Name | Mass [M + H]+ |
|---|---|---|---|
| 8 | 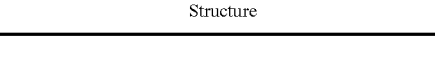 | 3,4-dichloro-N-(3-(1-((4-fluorophenyl)amino)-1-oxopropan-2-yl)bicyclo[1.1.1]pentan-1-yl)benzamide (faster eluting enantiomer) | 421.0 |

TABLE 2-continued

| Ex. # | Structure | Chemical Name | Mass [M + H]+ |
|---|---|---|---|
| 9 | 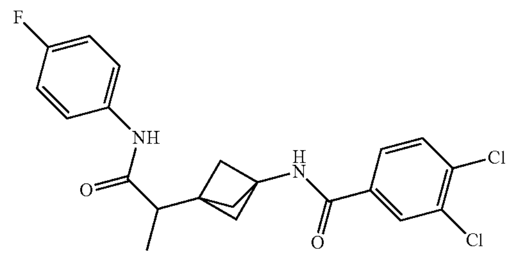 [SMILES: CC(C(=O)Nc1ccc(F)cc1)C12CC(NC(=O)c3ccc(Cl)c(Cl)c3)(C1)C2] | 3,4-dichloro-N-(3-(1-((4-fluorophenyl)amino)-1-oxopropan-2-yl)bicyclo[1.1.1]pentan-1-yl)benzamide (slower eluting enantiomer) | 421.0 |
| 10 | 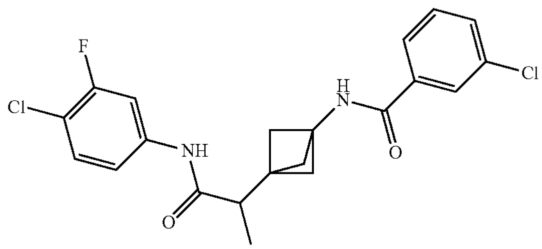 [SMILES: CC(C(=O)Nc1ccc(Cl)c(F)c1)C12CC(NC(=O)c3cccc(Cl)c3)(C1)C2] | 3-chloro-N-(3-(1-((4-chloro-3-fluorophenyl)amino)-1-oxopropan-2-yl)bicyclo[1.1.1]pentan-1-yl)benzamide (faster eluting enantiomer) | 421.0 |
| 11 | 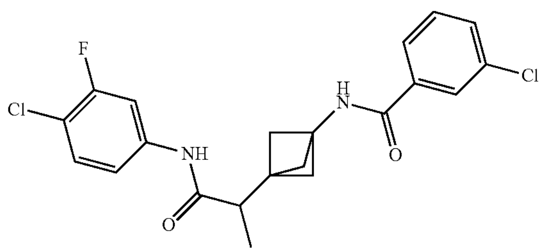 [SMILES: CC(C(=O)Nc1ccc(Cl)c(F)c1)C12CC(NC(=O)c3cccc(Cl)c3)(C1)C2] | 3-chloro-N-(3-(1-((4-chloro-3-fluorophenyl)amino)-1-oxopropan-2-yl)bicyclo[1.1.1]pentan-1-yl)benzamide (slower eluting enantiomer) | 421.0 |
| 12 | 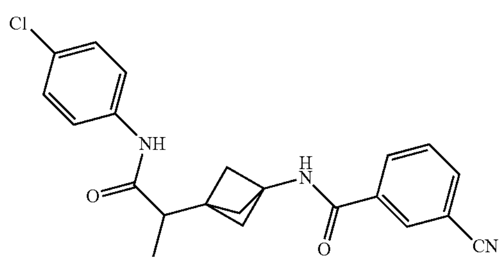 [SMILES: CC(C(=O)Nc1ccc(Cl)cc1)C12CC(NC(=O)c3cccc(C#N)c3)(C1)C2] | N-(3-(1-((4-chlorophenyl)amino)-1-oxopropan-2-yl)bicyclo[1.1.1]pentan-1-yl)-3-cyanobenzamide (faster eluting enantiomer) | 394.1 |
| 13 | 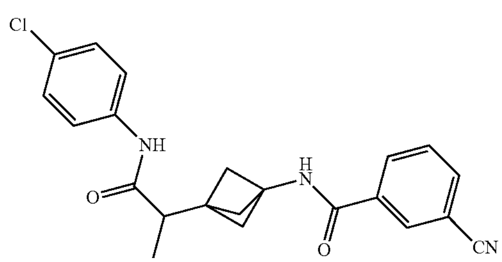 [SMILES: CC(C(=O)Nc1ccc(Cl)cc1)C12CC(NC(=O)c3cccc(C#N)c3)(C1)C2] | N-(3-(1-((4-chlorophenyl)amino)-1-oxopropan-2-yl)bicyclo[1.1.1]pentan-1-yl)-3-cyanobenzamide (slower eluting enantiomer) | 394.1 |
| 14 | 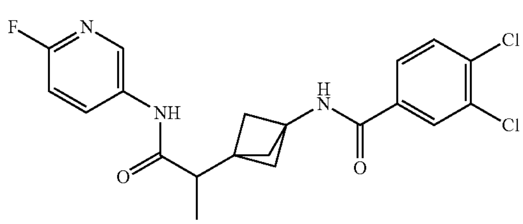 [SMILES: CC(C(=O)Nc1ccc(F)nc1)C12CC(NC(=O)c3ccc(Cl)c(Cl)c3)(C1)C2] | 3,4-dichloro-N-(3-(1-((6-fluoropyridin-3-yl)amino)-1-oxopropan-2-yl)bicyclo[1.1.1]pentan-1-yl)benzamide (slower eluting enantiomer) | 422.0 |

TABLE 2-continued

| Ex. # | Structure | Chemical Name | Mass [M + H]+ |
|---|---|---|---|
| 15 | 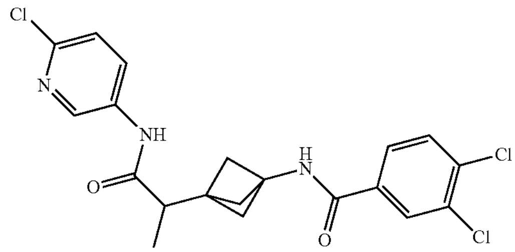 [SMILES: CC(C(=O)Nc1ccc(Cl)nc1)C12CC(NC(=O)c3ccc(Cl)c(Cl)c3)(C1)C2] | 3,4-dichloro-N-(3-(1-((6-chloropyridin-3-yl)amino)-1-oxopropan-2-yl)bicyclo[1.1.1]pentan-1-yl)benzamide (slower eluting enantiomer) | 440.1 |
| 16 | 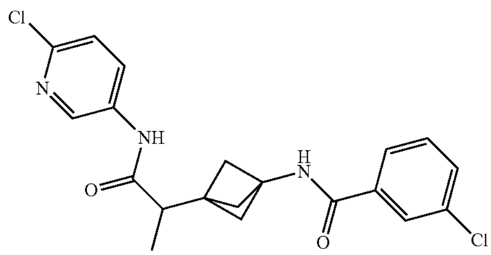 [SMILES: CC(C(=O)Nc1ccc(Cl)nc1)C12CC(NC(=O)c3cccc(Cl)c3)(C1)C2] | 3-chloro-N-(3-(1-((6-chloropyridin-3-yl)amino)-1-oxopropan-2-yl)bicyclo[1.1.1]pentan-1-yl)benzamide (faster eluting enantiomer) | 404.0 |
| 17 | 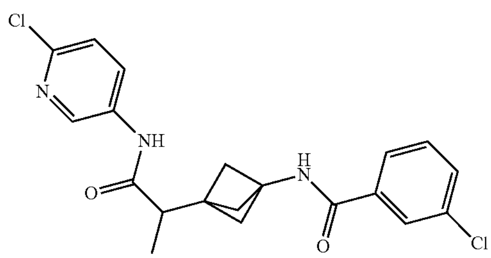 [SMILES: CC(C(=O)Nc1ccc(Cl)nc1)C12CC(NC(=O)c3cccc(Cl)c3)(C1)C2] | 3-chloro-N-(3-(1-((6-chloropyridin-3-yl)amino)-1-oxopropan-2-yl)bicyclo[1.1.1]pentan-1-yl)benzamide (slower eluting enantiomer) | 404.0 |
| 18 | 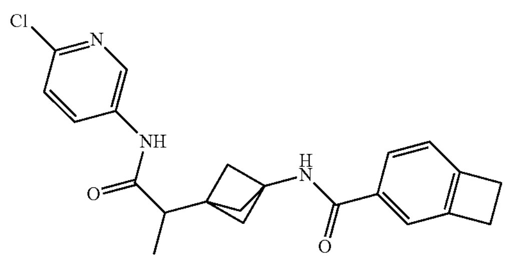 [SMILES: CC(C(=O)Nc1ccc(Cl)nc1)C12CC(NC(=O)c3ccc4c(c3)CC4)(C1)C2] | N-(3-(1-((6-chloropyridin-3-yl)amino)-1-oxopropan-2-yl)bicyclo[1.1.1]pentan-1-yl)bicyclo[4.2.0]octa-1(6),2,4-triene-3-carboxamide | 396.2 |

Examples 19 and 20. Cyclopropyl (3-(1-((4-chlorophenyl)amino)-1-oxopropan-2-yl)bicyclo [1.1.1] pentan-1-yl) carbamate (Separated Enantiomers)

Cyclopropyl (3-(1-((4-chlorophenyl) amino)-1-oxopropan-2-yl) bicyclo [1.1.1] pentan-1-yl) carbamate

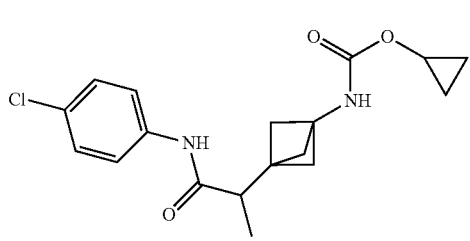 [SMILES: CC(C(=O)Nc1ccc(Cl)cc1)C12CC(NC(=O)OC3CC3)(C1)C2]

+

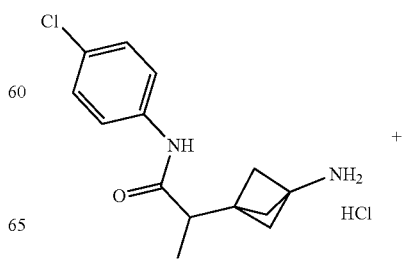

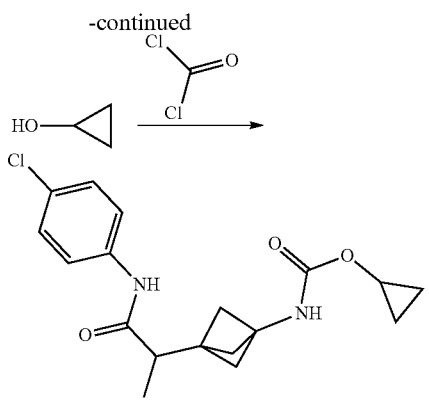

To a solution of cyclopropanol (30 μl, 0.47 mmol) in DCM (712 μl) and cooled to 0° C. was added phosgene (338 μl, 0.47 mmol) followed by the addition of potassium carbonate (148 mg, 1.07 mmol), and the reaction was allowed to stir at 0° C. for 1.5 h. Then to the reaction was added 2-(3-aminobicyclo [1.1.1] pentan-1-yl)-N-(4-chlorophenyl) propanamide hydrochloride (64.3 mg, 0.213 mmol) followed by N, N-diisopropylethylamine (152 μl, 0.85 mmol). The reaction mixture was allowed to stir at RT for 5 h. The resulting mixture was diluted with water and extracted material with EA, dried over Na$_2$SO$_4$, and concentrated. The residue was purified by silica-gel flash chromatography (0-50% 3:1 EtOAc: ethanol/hexanes) to afford the title compound as a powder.

The racemic cyclopropyl (3-(1-((4-chlorophenyl)amino)-1-oxopropan-2-yl) bicyclo [1.1.1] pentan-1-yl) carbamate was submitted to chiral SFC separation (column IG, Condition MeOH+0.25% DMEA) to afford two enantiomers as solids.

Ex. 19 (peak 1): LCMS: 349.1 [M+H]$^+$; $^1$H NMR (600 MHz, DMSO-d$_6$) δ 9.89 (s, 1H), 7.77 (s, 1H), 7.61 (d, J=8.8 Hz, 2H), 7.34 (d, J=8.8 Hz, 2H), 3.89 (s, 1H), 2.69 (q, J=6.2 Hz, 1H), 1.87-1.67 (m, 6H), 1.03 (d, J=6.8 Hz, 3H), 0.67-0.52 (m, 4H).

Ex. 20 (peak 2): LCMS: 349.1 [M+H]$^+$; $^1$H NMR (600 MHz, DMSO-d$_6$) δ 9.89 (s, 1H), 7.77 (s, 1H), 7.61 (d, J=8.8 Hz, 2H), 7.34 (d, J=8.8 Hz, 2H), 3.89 (s, 1H), 2.69 (q, J=6.2 Hz, 1H), 1.87-1.67 (m, 6H), 1.03 (d, J=6.8 Hz, 3H), 0.67-0.52 (m, 4H).

Examples 21 and 22: 3,4-Dichloro-N-(3-(1-(4-fluorobenzamido)ethyl) bicyclo [1.1.1] pentan-1-yl) Benzamide (Separated Enantiomers)

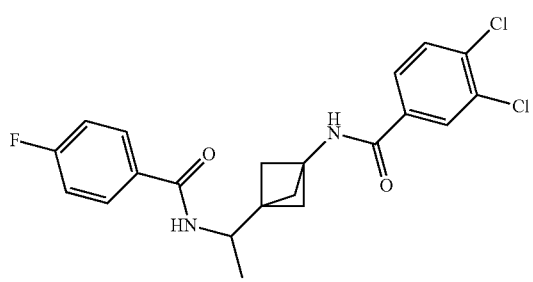 [SMILES: CC(NC(=O)c1ccc(F)cc1)C12CC(NC(=O)c3ccc(Cl)c(Cl)c3)(C1)C2]

Step 1: Methyl 2-(3-((tert-butoxycarbonyl) amino) bicyclo [1.1.1] pentan-1-yl) Propanoate

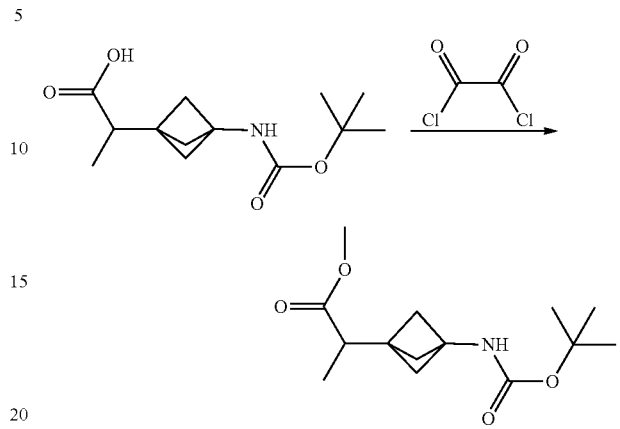

To a suspension of 2-(3-((tert-butoxycarbonyl) amino) bicyclo [1.1.1] pentan-1-yl) propanoic acid (177 mg, 0.693 mmol) in DCM (2311 μl) at 0° C. was added oxalyl chloride (61.3 μl, 0.76 mmol) followed by DMF (5.37 μl, 0.069 mmol). The reaction mixture was allowed to gradually warm to RT for 1.5 hr. After concentration under reduced pressure, the residue was taken up in DCM (2.3 mL), followed by the addition of MeOH (140 μl, 3.47 mmol). The resulting solution was stirred for 2 h, diluted with saturated NaHCO$_3$, and extracted with DCM. The combined organics were washed with brine), dried over MgSO$_4$, and concentrated. The residue was purified by flash chromatography (0-10% EtOAc/hexanes, 24 g silica column) to afford the title compound as an oil.

Step 2: Methyl 2-(3-aminobicyclo [1.1.1] pentan-1-yl) Propanoate Hydrochloride

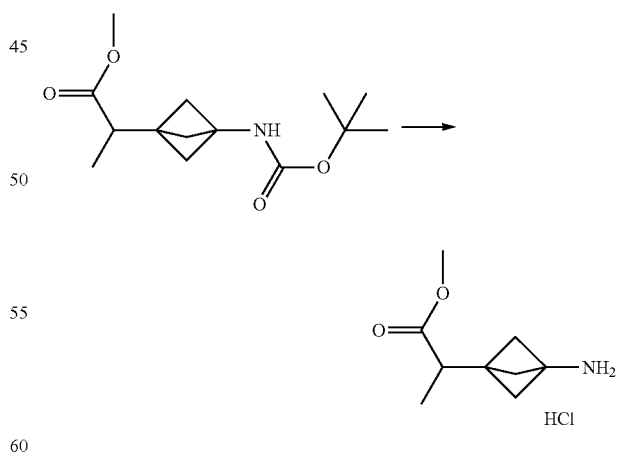

To a solution of methyl 2-(3-((tert-butoxycarbonyl) amino) bicyclo [1.1.1]pentan-1-yl) propanoate (67 mg, 0.25 mmol) was added HCl (4.0M in dioxane, 0.5 ml). The mixture was stirred at RT for 2 h, concentrated to afford the title compound as a solid, which was used for the next step directly.

Step 3: Methyl 2-(3-(3,4-dichlorobenzamido) bicyclo [1.1.1] pentan-1-yl) Propanoate

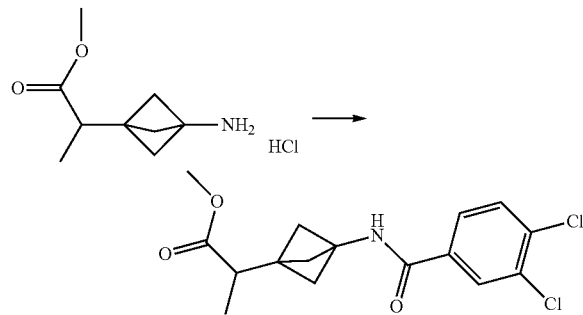

To a solution of methyl 2-(3-aminobicyclo [1.1.1] pentan-1-yl) propanoate hydrochloride (52.1 mg, 0.253 mmol) in THF (1.27 mL) was added Et$_3$N (141 µl, 1.01 mmol) and 3,4-dichlorobenzoyl chloride (80 mg, 0.38 mmol). The reaction mixture was stirred at RT for 0.5 h. The reaction mixture was diluted with sat. NaHCO$_3$, and extracted with EtOAc. The organic layer was separated, washed with brine, dried over MgSO$_4$, and concentrated. The residue was purified by flash chromatography (0-70% EtOAc/hexanes, 12 g silica column) to afford the title compound as an oil.

Step 4: 2-(3-(3,4-Dichlorobenzamido) bicyclo [1.1.1] pentan-1-yl) Propanoic Acid

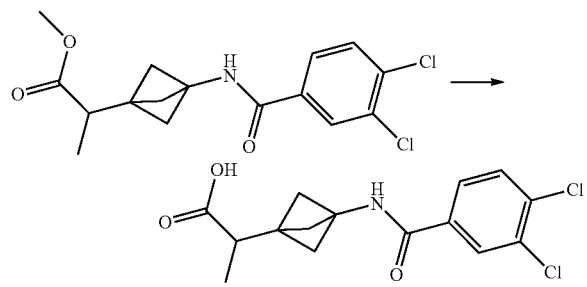

To a solution of methyl 2-(3-(3,4-dichlorobenzamido) bicyclo [1.1.1] pentan-1-yl) propanoate (70 mg, 0.205 mmol) in THF (930 µl) was added sodium hydroxide (16.4 mg, 0.41 mmol) and MeOH (93 µl). The resulting reaction mixture was stirred at RT overnight. The reaction mixture was concentrated to remove the solvent, and the residue was neutralized with 1N HCl to pH=2-3 and extracted with EA. The combined organic layers were washed with brine, dried over MgSO$_4$, concentrated to afford the title compound as a solid.

Step 5: Tert-butyl (1-(3-(3,4-dichlorobenzamido) bicyclo [1.1.1] pentan-1-yl) ethyl) carbamate

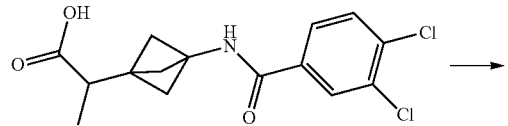

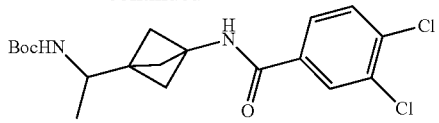

A mixture of 2-(3-(3,4-dichlorobenzamido) bicyclo [1.1.1] pentan-1-yl) propanoic acid (52 mg, 0.16 mmol), diphenyl phosphoryl azide (37.5 µl, 0.17 mmol), Et$_3$N (27 µl, 0.19 mmol) in tert —BuOH (317 µl) was refluxed at 85° C. for 3 h. The mixture was cooled down, quenched with sat.NaHCO$_3$ and extracted with ethyl acetate. The organic layer was separated, washed with brine, dried over MgSO$_4$, and concentrated. The residue was purified by flash chromatography (0-50% EtOAc/hexanes, 12 g silica column) to afford the title compound as a solid.

Step 6: 3,4-Dichloro-N-(3-(1-(4-fluorobenzamido) ethyl) bicyclo [1.1.1] pentan-1-yl) Benzamide

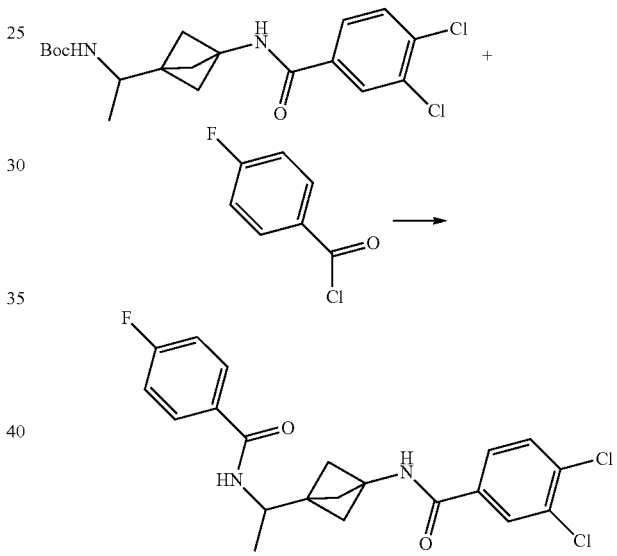

To a flask containing tert-butyl (1-(3-(3,4-dichlorobenzamido) bicyclo [1.1.1]pentan-1-yl) ethyl) carbamate (16 mg, 0.04 mmol) was added with HCl (4M in dioxane, 0.3 ml), and the reaction mixture was stirred at RT overnight. The resulting mixture was concentrated and the residue was taken up in THF (0.20 ml), followed by the addition of triethylamine (0.022 ml, 0.16 mmol) and 4-fluorobenzoyl chloride (12.7 mg, 0.08 mmol). The resulting reaction mixture was stirred at RT for 30 min, diluted sat NaHCO$_3$, and extracted with ethyl acetate. The organic layer was separated, washed with brine, dried over MgSO$_4$, and concentrated. The residue was purified by flash chromatography (0-50% 3:1 EtOAc: ethanol//hexanes, 12 g silica column) to afford the title compound as a solid.

The racemic 3,4-dichloro-N-(3-(1-(4-fluorobenzamido) ethyl)bicyclo[1.1.1]pentan-1-yl)benzamide was submitted for Chiral SFC separation (OJ-H, Condition MeOH+0.25% DMEA) to afford two separate enantiomers as solids.

Ex. 21 (peak 1): LCMS: 421.0 [M+H]$^+$; $^1$H NMR (499 MHz, DMSO-d$_6$) δ 9.12 (s, 1H), 8.18 (d, J=8.5 Hz, 1H), 8.07 (d, J=1.7 Hz, 1H), 7.92 (dd, J=8.6, 5.6 Hz, 2H), 7.81 (dd, J=8.4, 1.8 Hz, 1H), 7.74 (d, J=8.4 Hz, 1H), 7.30 (t, J=8.8 Hz, 2H), 4.27 (p, J=6.9 Hz, 1H), 1.96 (q, J=9.3 Hz, 6H), 1.14 (d, J=6.9 Hz, 3H).

Ex. 22 (peak 2): LCMS: 421.0 [M+H]⁺; ¹H NMR (499 MHz, DMSO-$d_6$) δ 9.12 (s, 1H), 8.18 (d, J=8.5 Hz, 1H), 8.07 (d, J=1.7 Hz, 1H), 7.92 (dd, J=8.6, 5.6 Hz, 2H), 7.81 (dd, J=8.4, 1.8 Hz, 1H), 7.74 (d, J=8.4 Hz, 1H), 7.30 (t, J=8.8 Hz, 2H), 4.27 (p, J=6.9 Hz, 1H), 1.96 (q, J=9.3 Hz, 6H), 1.14 (d, J=6.9 Hz, 3H).

Example 23: Benzyl (3-(1-(4-fluorobenzamido)cyclopropyl)bicyclo[1.1.1]pentan-1-yl)carbamate

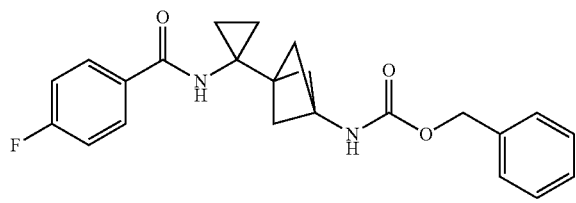

Step 1. Benzyl 3-cyanobicyclo[1.1.1]pentane-1-carboxylate

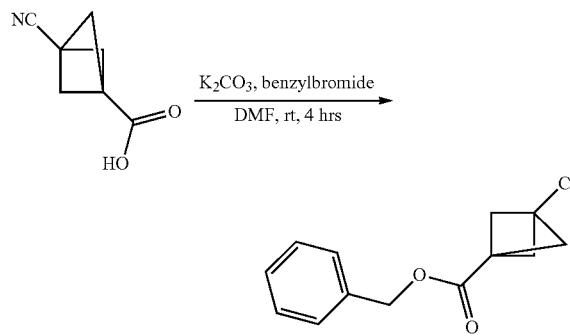

To a stirred mixture of K₂CO₃ (504 mg, 3.65 mmol) and 3-cyanobicyclo[1.1.1]pentane-1-carboxylic acid (250 mg, 1.823 mmol) in DMF (4 ml), was slowly added benzyl bromide (374 mg, 2.19 mmol). The reaction was allowed to stir at RT for 4 h, the mixture was then partitioned into water and EtOAc. The organic layer was then concentrated and purified on silica gel chromatography with 0 to 100% EtOAc in Hexane to get an oil. ¹H NMR (400 MHz, CDCl₃) δ 7.30 (m, 5H), 5.15 (s, 2H), 2.52 (s, 6H).

Step 2. Benzyl 3-(1-aminocyclopropyl)bicyclo[1.1.1]pentane-1-carboxylate

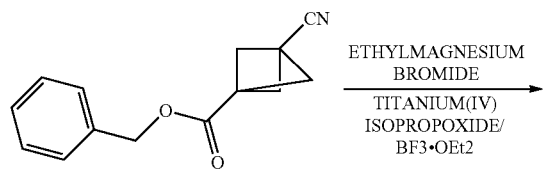

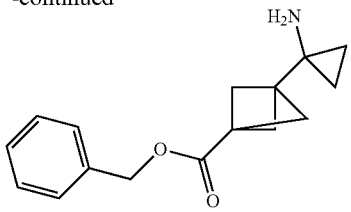

Titanium(IV)isopropoxide (2.269 ml, 7.74 mmol) is added to a solution of benzyl 3-cyanobicyclo[1.1.1]pentane-1-carboxylate (1.6 g, 7.04 mmol) in ether (25 ml). The solution is cooled down to a temperature of −78° C. and ethyl magnesium bromide (5.16 ml, 15.49 mmol) solution (3 M in ether) is slowly added. After 10 min at −78° C., the slurry is allowed to warm up to ambient temperature and stirred for 1 h. BF₃.OEt₂ (1.963 ml, 15.49 mmol) is added dropwisely and the mixture is stirred at ambient temperature for 18 h. To this mixture, 100 ml NaOH 2N is slowly added at a temperature of 0° C., extracted by 1:1 ratio mixture solvent of ether and EtOAc. The organic layer was concentrated, solid loading to 120 g normal phase ISCO, purified with 0 to 100% 3:1 EtOAc and ethanol with hexane, the product was isolated as an oil. ¹H NMR (400 MHz, MeOD) δ 8.20 (m, 5H), 5.90 (s, 2H), 1.95 (s, 6H), 0.75 (s, 4H); MS (ESI) m/z: 258.3 [M+H⁺].

Step 3. Benzyl 3-(1-(4-fluorobenzamido)cyclopropyl)bicyclo[1.1.1]pentane-1-carboxylate

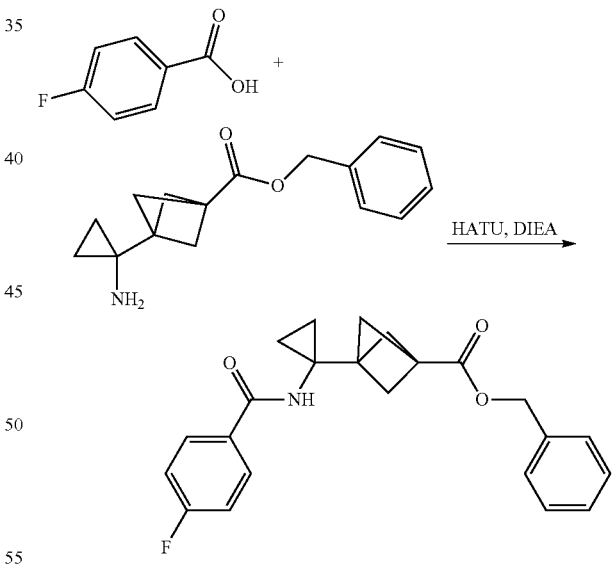

To a mixture of 4-fluorobenzoic acid (463 mg, 3.30 mmol) and HATU (1256 mg, 3.30 mmol) in DMF (5 ml) was added benzyl 3-(1-aminocyclopropyl)bicyclo[1.1.1]pentane-1-carboxylate (850 mg, 3.30 mmol) and DIEA (0.577 ml, 3.30 mmol). After 5 min, the reaction mixture was partitioned between EtOAc and water. The organic layer was concentrated, purified on silica gel chromatography with 0 to 100% EtOAc in Hexane to give the target product. ¹H NMR (400 MHz, MeOD) δ 9.55 (s, 1H), 8.72 (m, 2H), 8.20 (m, 5H), 8.10 (m, 2H), 5.90 (s, 2H), 2.65 (s, 6H), 1.5 (m, 4H); MS (ESI) m/z: 380.23 [M+H⁺]

Step 4. 3-(1-(4-Fluorobenzamido)cyclopropyl)bicyclo[1.1.1]pentane-1-carboxylic Acid

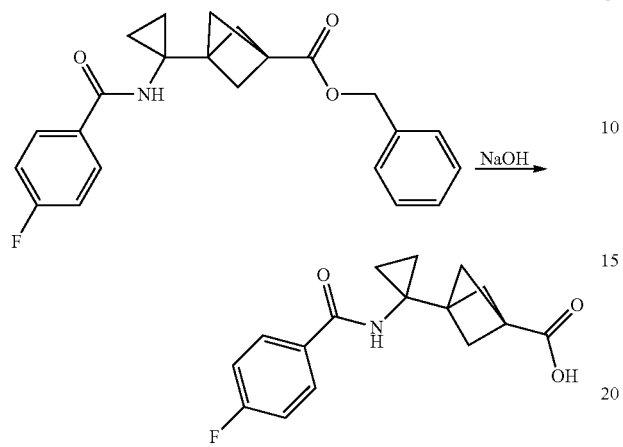

To a solution of benzyl 3-(1-(4-fluorobenzamido)cyclopropyl)bicyclo[1.1.1]pentane-1-carboxylate (640 mg, 1.687 mmol) in THF (10 ml) was added NaOH (2M, 1.687 ml, 3.37 mmol). The mixture was stirred at 45° C. for 30 min, cooled down, and THF was removed by vacuo. Water was added and the basic aqueous layer was extracted with diethyl ether to remove benzyl alcohol. The mixture was acidified with 10% HCl, extracted with EtOAc. The organic layer was concentrated, purified on 50 g reversed C18 column with 0 to 100% ACN in water with 0.05% TFA. The product was concentrated as an oil, and then lyophilized to afford the title compound as a solid. $^1$H NMR (400 MHz, MeOD) δ 8.80 (s, 1H), 7.8 (m, 2H), 7.25 (m, 2H), 1.95 (s, 6H), 0.8 (m, 4H); MS (ESI) m/z: 290.2 [M+H$^+$]

Step 5. Benzyl (3-(1-(4-fluorobenzamido)cyclopropyl)bicyclo[1.1.1]pentan-1-yl)carbamate (Ex. 23)

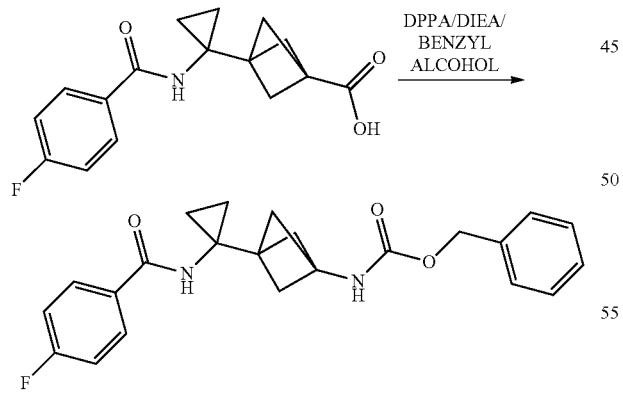

A solution of 3-(1-(4-fluorobenzamido)cyclopropyl)bicyclo[1.1.1]pentane-1-carboxylic acid (200 mg, 0.691 mmol), diphenylphosphoryl azide (0.163 ml, 0.760 mmol), benzyl alcohol (0.079 ml, 0.760 mmol) and DIEA (0.241 ml, 1.383 mmol) in THF (5 ml) was heated to reflux (67C). After 15 h, the mixture was cooled down, diluted with EtOAc and washed with 1M HCl, water, 1M NaOH, brine, dried over NaSO4, filtered, and concentrated. The resulting material was purified on silica gel chromatography with 0 to 100% EtOAc in hexane, the title compound was collected as a solid. $^1$H NMR (400 MHz, CDCl$_3$) δ 7.75 (m, 2 H), 7.3 (m, 5H), 7.15 (m, 2H), 6.25 (s, 1H), 5.15 (s, 2H), 1.95 (br s, 6H), 0.85 (m, 4H); MS (ESI) m/z: 395.28 [M+H$^+$]

Example 24: 3,4-Dichloro-N-(3-(1-(4-fluorobenzamido)cyclopropyl)bicyclo[1.1.1]pentan-1-yl)benzamide

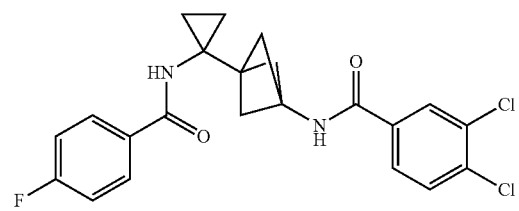

Step 1. N-(1-(3-Aminobicyclo[1.1.1]pentan-1-yl)cyclopropyl)-4-fluorobenzamide

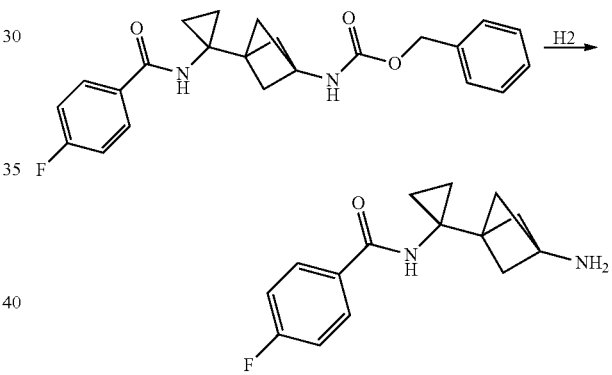

To a solution of benzyl (3-(1-(4-fluorobenzamido)cyclopropyl)bicyclo[1.1.1]pentan-1-yl)carbamate (200 mg, 0.507 mmol), Pd/C (10.79 mg, 0.101 mmol) and MeOH (10 ml) was charged with hydrogen balloon and stirred at RT for 40 min. The mixture was filtered and concentrated. The crude material was used for the next step. MS (ESI) m/z: 261.27 [M+H$^+$]

Step 2. 3,4-Dichloro-N-(3-(1-(4-fluorobenzamido)cyclopropyl)bicyclo[1.1.1]pentan-1-yl)benzamide (Ex. 24)

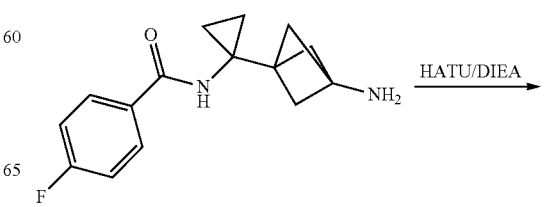

-continued

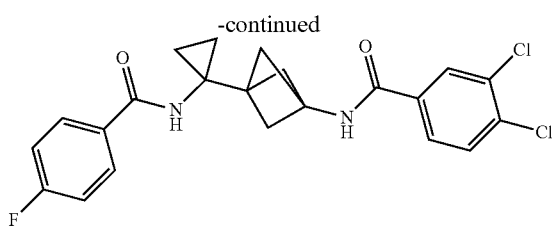

To a solution of 3,4-dichlorobenzoic acid (22.01 mg, 0.115 mmol) and HATU (65.7 mg, 0.173 mmol) in DMF (1 ml) was added N-(1-(3-aminobicyclo[1.1.1]pentan-1-yl)cyclopropyl)-4-fluorobenzamide (30 mg, 0.115 mmol) and DIEA (0.040 ml, 0.230 mmol). The reaction was completed in 5 min and purified on reversed chromatography with 0 to 100% ACN in water with 0.05% TFA. The product was isolated and lyophilized to afford the title compound as a solid. $^1$H NMR (400 MHz, CDCl$_3$) δ 7.80 (s, 1H), 7.75 (m, 2H), 7.55 (m, 1H), 7.50 (m, 1H), 7.15 (m, 2H), 6.45 (s, 1H), 6.40 (s, 1H), 2.10 (s, 6H), 0.95 (s, 4H); MS (ESI) m/z: 433.2 [M+H$^+$]

The following compounds in Table 3 were prepared using similar procedures for Example 24.

TABLE 3

| Ex. # | Structure | Chemical Name | Mass [M + H]+ |
|---|---|---|---|
| 25 | 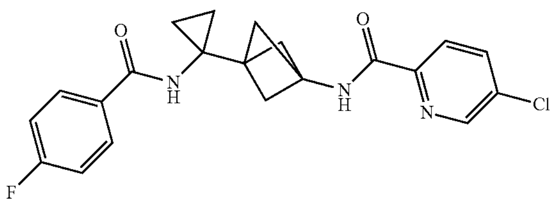 [SMILES: O=C(NC1(C23CC(NC(=O)c4ccc(Cl)cn4)(C2)C3)CC1)c1ccc(F)cc1] | 5-chloro-N-(3-(1-(4-fluorobenzamido)cyclopropyl)bicyclo[1.1.1]pentan-1-yl)picolinamide | 400.2 |
| 26 | 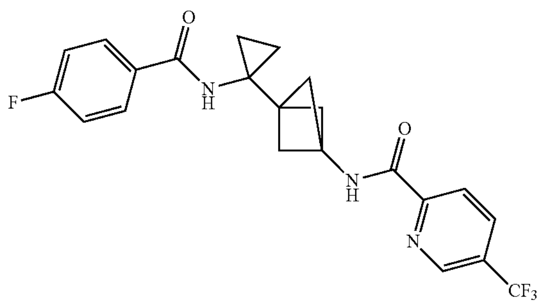 [SMILES: O=C(NC1(C23CC(NC(=O)c4ccc(C(F)(F)F)cn4)(C2)C3)CC1)c1ccc(F)cc1] | N-(3-(1-(4-fluorobenzamido)cyclopropyl)bicyclo[1.1.1]pentan-1-yl)-5-(trifluoromethyl)picolinamide | 434.22 |
| 27 | 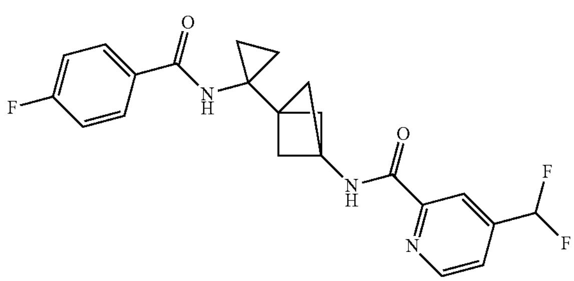 [SMILES: O=C(NC1(C23CC(NC(=O)c4cc(C(F)F)ccn4)(C2)C3)CC1)c1ccc(F)cc1] | 4-(difluoromethyl)-N-(3-(1-(4-fluorobenzamido)cyclopropyl)bicyclo[1.1.1]pentan-1-yl)picolinamide | 416.26 |
| 28 | 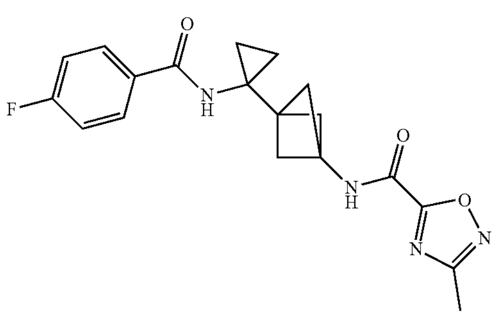 [SMILES: Cc1noc(C(=O)NC23CC(C4(NC(=O)c5ccc(F)cc5)CC4)(C2)C3)n1] | N-(3-(1-(4-fluorobenzamido)cyclopropyl)bicyclo[1.1.1]pentan-1-yl)-3-methyl-1,2,4-oxadiazole-5-carboxamide | 371.24 |

TABLE 3-continued

| Ex. # | Structure | Chemical Name | Mass [M + H]+ |
|---|---|---|---|
| 29 | 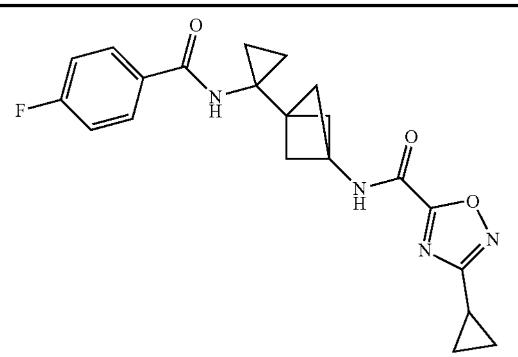 | 3-cyclopropyl-N-(3-(1-(4-fluorobenzamido)cyclopropyl)bicyclo[1.1.1]pentan-1-yl)-1,2,4-oxadiazole-5-carboxamide | 397.23 |
| 30 | 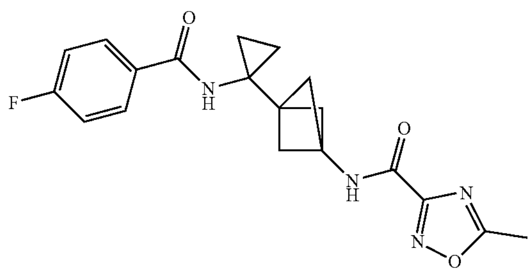 [SMILES: Cc1nc(C(=O)NC23CC(C4(NC(=O)c5ccc(F)cc5)CC4)(C2)C3)no1] | N-(3-(1-(4-fluorobenzamido)cyclopropyl)bicyclo[1.1.1]pentan-1-yl)-5-methyl-1,2,4-oxadiazole-3-carboxamide | 371.22 |

Examples 31 and 32. Tert-butyl (R)-(3-(1-((4-fluorophenyl)amino)-1-oxopropan-2-yl)bicyclo[1.1.1]pentan-1-yl)carbamate and tert-butyl (S)-(3-(1-((4-fluorophenyl)amino)-1-oxopropan-2-yl)bicyclo[1.1.1]pentan-1-yl)carbamate Ex. 31

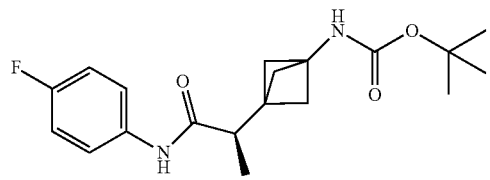

Ex. 32

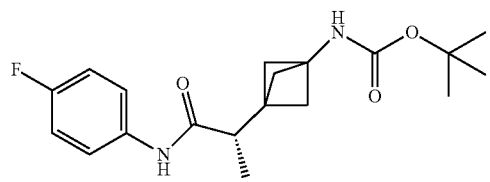

Step 1. Tert-butyl (3-(1-((4-fluorophenyl)amino)-1-oxopropan-2-yl)bicyclo[1.1.1]pentan-1-yl)carbamate

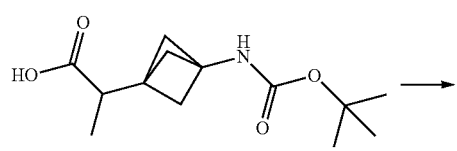

-continued

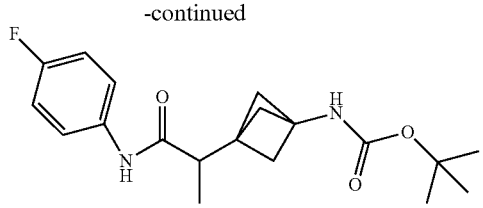

To the stirred solution of 2-(3-((tert-butoxycarbonyl)amino)bicyclo[1.1.1]pentan-1-yl)propanoic acid (12 g, 47.0 mmol) and HATU (20.55 g, 54.1 mmol) in dry DMF (100 ml) were added DIEA ((24.6 ml, 141 mmol) and 4-fluoroaniline (Aldrich) (5.80 ml, 61.1 mmol). The mixture was stirred at RT overnight. LCMS showed the desired product as the major product. The mixture was partitioned between EtOAc (200 ml) and water (100 ml). The aqueous was extracted with EtOAc for three times. Organic phases were separated, combined and derived over $Na_2SO_4$, then filtered and concentrated. The crude residue was purified by Teledyne Isco system, using 120 g silica combiflash gold column and 0-100% EtOAc in hexane as eluting solvent to give the desired product as a solid. LC-Mass (M+H) calc.=349.18; found desired product M+H=349; M+H−56 (−tBu)=293.22.

Step 2. Tert-butyl (R)-(3-(1-((4-fluorophenyl)amino)-1-oxopropan-2-yl)bicyclo[1.1.1]pentan-1-yl)carbamate (Ex. 31) and tert-butyl (S)-(3-(1-((4-fluorophenyl)amino)-1-oxopropan-2-yl)bicyclo[1.1.1]pentan-1-yl)carbamate (Ex. 32)

The racemic compound from step 1 was resolved by chiral SFC using an OJ-H, 50×250 mm column to give both enantiomers as solids. The absolute stereochemistry of each enantiomer was independently determined by Vibrational Circular Dichroism.

The absolute configuration of peak 1 was assigned to be (R) using Vibrational Circular Dichroism (VCD) spectroscopy. Analysis was done comparing experimental data to the calculated VCD and IR spectra of the (R) configuration. The experimental VCD spectrum of peak 1 matched with the calculated (R) spectrum over the region from 1000-1850 cm$^{-1}$.

The absolute configuration of peak 2 was assigned to be (S) using Vibrational Circular Dichroism (VCD) spectroscopy. Analysis was done comparing experimental data to the calculated VCD and IR spectra of the (R) configuration. The experimental VCD spectrum of peak 2 matched with the mirror image of the calculated (R) spectrum over the region from 1000-1850 cm$^{-1}$.

Ex. 31 (Peak 1): LC-Mass (M+H) calc.=349.18; found isomer 1: M+H=349; M+H−56 (−tBu)=293.21.

Ex. 32 (Peak 2): LC-Mass (M+H) calc.=349.18; found isomer 2: M+H=349; M+H−56 (−tBu)=293.21.

Examples 33 and 34. (R)-6-Chloro-N-(3-(1-((4-fluorophenyl)amino)-1-oxopropan-2-yl)bicyclo[1.1.1]pentan-1-yl)picolinamide and (S)-6-chloro-N-(3-(1-((4-fluorophenyl)amino)-1-oxopropan-2-yl)bicyclo[1.1.1]pentan-1-yl)picolinamide

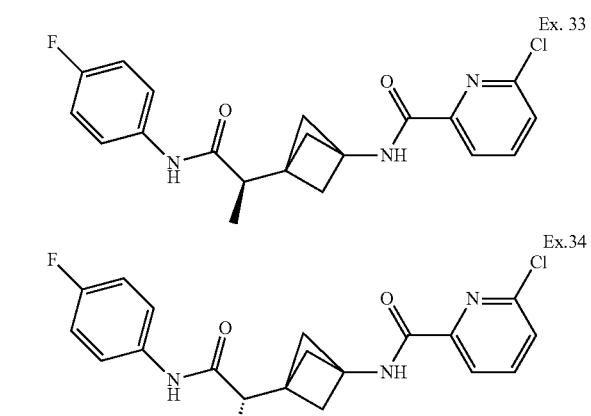

Step 1A. (R)-2-(3-Aminobicyclo[1.1.1]pentan-1-yl)-N-(4-fluorophenyl)propanamide hydrochloride

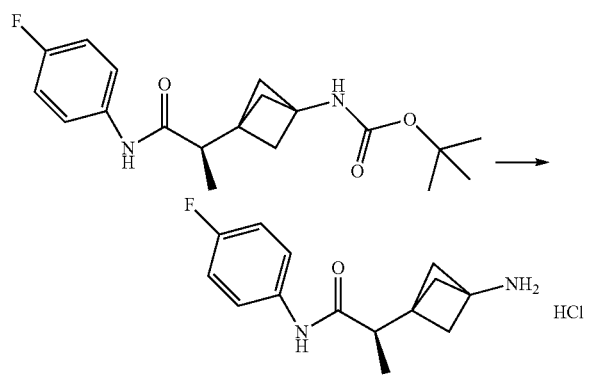

Tert-butyl (R)-(3-(1-((4-fluorophenyl)amino)-1-oxopropan-2-yl)bicyclo[1.1.1]pentan-1-yl)carbamate (2150 mg, 6.17 mmol) was dissolved in HCl (4.0 M in dioxane) (38.2 ml, 153 mmol). The mixture was stirred at RT for about 2 h. LCMS showed reaction completed, and the desired product as the major product. The mixture was concentrated in vacuo to give the title compound as a solid. LC-MS: (M+H) calc.=249.13; found: M+H=249.28.

Step 1B. (S)-2-(3-Aminobicyclo[1.1.1]pentan-1-yl)-N-(4-fluorophenyl)propanamide hydrochloride

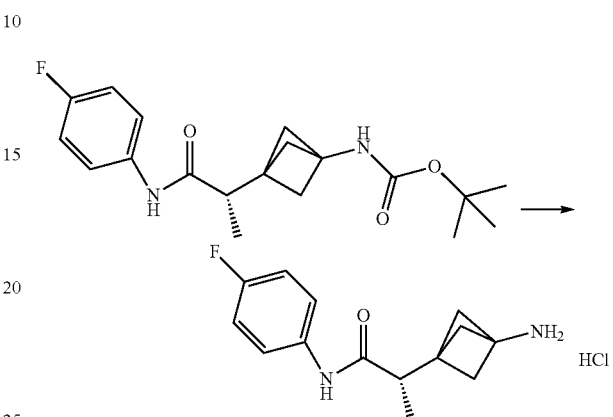

Tert-butyl (S)-(3-(1-((4-fluorophenyl)amino)-1-oxopropan-2-yl)bicyclo[1.1.1]pentan-1-yl)carbamate (2130 mg, 6.11 mmol) was dissolved in HCl (4.0 M in dioxane) (38.2 ml, 153 mmol). The mixture was stirred at RT for about 2 h. LCMS showed the reaction was complete, and the desired product as the major product. The mixture was concentrated in vacuo to afford the title compound as a solid. LC-MS (M+H) calc.=249.13; found: M+H=249.13.

Step 2A. (R)-6-Chloro-N-(3-(1-((4-fluorophenyl)amino)-1-oxopropan-2-yl)bicyclo[1.1.1]pentan-1-yl)picolinamide (Ex. 33)

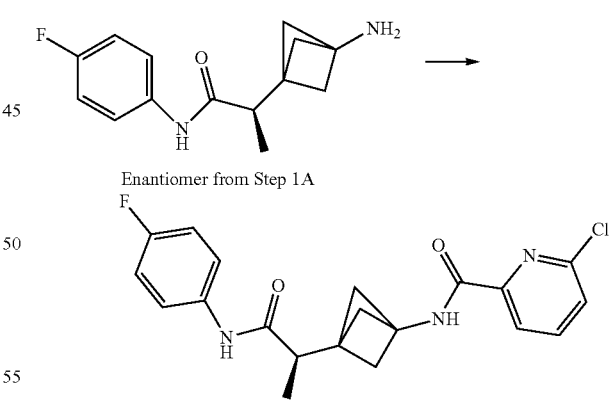

To the stirred solution of 6-chloropicolinic acid (20.75 mg, 0.132 mmol), HATU (Aldrich) (44.1 mg, 0.116 mmol) in DMF (1054 μl) were added DIEA (73.6 μl, 0.421 mmol) and (R)-2-(3-aminobicyclo[1.1.1]pentan-1-yl)-N-(4-fluorophenyl)propanamide hydrochloride (from Step 1A, 30 mg, 0.105 mmol) The mixture was stirred at RT for 2 h. LC-MS showed the desired product as the major product.

The mixture was diluted with DMSO (~0.5 ml) and purified by mass-directed reverse HPLC purification and using the following conditions to afford the title compound as a solid after lyophilization (32 mg): Reverse HPLC on a 19×100 mm, Waters CSH C18 column, 5µ particle size, flow rate 25 ml/min, linear gradient, 35% ACN/H$_2$O to 70% ACN/H$_2$O, buffering with 0.16% TFA, total run time 9 mins.

LC-Mass calc. (M+H)=388.11; found: M+H=388.25; 1HNMR (CD3OD, 500 mHz): δ 8.01 (d, J=7.5 Hz, 1H), 7.96 (dd, J=10 Hz, 5 Hz, 1H), 7.61 (d, J=10 Hz, 1H), 7.57-7.54 (m, 2H), 7.06 (dd, J=10 Hz, 5 Hz, 2H), 2.78 (q, J=5.0 Hz, 1H), 2.14 (dd, J=10 Hz, 5 Hz, 6H), 1.14 (d, J=5.0 Hz, 3H).

Step 2B. (S)-6-Chloro-N-(3-(1-(((4-fluorophenyl)amino)-1-oxopropan-2-yl)bicyclo[1.1.1]pentan-1-yl)picolinamide (Ex. 34)

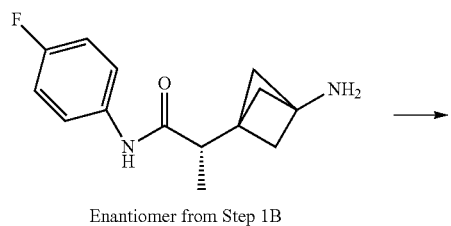

Enantiomer from Step 1B

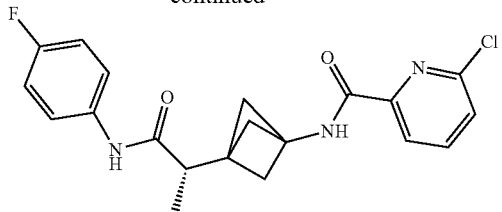

To the stirred solution of 6-chloropicolinic acid (20.75 mg, 0.132 mmol), HATU (Aldrich) (44.1 mg, 0.116 mmol) in DMF (1054 µl) were added DIEA (73.6 µl, 0.421 mmol) and (S)-2-(3-aminobicyclo[1.1.1]pentan-1-yl)-N-(4-fluorophenyl)propanamide hydrochloride (from Step 1B, 30 mg, 0.105 mmol). The mixture was stirred at RT for 2 h. LC-MS showed the desired product as the major product.

The mixture was diluted with DMSO (~0.5 ml) and purified by mass-directed reverse HPLC purification and using the following conditions to afford the title compound as a solid after lyophilization (28 mg): Reverse HPLC on a 19×100 mm, Waters CSH C18 column, 5µ particle size, flow rate 25 ml/min, linear gradient, 35% ACN/H$_2$O to 70% ACN/H$_2$O, buffering with 0.16% TFA, total run time 9 mins.

LC-Mass calc. (M+H)=388.11; found: M+H=388.24; 1HNMR (CD3OD, 500 mHz): δ 8.01 (d, J=7.5 Hz, 1H), 7.96 (dd, J=10 Hz, 5 Hz, 1H), 7.61 (d, J=10 Hz, 1H), 7.57-7.54 (m, 2H), 7.06 (dd, J=10 Hz, 5 Hz, 2H), 2.78 (q, J=5.0 Hz, 1H), 2.14 (dd, J=10 Hz, 5 Hz, 6H), 1.14 (d, J=5.0 Hz, 3H).

The following compounds in Table 4 were prepared using similar procedures for Examples 33 and 34.

TABLE 4

| Ex. # | Structure | Chemical Name | Mass [M + H]+ |
|---|---|---|---|
| 35 | 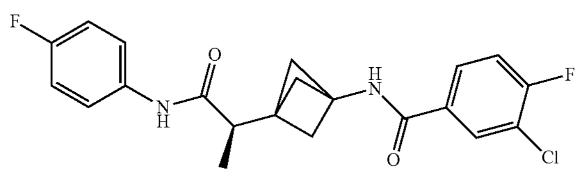 | 3-chloro-4-fluoro-N-[3-[(1R)-2-(4-fluoroanilino)-1-methyl-2-oxo-ethyl]-1-bicyclo[1.1.1]pentanyl]benzamide | 405 |
| 36 | 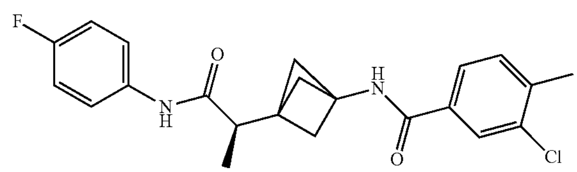 [SMILES: Cc1ccc(C(=O)NC23CC([C@@H](C)C(=O)Nc4ccc(F)cc4)(C2)C3)cc1Cl] | 3-chloro-N-[3-[(1R)-2-(4-fluoroanilino)-1-methyl-2-oxo-ethyl]-1-bicyclo[1.1.1]pentanyl]-4-methyl-benzamide | 401 |
| 37 | 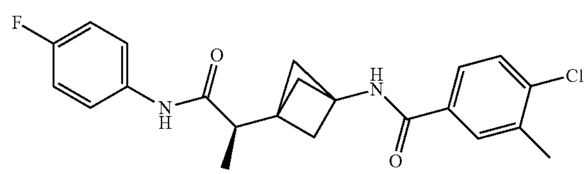 [SMILES: Cc1cc(C(=O)NC23CC([C@@H](C)C(=O)Nc4ccc(F)cc4)(C2)C3)ccc1Cl] | 4-chloro-N-[3-[(1R)-2-(4-fluoroanilino)-1-methyl-2-oxo-ethyl]-1-bicyclo[1.1.1]pentanyl]-3-methyl-benzamide | 401 |
| 38 | 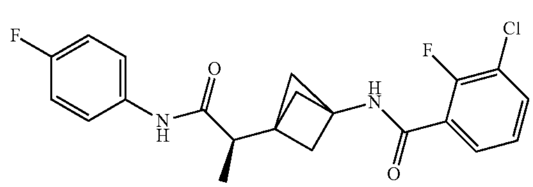 [SMILES: C[C@@H](C(=O)Nc1ccc(F)cc1)C12CC(NC(=O)c3cccc(Cl)c3F)(C1)C2] | 3-chloro-2-fluoro-N-[3-[(1R)-2-(4-fluoroanilino)-1-methyl-2-oxo-ethyl]-1-bicyclo[1.1.1]pentanyl]benzamide | 405 |

TABLE 4-continued

| Ex. # | Structure | Chemical Name | Mass [M + H]+ |
|---|---|---|---|
| 39 | 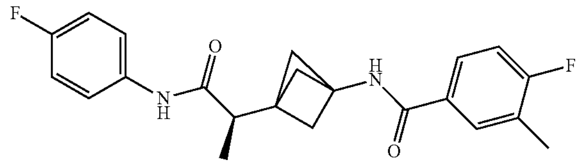 [SMILES: Cc1cc(C(=O)NC23CC([C@@H](C)C(=O)Nc4ccc(F)cc4)(C2)C3)ccc1F] | 4-fluoro-N-[3-[(1R)-2-(4-fluoroanilino)-1-methyl-2-oxo-ethyl]-1-bicyclo[1.1.1]pentanyl]-3-methyl-benzamide | 385 |
| 40 | 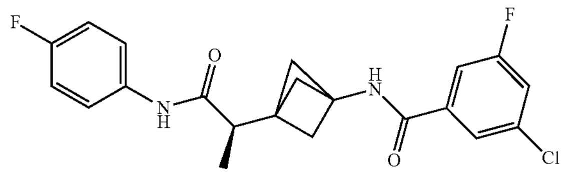 [SMILES: C[C@@H](C(=O)Nc1ccc(F)cc1)C12CC(NC(=O)c3cc(F)cc(Cl)c3)(C1)C2] | 3-chloro-5-fluoro-N-[3-[(1R)-2-(4-fluoroanilino)-1-methyl-2-oxo-ethyl]-1-bicyclo[1.1.1]pentanyl]benzamide | 405 |
| 41 | 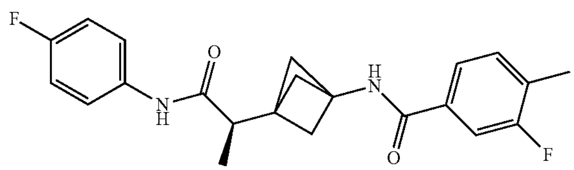 | 3-fluoro-N-[3-[(1R)-2-(4-fluoroanilino)-1-methyl-2-oxo-ethyl]-1-bicyclo[1.1.1]pentanyl]-4-methyl-benzamide | 385 |
| 42 | 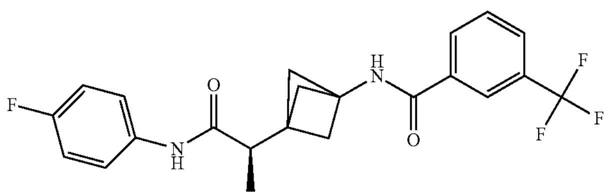 [SMILES: C[C@@H](C(=O)Nc1ccc(F)cc1)C12CC(NC(=O)c3cccc(C(F)(F)F)c3)(C1)C2] | N-[3-[(1R)-2-(4-fluoroanilino)-1-methyl-2-oxo-ethyl]-1-bicyclo[1.1.1]pentanyl]-3-(trifluoromethyl)benzamide | 421 |
| 43 | 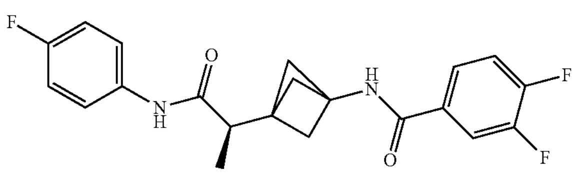 | 3,4-difluoro-N-[3-[(1R)-2-(4-fluoroanilino)-1-methyl-2-oxo-ethyl]-1-bicyclo[1.1.1]pentanyl]benzamide | 389 |
| 44 | 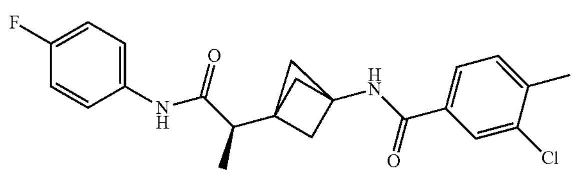 [SMILES: Cc1ccc(C(=O)NC23CC([C@@H](C)C(=O)Nc4ccc(F)cc4)(C2)C3)cc1Cl] | 3-chloro-N-[3-[(1R)-2-(4-fluoroanilino)-1-methyl-2-oxo-ethyl]-1-bicyclo[1.1.1]pentanyl]-4-methyl-benzamide | 401 |
| 45 | 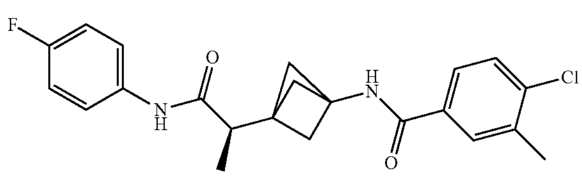 [SMILES: Cc1cc(C(=O)NC23CC([C@@H](C)C(=O)Nc4ccc(F)cc4)(C2)C3)ccc1Cl] | 4-chloro-N-[3-[(1R)-2-(4-fluoroanilino)-1-methyl-2-oxo-ethyl]-1-bicyclo[1.1.1]pentanyl]-3-methyl-benzamide | 401 |
| 46 | 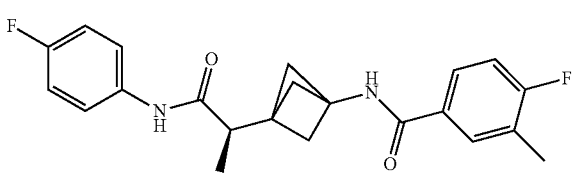 | 4-fluoro-N-[3-[(1R)-2-(4-fluoroanilino)-1-methyl-2-oxo-ethyl]-1-bicyclo[1.1.1]pentanyl]-3-methyl-benzamide | 385 |
| 47 | 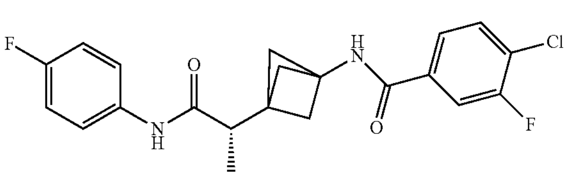 [SMILES: C[C@H](C(=O)Nc1ccc(F)cc1)C12CC(NC(=O)c3ccc(Cl)c(F)c3)(C1)C2] | 4-chloro-3-fluoro-N-[3-[(1S)-2-(4-fluoroanilino)-1-methyl-2-oxo-ethyl]-1-bicyclo[1.1.1]pentanyl]benzamide | 405 |

TABLE 4-continued

| Ex. # | Structure | Chemical Name | Mass [M + H]+ |
|---|---|---|---|
| 48 | 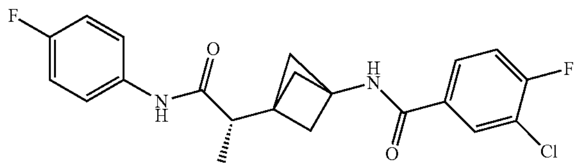 [SMILES: C[C@H](C(=O)Nc1ccc(F)cc1)C12CC(NC(=O)c3ccc(F)c(Cl)c3)(C1)C2] | 3-chloro-4-fluoro-N-[3-[(1S)-2-(4-fluoroanilino)-1-methyl-2-oxo-ethyl]-1-bicyclo[1.1.1]pentanyl]benzamide | 405 |
| 49 | 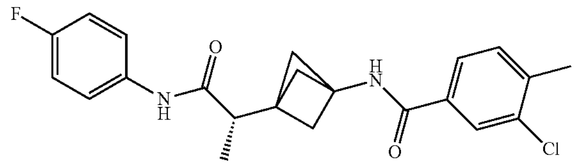 [SMILES: Cc1ccc(C(=O)NC23CC([C@H](C)C(=O)Nc4ccc(F)cc4)(C2)C3)cc1Cl] | 3-chloro-N-[3-[(1S)-2-(4-fluoroanilino)-1-methyl-2-oxo-ethyl]-1-bicyclo[1.1.1]pentanyl]-4-methyl-benzamide | 401 |
| 50 | 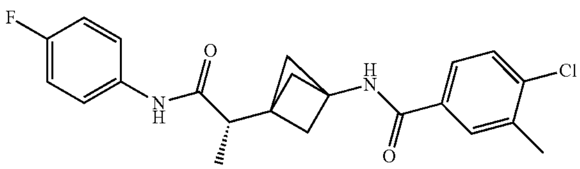 [SMILES: Cc1cc(C(=O)NC23CC([C@H](C)C(=O)Nc4ccc(F)cc4)(C2)C3)ccc1Cl] | 4-chloro-N-[3-[(1S)-2-(4-fluoroanilino)-1-methyl-2-oxo-ethyl]-1-bicyclo[1.1.1]pentanyl]-3-methyl-benzamide | 401 |
| 51 | 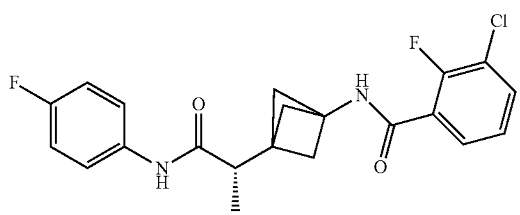 [SMILES: C[C@H](C(=O)Nc1ccc(F)cc1)C12CC(NC(=O)c3cccc(Cl)c3F)(C1)C2] | 3-chloro-2-fluoro-N-[3-[(1S)-2-(4-fluoroanilino)-1-methyl-2-oxo-ethyl]-1-bicyclo[1.1.1]pentanyl]benzamide | 405 |
| 52 | 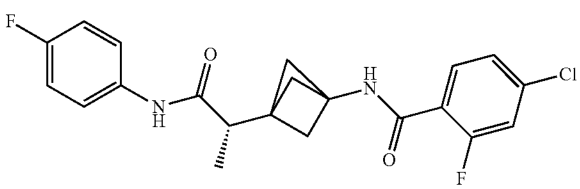 [SMILES: C[C@H](C(=O)Nc1ccc(F)cc1)C12CC(NC(=O)c3ccc(Cl)cc3F)(C1)C2] | 4-chloro-2-fluoro-N-[3-[(1S)-2-(4-fluoroanilino)-1-methyl-2-oxo-ethyl]-1-bicyclo[1.1.1]pentanyl]benzamide | 405 |
| 53 | 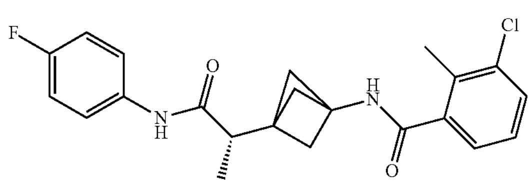 [SMILES: Cc1c(Cl)cccc1C(=O)NC12CC([C@H](C)C(=O)Nc3ccc(F)cc3)(C1)C2] | 3-chloro-N-[3-[(1S)-2-(4-fluoroanilino)-1-methyl-2-oxo-ethyl]-1-bicyclo[1.1.1]pentanyl]-2-methyl-benzamide | 401 |
| 54 | 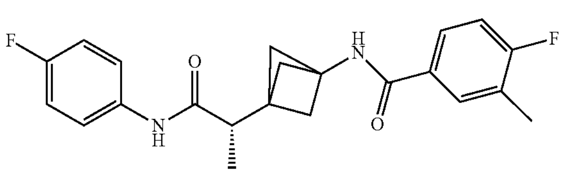 [SMILES: Cc1cc(C(=O)NC23CC([C@H](C)C(=O)Nc4ccc(F)cc4)(C2)C3)ccc1F] | 4-fluoro-N-[3-[(1S)-2-(4-fluoroanilino)-1-methyl-2-oxo-ethyl]-1-bicyclo[1.1.1]pentanyl]-3-methyl-benzamide | 385 |
| 55 | 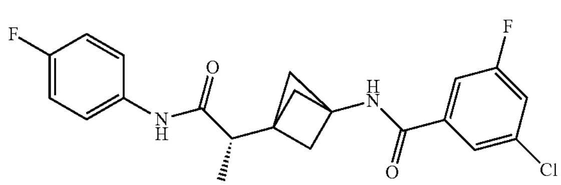 [SMILES: C[C@H](C(=O)Nc1ccc(F)cc1)C12CC(NC(=O)c3cc(F)cc(Cl)c3)(C1)C2] | 3-chloro-5-fluoro-N-[3-[(1S)-2-(4-fluoroanilino)-1-methyl-2-oxo-ethyl]-1-bicyclo[1.1.1]pentanyl]benzamide | 405 |

TABLE 4-continued

| Ex. # | Structure | Chemical Name | Mass [M + H]+ |
|---|---|---|---|
| 56 | 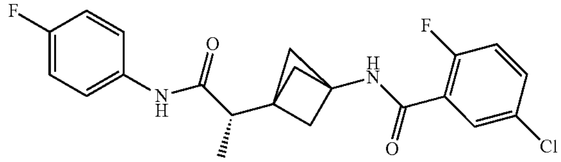 [SMILES: C[C@H](C(=O)Nc1ccc(F)cc1)C12CC(NC(=O)c3cc(Cl)ccc3F)(C1)C2] | 5-chloro-2-fluoro-N-[3-[(1S)-2-(4-fluoroanilino)-1-methyl-2-oxo-ethyl]-1-bicyclo[1.1.1]pentanyl]benzamide | 405 |
| 57 | 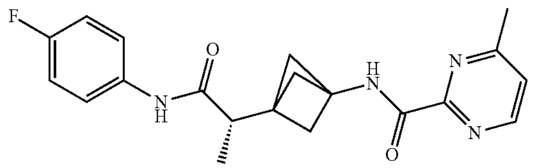 [SMILES: Cc1ccnc(C(=O)NC23CC([C@H](C)C(=O)Nc4ccc(F)cc4)(C2)C3)n1] | N-[3-[(1S)-2-(4-fluoroanilino)-1-methyl-2-oxo-ethyl]-1-bicyclo[1.1.1]pentanyl]-4-methyl-pyrimidin-1-ium-2-carboxamide | 369 |
| 58 | 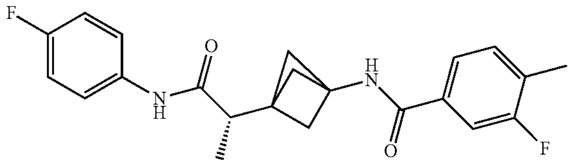 | 3-fluoro-N-[3-[(1S)-2-(4-fluoroanilino)-1-methyl-2-oxo-ethyl]-1-bicyclo[1.1.1]pentanyl]-4-methyl-benzamide | 385 |
| 59 | 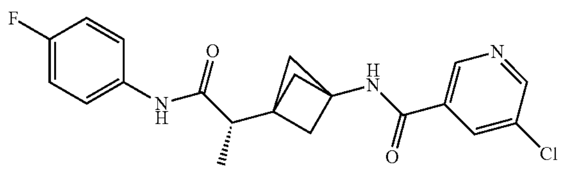 [SMILES: C[C@H](C(=O)Nc1ccc(F)cc1)C12CC(NC(=O)c3cncc(Cl)c3)(C1)C2] | 5-chloro-N-[3-[(1S)-2-(4-fluoroanilino)-1-methyl-2-oxo-ethyl]-1-bicyclo[1.1.1]pentanyl]pyridin-1-ium-3-carboxamide | 388 |
| 60 | 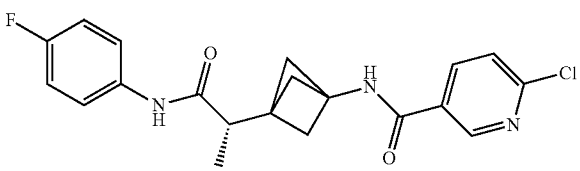 [SMILES: C[C@H](C(=O)Nc1ccc(F)cc1)C12CC(NC(=O)c3ccc(Cl)nc3)(C1)C2] | 6-chloro-N-[3-[(1S)-2-(4-fluoroanilino)-1-methyl-2-oxo-ethyl]-1-bicyclo[1.1.1]pentanyl]pyridin-1-ium-3-carboxamide | 388 |
| 61 | 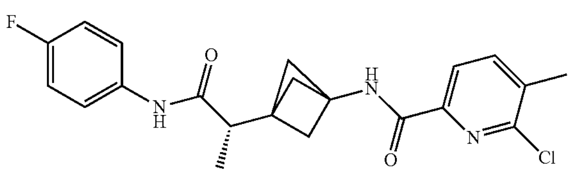 [SMILES: Cc1ccc(C(=O)NC23CC([C@H](C)C(=O)Nc4ccc(F)cc4)(C2)C3)nc1Cl] | 6-chloro-N-[3-[(1S)-2-(4-fluoroanilino)-1-methyl-2-oxo-ethyl]-1-bicyclo[1.1.1]pentanyl]-5-methyl-pyridin-1-ium-2-carboxamide | 402 |
| 62 | 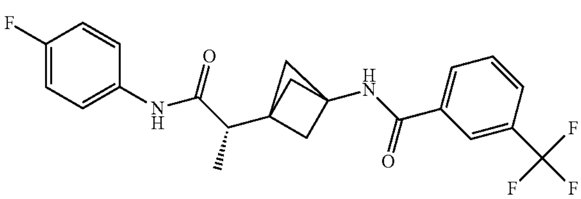 [SMILES: C[C@H](C(=O)Nc1ccc(F)cc1)C12CC(NC(=O)c3cccc(C(F)(F)F)c3)(C1)C2] | N-[3-[(1S)-2-(4-fluoroanilino)-1-methyl-2-oxo-ethyl]-1-bicyclo[1.1.1]pentanyl]-3-(trifluoromethyl)benzamide | 421 |
| 63 | 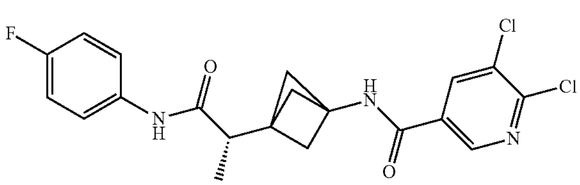 [SMILES: C[C@H](C(=O)Nc1ccc(F)cc1)C12CC(NC(=O)c3cnc(Cl)c(Cl)c3)(C1)C2] | 5,6-dichloro-N-[3-[(1S)-2-(4-fluoroanilino)-1-methyl-2-oxo-ethyl]-1-bicyclo[1.1.1]pentanyl]pyridin-1-ium-3-carboxamide | 422 |
| 64 | 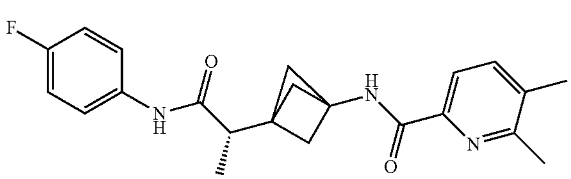 [SMILES: Cc1ccc(C(=O)NC23CC([C@H](C)C(=O)Nc4ccc(F)cc4)(C2)C3)nc1C] | N-[3-[(1S)-2-(4-fluoroanilino)-1-methyl-2-oxo-ethyl]-1-bicyclo[1.1.1]pentanyl]-5,6-dimethyl-pyridin-1-ium-2-carboxamide | 382 |

TABLE 4-continued

| Ex. # | Structure | Chemical Name | Mass [M + H]+ |
|---|---|---|---|
| 65 | 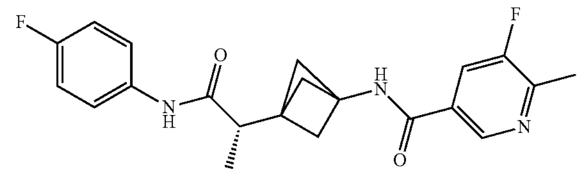 [SMILES: Cc1ncc(C(=O)NC23CC([C@H](C)C(=O)Nc4ccc(F)cc4)(C2)C3)cc1F] | 5-fluoro-N-[3-[(1S)-2-(4-fluoroanilino)-1-methyl-2-oxo-ethyl]-1-bicyclo[1.1.1]pentanyl]-6-methyl-pyridin-1-ium-3-carboxamide | 386 |
| 66 | 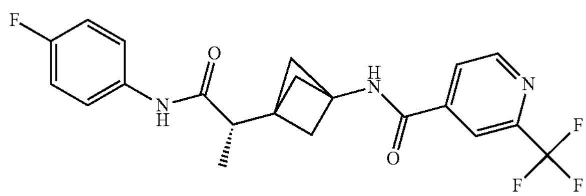 [SMILES: C[C@H](C(=O)Nc1ccc(F)cc1)C12CC(NC(=O)c3ccnc(C(F)(F)F)c3)(C1)C2] | N-[3-[(1S)-2-(4-fluoroanilino)-1-methyl-2-oxo-ethyl]-1-bicyclo[1.1.1]pentanyl]-2-(trifluoromethyl)pyridin-1-ium-4-carboxamide | 422 |
| 67 | 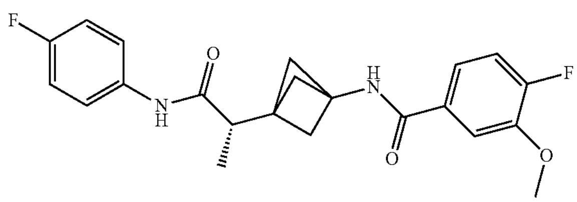 [SMILES: COc1cc(C(=O)NC23CC([C@H](C)C(=O)Nc4ccc(F)cc4)(C2)C3)ccc1F] | 4-fluoro-N-[3-[(1S)-2-(4-fluoroanilino)-1-methyl-2-oxo-ethyl]-1-bicyclo[1.1.1]pentanyl]-3-methoxy-benzamide | 401 |
| 68 | 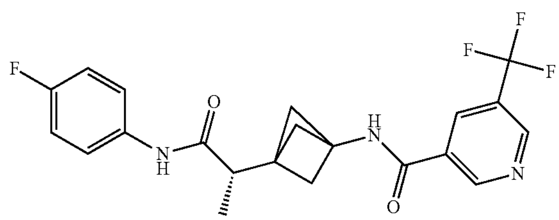 [SMILES: C[C@H](C(=O)Nc1ccc(F)cc1)C12CC(NC(=O)c3cncc(C(F)(F)F)c3)(C1)C2] | N-[3-[(1S)-2-(4-fluoroanilino)-1-methyl-2-oxo-ethyl]-1-bicyclo[1.1.1]pentanyl]-5-(trifluoromethyl)pyridin-1-ium-3-carboxamide | 422 |

Example 69. (S)-3,4-Difluoro-N-(3-(1-((4-fluorophenyl)amino)-1-oxopropan-2-yl)bicyclo[1.1.1]pentan-1-yl)benzamide

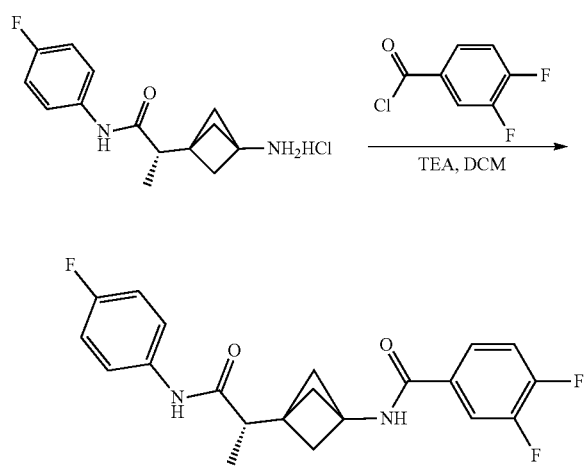

To the stirred solution of (S)-2-(3-aminobicyclo[1.1.1] pentan-1-yl)-N-(4-fluorophenyl)propanamide, HCl (1200 mg, 4.21 mmol) in $CH_2Cl_2$ (42.1 ml) were added TEA (1762 μl, 12.64 mmol) and 3,4-difluorobenzoyl chloride (691 μl, 5.48 mmol) at 0° C. The mixture was stirred at RT overnight. LCMS check showed desired product as the major product. The crude mixture was purified in different batches. About 0.42 mmol crude (~4.5 ml/45 ml crude) mixture was concentrated in vacuo and re-dissolved in DMSO and purified by mass-directed HPLC purification using the following condition (Reverse HPLC on a 19×100 mm, Waters CSH C18 column, 5μ particle size, flow rate 25 ml/min, linear gradient, 3500 ACN/$H_2O$ to 7000 ACN/$H_2O$, total run time 12 min, buffering with 0.16% TFA) to afford the title compound as a solid after Genevac drying, followed by lyophilization. LC-Mass calc. (M+H)=389.14; found: M+H=389.12. $^1$HNMR ($CD_3OD$, 500 mHz): δ 7.75-7.71 (in, 1H); 7.67-7.64 (in, 1H); 7.56 (dd, J=9.2 Hz; 4.8 Hz, 2H); 7.35 (q, J=8.5 Hz, 1H); 7.06 (t, J=8.8 Hz, 2H); 2.78 (q, J=7.2 Hz, 1H), 2.14 (m, 6H), 1.18 (d, J=6.9 Hz, 3H).

The following compounds in Table 5 were prepared using similar procedures for Examples 33 and 34.

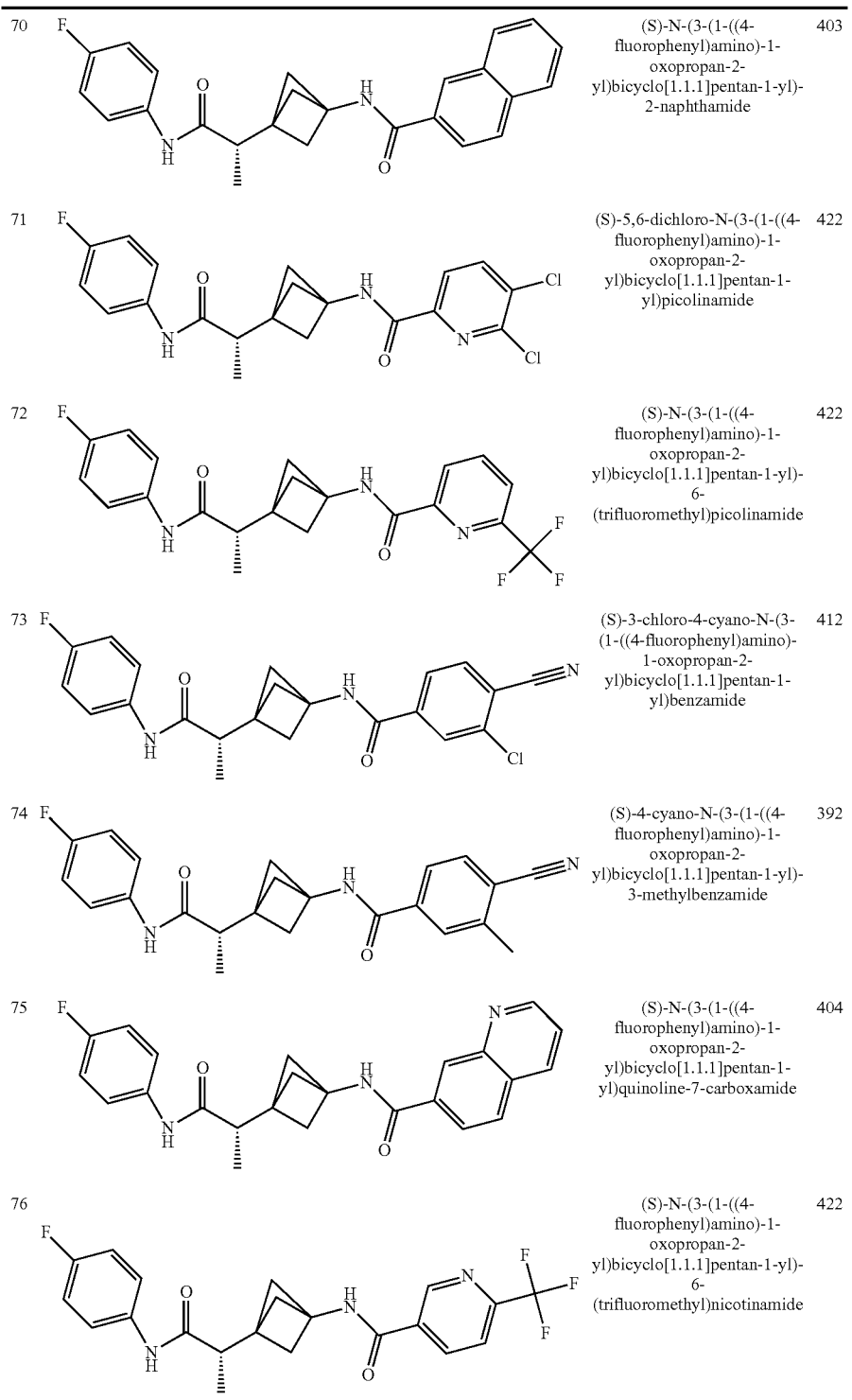

The following compounds in Table 6 were prepared using a general procedure as described below.

To the stirred solution of(S)-2-(3-aminobicyclo[.1.1]pentan-1-yl)-N-(4-fluorophenyl)propanamide, HCl (30 mg, 0.105 mmol), DIeA (Aldrich) (92 μl, 0.527 mmol) and DMAP (Aldrich) (2.57 mg, 0.021 mmol) in DMF (1200 μl) was added starting material chloroformate monomer (0.211 mmol) at RT. The mixture was stirred at RT overnight. LC-Mass showed that desired products were obtained. The mixture was filtered and purified by mass-directed reverse HPLC purification.

The following representative separation condition was used: XBridge C18, 5 um, 19×100 mm; 350%-70% acetonitrile-water (with 0.1% NH₄OH buffer) as mobile phase, total run time 12 min. The final purified compounds were Genevac dried and confirmed by LCMS and 1HNMR.

TABLE 6

| Ex. # | Structure | Chloroformate monomer | Chemical Name | Mass [M + H]+ |
|---|---|---|---|---|
| 77 | 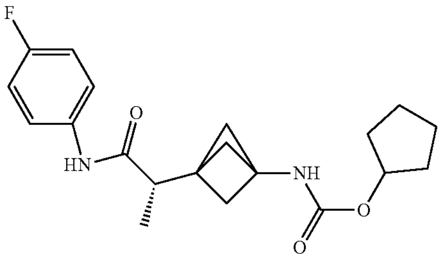 [SMILES: C[C@H](C(=O)Nc1ccc(F)cc1)C12CC(NC(=O)OC3CCCC3)(C1)C2] | | cyclopentyl (S)-(3-(1-((4-fluorophenyl)amino)-1-oxopropan-2-yl)bicyclo[1.1.1]pentan-1-yl)carbamate | 360.88 |
| 78 | 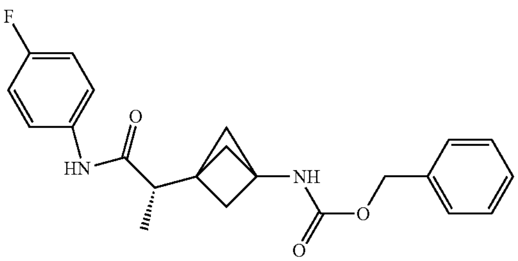 [SMILES: C[C@H](C(=O)Nc1ccc(F)cc1)C12CC(NC(=O)OCc3ccccc3)(C1)C2] | | benzyl (S)-(3-(1-((4-fluorophenyl)amino)-1-oxopropan-2-yl)bicyclo[1.1.1]pentan-1-yl)carbamate | 382.89 |
| 79 | 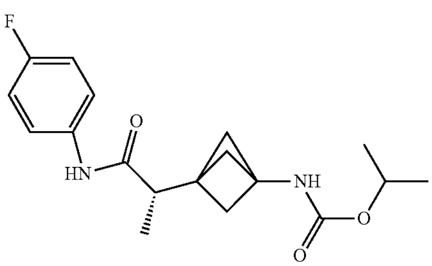 [SMILES: CC(C)OC(=O)NC12CC([C@H](C)C(=O)Nc3ccc(F)cc3)(C1)C2] | | isopropyl (S)-(3-(1-((4-fluorophenyl)amino)-1-oxopropan-2-yl)bicyclo[1.1.1]pentan-1-yl)carbamate | 334.86 |
| 80 | 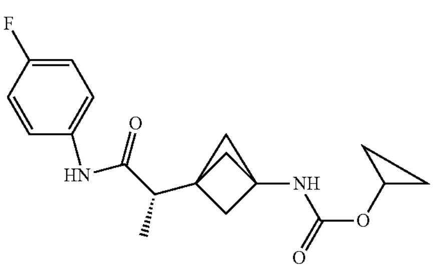 [SMILES: C[C@H](C(=O)Nc1ccc(F)cc1)C12CC(NC(=O)OC3CC3)(C1)C2] | | cyclopropyl (S)-(3-(1-((4-fluorophenyl)amino)-1-oxopropan-2-yl)bicyclo[1.1.1]pentan-1-yl)carbamate | 332.88 |

The following compounds in Table 7 were prepared using a general procedure as described below.

To the stirred solution of(S)-2-(3-aminobicyclo[1.1.1]pentan-1-yl)-N-(4-fluorophenyl)propanamide, HCl (32 mg, 0.112 mmol), DIEA (58.9 µl, 0.337 mmol) in DMF (1100 µl) was added isocyanate monomer (0.160 mmol). The mixture was stirred at RT overnight. LC-Mass showed the desired product as the main product. The mixture was filtered and purified by mass directed reverse HPLC purification. The final purified compounds were Genevac dried, and checked by LCMS and 1HNMR.

The following representative separation condition was used: Reverse HPLC on a 19×100 mm, Waters CSH C18 column, 5µ particle size, flow rate 25 ml/min, linear gradient, 35% ACN/H$_2$O to 700% ACN/H$_2$O, buffering with 0.16% TFA; total run time 12 mins.

TABLE 7

| Ex. # | Structure | Isocyanate monomer | Chemical Name | Mass [M + H]+ |
|---|---|---|---|---|
| 81 | 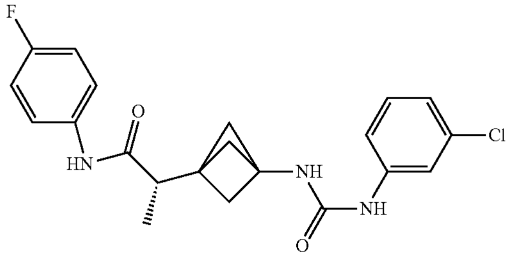 [SMILES: C[C@H](C(=O)Nc1ccc(F)cc1)C12CC(NC(=O)Nc3cccc(Cl)c3)(C1)C2] | | (S)-2-(3-(3-(3-chlorophenyl)ureido)bicyclo[1.1.1]pentan-1-yl)-N-(4-fluorophenyl)propanamide | 402.00 |
| 82 | 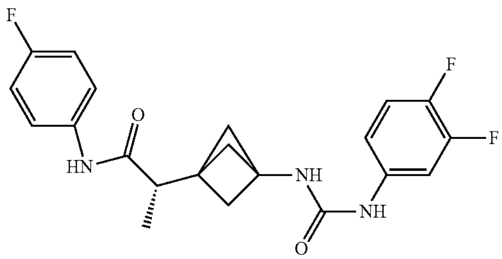 [SMILES: C[C@H](C(=O)Nc1ccc(F)cc1)C12CC(NC(=O)Nc3ccc(F)c(F)c3)(C1)C2] | | (S)-2-(3-(3-(3,4-difluorophenyl)ureido)bicyclo[1.1.1]pentan-1-yl)-N-(4-fluorophenyl)propanamide | 403.98 |
| 83 | 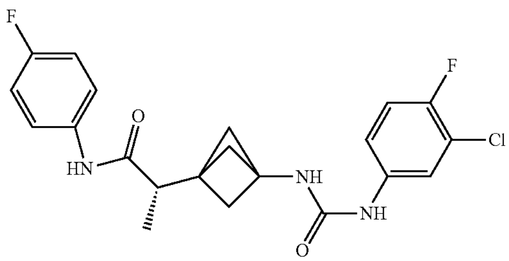 [SMILES: C[C@H](C(=O)Nc1ccc(F)cc1)C12CC(NC(=O)Nc3ccc(F)c(Cl)c3)(C1)C2] | | (S)-2-(3-(3-(3-chloro-4-fluorophenyl)ureido)bicyclo[1.1.1]pentan-1-yl)-N-(4-fluorophenyl)propanamide | 419.87 |
| 84 | 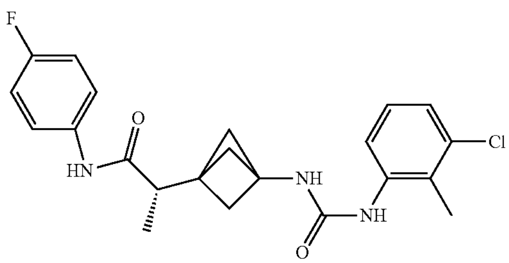 [SMILES: Cc1c(Cl)cccc1NC(=O)NC12CC([C@H](C)C(=O)Nc3ccc(F)cc3)(C1)C2] | | (S)-2-(3-(3-(3-chloro-2-methylphenyl)ureido)bicyclo[1.1.1]pentan-1-yl)-N-(4-fluorophenyl)propanamide | 416.01 |
| 85 | 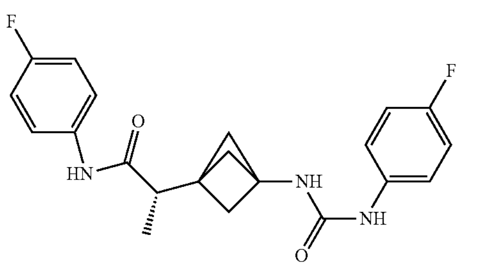 [SMILES: C[C@H](C(=O)Nc1ccc(F)cc1)C12CC(NC(=O)Nc3ccc(F)cc3)(C1)C2] | | (S)-N-(4-fluorophenyl)-2-(3-(3-(4-fluorophenyl)ureido)bicyclo[1.1.1]pentan-1-yl)propanamide | 385.96 |
| 86 | 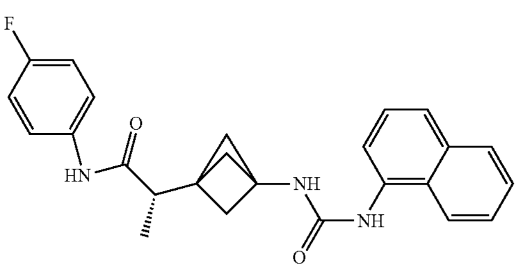 [SMILES: C[C@H](C(=O)Nc1ccc(F)cc1)C12CC(NC(=O)Nc3cccc4ccccc34)(C1)C2] | | (S)-N-(4-fluorophenyl)-2-(3-(3-(naphthalen-1-yl)ureido)bicyclo[1.1.1]pentan-1-yl)propanamide | 417.99 |

TABLE 7-continued

| Ex. # | Structure | Isocyanate monomer | Chemical Name | Mass [M + H]+ |
|---|---|---|---|---|
| 87 | 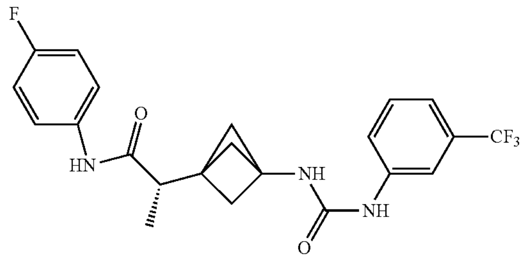 [SMILES: C[C@H](C(=O)Nc1ccc(F)cc1)C12CC(NC(=O)Nc3cccc(C(F)(F)F)c3)(C1)C2] | | (S)-N-(4-fluorophenyl)-2-(3-(3-(3-(trifluoromethyl)phenyl)ureido)bicyclo[1.1.1]pentan-1-yl)propanamide | 435.98 |

Example 88: (R)-3,4-Dichloro-N-(3-(1-((5,6-difluoropyridin-3-yl)amino)-1-oxopropan-2-yl) bicyclo[1.1.1]pentan-1-yl)benzamide Step 1: Methyl 2-(3-((tert-butoxycarbonyl)amino)bicyclo[1.1.1]pentan-1-yl)propanoate

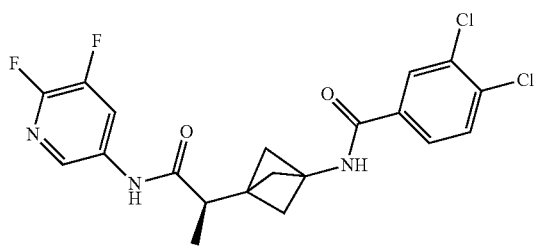 [SMILES: C[C@@H](C(=O)Nc1cnc(F)c(F)c1)C12CC(NC(=O)c3ccc(Cl)c(Cl)c3)(C1)C2]

To a 100 mL of one neck round bottom flask was charged with 2-(3-((tert-butoxycarbonyl)amino)bicyclo[1.1.1]pentan-1-yl)propanoic acid (4.0 g, 15.67 mmol) in toluene (6 ml) and MeOH (1.5 ml). To the mixture was added (triemthylsilyl)diazolmethane (15.67 ml, 31.3 mmol). The reaction was stirred at RT for 30 min. Quenched with acetic acid (3.59 ml, 62.7 mmol) and concentrated to give the title compound. The crude material was used for next step.

Step 2: Methyl 2-(3-aminobicyclo[1.1.1]pentan-1-yl)propanoate

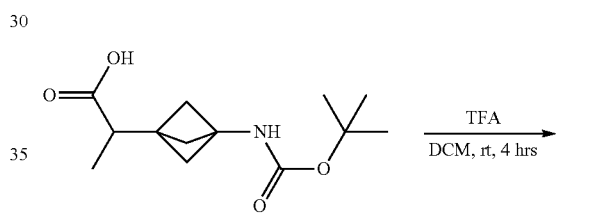

To a 100 mL flask containing methyl 2-(3-((tert-butoxycarbonyl)amino)bicyclo[1.1.1]pentan-1-yl)propanoate (4.22 g, 15.67 mmol) in DCM (25 ml) was added TFA (25 ml, 324 mmol). The mixture was stirred at RT for 4 h. The TFA and DCM were removed under reduced pressure to give crude title compound as a foam. The crude product was used for next step without further purification.

Step 3: Methyl (R)-2-(3-(3,4-dichlorobenzamido)bicyclo[1.1.1]pentan-1-yl)propanoate, and Methyl (S)-2-(3-(3,4-dichlorobenzamido)bicyclo[1.1.1]pentan-1-yl)propanoate

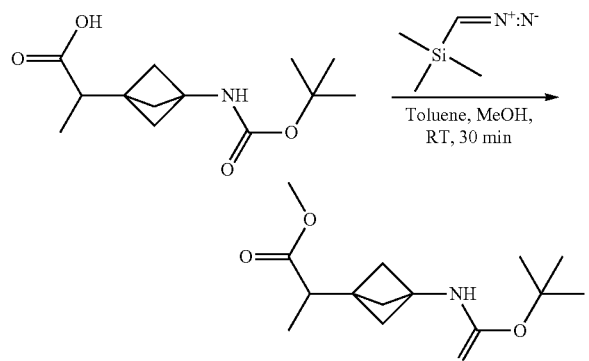

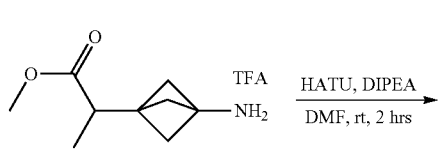

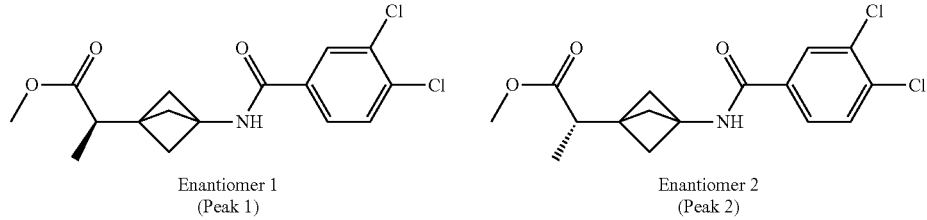

Enantiomer 1 (Peak 1)    Enantiomer 2 (Peak 2)

To a solution of methyl 2-(3-aminobicyclo[1.1.1]pentan-1-yl)propanoate (2.65 g, 15.66 mmol) in DMF (80 ml) was added 3,4-dichlorobenzoic acid (3.29 g, 17.23 mmol), HATU (7.15 g, 18.79 mmol) and DIEA (20 ml, 115 mmol) at RT. The reaction was stirred at RT for 2 h. The reaction mixture was concentrated under reduced pressure to remove most of DMF. To the residue was added hydrochloric acid (1M, 100 mL) and 300 ml of water. The mixture was extracted with EtOAc (3×150 mL). The combined organic phases were combined and washed with brine (250 mL), dried over $Na_2SO_4$, filtered and the solvent was evaporated under reduced pressure. The residue was purified by column chromatography on 330 g ISCO silica gel column, eluting with 0-50% ethyl acetate/isohexane to afford a racemic mixture of the title compound.

The racemic methyl 2-(3-(3,4-dichlorobenzamido)bicyclo[1.1.1]pentan-1-yl)propanoate was separated under SFC conditions (OJ-H, co-solvent 25% MeOH) to afford (R)-methyl 2-(3-(3,4-dichlorobenzamido)bicyclo[1.1.1]pentan-1-yl)propanoate (peak 1) and (S)-methyl 2-(3-(3,4-dichlorobenzamido)bicyclo[1.1.1]pentan-1-yl)propanoate (peak 2). The absolute stereochemistry of each enantiomer was independently determined by NMR analysis of the corresponding 1-(anthracen-9-yl)-2,2,2-trifluoroethan-1-yl esters as described in Step 4.

Step 4: Enantiomer 1: (R)-2-(3-(3,4-dichlorobenzamido)bicyclo[1.1.1]pentan-1-yl)propanoic acid

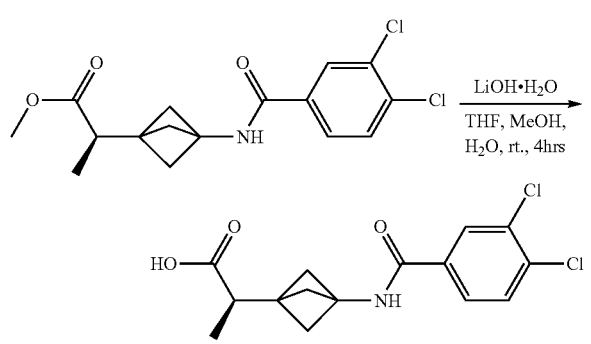

Lithium hydroxide monohydrate (0.122 g, 2.91 mmol) was added to a solution of (R)-methyl 2-(3-(3,4-dichlorobenzamido)bicyclo[1.1.1]pentan-1-yl)propanoate (enantiomer 1) (0.95 g, 2.78 mmol) in THF (6 ml)/water (3 ml), MeOH (3 ml), and the reaction was stirred at RT for 4 h. The reaction mixture was then neutralized with 12N HCl (0.456 ml, 5.55 mmol) and concentrated. The residue was dissolved in $CH_3CN/H_2O$, frozen and lyophilized overnight to give enantiomeric product (R)-2-(3-(3,4-dichlorobenzamido)bicyclo[1.1.1]pentan-1-yl)propanoic acid as a solid. The (R)-absolute stereochemistry of the title compound was determined by NMR analysis of the corresponding 1-(anthracen-9-yl)-2,2,2-trifluoroethan-1-yl ester (1-(anthracen-9-yl)-2,2,2-trifluoroethyl 2-(3-(3,4-dichlorobenzamido)bicyclo[1.1.1]pentan-1-yl)propanoate), by a modification of the method described in J. Org. Chem., 2000, 65, 2658-2666, and summarized in Chem. Rev., 2004, 104, 17-117 (FIG. 131).

Enantiomer 2: (S)-2-(3-(3,4-dichlorobenzamido)bicyclo[1.1.1]pentan-1-yl)propanoic Acid

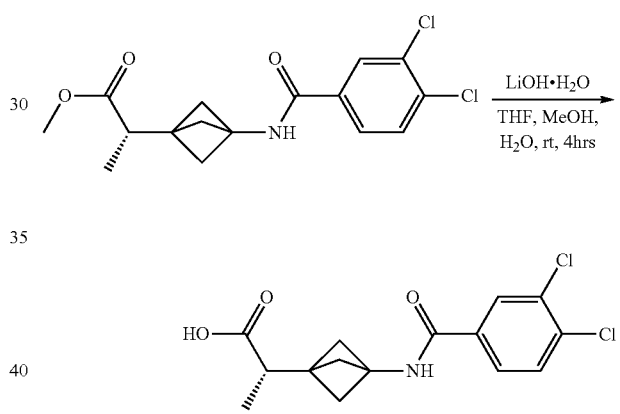

(S)-Enantiomeric carboxylic acid was prepared under conditions used to prepare the (R)-enantiomeric carboxylic acid discussed above. The (S)-absolute stereochemistry of the title compound was determined by NMR analysis of the corresponding 1-(anthracen-9-yl)-2,2,2-trifluoroethan-1-yl ester (1-(anthracen-9-yl)-2,2,2-trifluoroethyl 2-(3-(3,4-dichlorobenzamido)bicyclo[1.1.1]pentan-1-yl)propanoate), by a modification of the method described in J. Org. Chem., 2000, 65, 2658-2666, and summarized in Chem. Rev., 2004, 104, 17-117 (FIG. 131).

Step 5: (R)-3,4-Dichloro-N-(3-(1-(((5,6-difluoropyridin-3-yl)amino)-1-oxopropan-2-yl)bicyclo[1.1.1]pentan-1-yl)benzamide

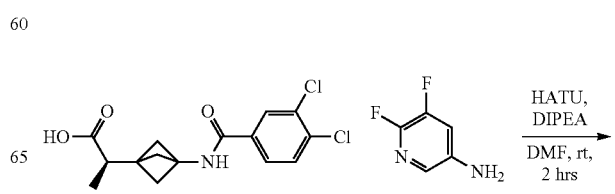

-continued

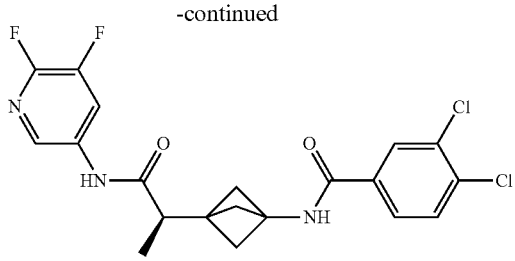

To a solution of (R)-2-(3-(3,4-dichlorobenzamido)bicyclo[1.1.1]pentan-1-yl)propanoic acid (21.2 mg, 0.065 mmol) in DMF (0.8 ml) was added 5,6-difluoropyridin-3-amine (0.023 mg, 0.175 mmol), HATU (29.5 mg, 0.078 mmol) followed by DIEA (0.045 ml, 0.258 mmol). The reaction mixture was stirred at RT for 18 h, and then heated to 60° C. for another 18 h. The reaction mixture was purified directly by reverse phase chromatography (C-18 column) using 0-100% water in acetonitrile+0.05% TFA to give (R)-3,4-dichloro-N-(3-(1-((5,6-difluoropyridin-3-yl)amino)-1-oxopropan-2-yl)bicyclo[1.1.1]pentan-1-yl)benzamide as a solid. ¹H NMR (400 MHz, Methanol-d₄): δ 8.26-8.15 (m, 1H), 8.03 (s, 1H), 7.90 (s, 1H), 7.66 (d, J=8.4 Hz, 1H), 7.56 (d, J=8.3 Hz, 1H), 2.74 (q, J=6.7 Hz, 1H), 2.38-1.76 (m, 7H), 1.11 (dd, J=22.7, 6.9 Hz, 3H); MS (ESI) m/z: 441.0 [M+H]⁺.

The following R-enantiomeric compounds from enantiomer 1 in Table 8 were prepared by a similar procedure used for Example 88 using commercially available amines.

TABLE 8

| Ex# | Structure | Chemical Name | Mass [M + H]⁺ |
|---|---|---|---|
| 89 | 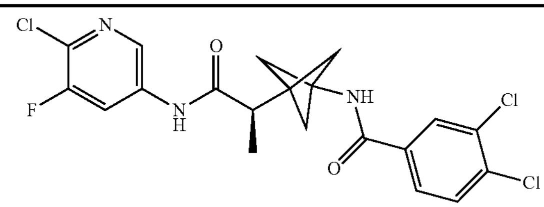 | (R)-3,4-dichloro-N-(3-(1-((6-chloro-5-yl)amino)-1-oxopropan-2-yl)bicyclo[1.1.1]pentan-1-yl)benzamide | 455.9 |
| 90 | 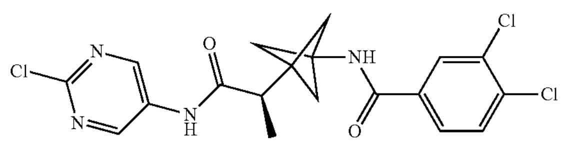 [SMILES: C[C@@H](C(=O)Nc1cnc(Cl)nc1)C12CC(NC(=O)c3ccc(Cl)c(Cl)c3)(C1)C2] | (R)-3,4-dichloro-N-(3-(1-((2-chloropyrimidin-5-yl)amino)-1-oxopropan-2-yl)bicyclo[1.1.1]pentan-1-yl)benzamide | 438.9 |
| 91 | 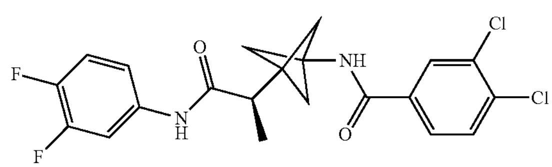 [SMILES: C[C@@H](C(=O)Nc1ccc(F)c(F)c1)C12CC(NC(=O)c3ccc(Cl)c(Cl)c3)(C1)C2] | (R)-3,4-dichloro-N-(3-(1-((3,4-difluorophenyl)amino)-1-oxopropan-2-yl)bicyclo[1.1.1]pentan-1-yl)benzamide | 438.9 |
| 92 | 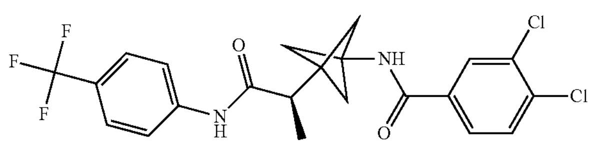 [SMILES: C[C@@H](C(=O)Nc1ccc(C(F)(F)F)cc1)C12CC(NC(=O)c3ccc(Cl)c(Cl)c3)(C1)C2] | (R)-3,4-dichloro-N-(3-(1-oxo-1-((4-(trifluoromethyl)phenyl)amino)propan-2-yl)bicyclo[1.1.1]pentan-1-yl)benzamide | 471.0 |

The following S-enantiomeric compounds in Table 9 were prepared from enantiomer 2 by following similar procedure for Example 88.

TABLE 9

| Ex# | Structure | Chemical Name | Mass [M + H]⁺ |
|---|---|---|---|
| 93 | 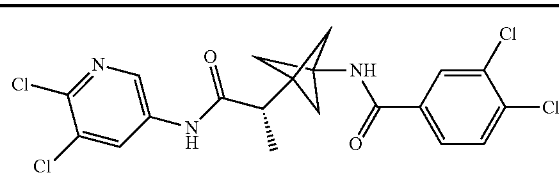 | (S)-3,4-dichloro-N-(3-(1-((5,6-dichloropyridin-3-yl)amino)-1-oxopropan-2-yl)bicyclo[1.1.1]pentan-1-yl)benzamide | 477.9 |

TABLE 9-continued

| Ex# | Structure | Chemical Name | Mass [M + H]+ |
|---|---|---|---|
| 94 | 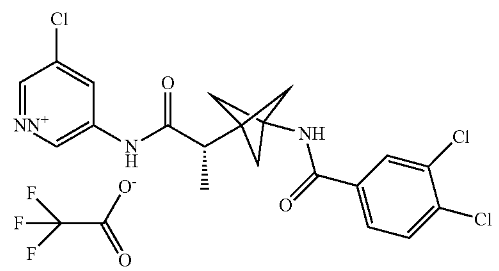 | (S)-3-chloro-5-(2-(3-(3,4-dichlorobenzamido)bicyclo[1.1.1]pentan-1-yl)propanamido)pyridin-1-ium 2,2,2-trifluoroacetate | 437.9 |
| 95 | 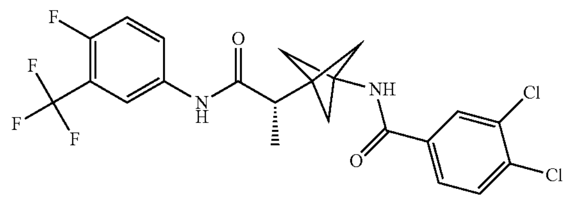 [SMILES: C[C@H](C(=O)Nc1ccc(F)c(C(F)(F)F)c1)C12CC(NC(=O)c3ccc(Cl)c(Cl)c3)(C1)C2] | (S)-3,4-dichloro-N-(3-(1-((4-fluoro-3-(trifluoromethyl)phenyl)amino)-1-oxopropan-2-yl)bicyclo[1.1.1]pentan-1-yl)benzamide | 488.9 |
| 96 | 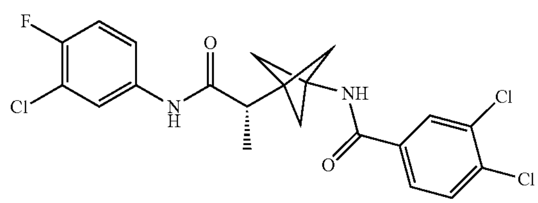 [SMILES: C[C@H](C(=O)Nc1ccc(F)c(Cl)c1)C12CC(NC(=O)c3ccc(Cl)c(Cl)c3)(C1)C2] | (S)-3,4-dichloro-N-(3-(1-((3-chloro-4-fluorophenyl)amino)-1-oxopropan-2-yl)bicyclo[1.1.1]pentan-1-yl)benzamide | 454.9 |
| 97 | 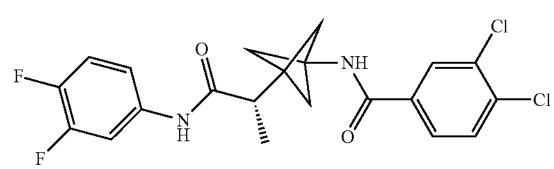 [SMILES: C[C@H](C(=O)Nc1ccc(F)c(F)c1)C12CC(NC(=O)c3ccc(Cl)c(Cl)c3)(C1)C2] | (S)-3,4-dichloro-N-(3-(1-((3,4-difluorophenyl)amino)-1-oxopropan-2-yl)bicyclo[1.1.1]pentan-1-yl)benzamide | 438.9 |
| 98 | 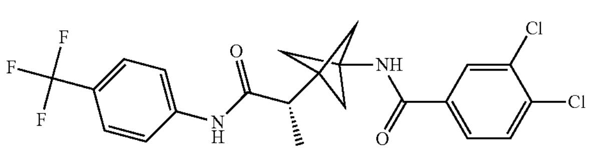 [SMILES: C[C@H](C(=O)Nc1ccc(C(F)(F)F)cc1)C12CC(NC(=O)c3ccc(Cl)c(Cl)c3)(C1)C2] | (S)-3,4-dichloro-N-(3-(1-oxo-1-((4-(trifluoromethyl)phenyl)amino)propan-2-yl)bicyclo[1.1.1]pentan-1-yl)benzamide | 470.8 |
| 99 | 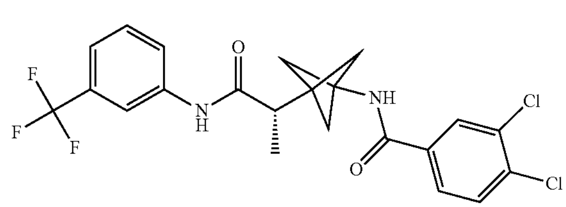 [SMILES: C[C@H](C(=O)Nc1cccc(C(F)(F)F)c1)C12CC(NC(=O)c3ccc(Cl)c(Cl)c3)(C1)C2] | (S)-3,4-dichloro-N-(3-(1-oxo-1-((3-(trifluoromethyl)phenyl)amino)propan-2-yl)bicyclo[1.1.1]pentan-1-yl)benzamide | 471.0 |

Example 100: 3,4-Dichloro-N-(3-(1-((4-fluorophenyl)carbamoyl)cyclopropyl)bicyclo[1.1.1]pentan-1-yl)benzamide

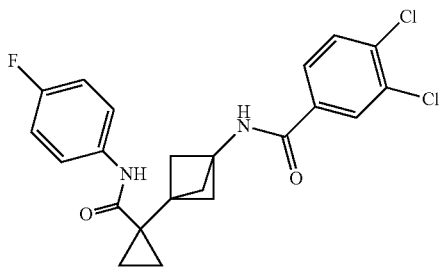 [SMILES: O=C(NC12CC(C3(C(=O)Nc4ccc(F)cc4)CC3)(C1)C2)c1ccc(Cl)c(Cl)c1]

The title compound was prepared in an analogous fashion to that described for the synthesis of Examples 6 and 7, except that in Step 1, dibromoethane was used in place of iodomethane and 3.2 equivalents of lithium bis (trimethylsilyl) amide was used in place of two equivalents. MS (ESI) m/z: 433, 435 [M+H$^+$].

Example 101: 3,4-Dichloro-N-(3-(1-((4-fluorophenyl)amino)-2-methyl-1-oxopropan-2-yl)bicyclo[1.1.1]pentan-1-yl)benzamide

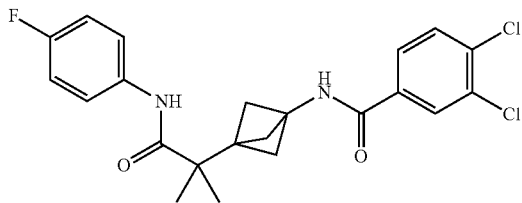 [SMILES: CC(C)(C(=O)Nc1ccc(F)cc1)C12CC(NC(=O)c3ccc(Cl)c(Cl)c3)(C1)C2]

Step 1: Methyl 2-(3-((tert-butoxycarbonyl)amino)bicyclo[1.1.1]pentan-1-yl)propanoate

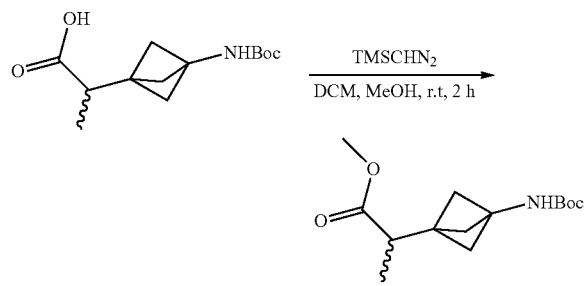

To a solution of 2-(3-((tert-butoxycarbonyl)amino)bicyclo[1.1.1]pentan-1-yl)propanoic acid (1.5 g, 5.88 mmol) in DCM (5 mL) and MeOH (1 mL) was added (diazomethyl)trimethylsilane (8.81 ml, 8.81 mmol) with stirring at 0° C. slowly. After the addition was complete, the reaction mixture was stirred at 0° C. The reaction was monitored by TLC (petroleum ether:EtOAC=3:1), after stirred at 0° C. for 3 h. The reaction was finished. Then the solvent was removed in vacuo. The residue was purified by flash silica gel chromatography (ISCO®; Agela® Flash Column Silica-CS (12 g), Eluented by 13% Ethyl acetate/Petroleum ether gradient @ 30 mL/min) to afford the title compound as an oil. MS (ESI) m/z: 214.0 [M−t−Bu+H$^+$]. $^1$H NMR (400 MHz, CD$_3$OD) δ 3.66 (s, 3H), 2.68 (q, J=7.0 Hz, 1H), 1.86 (s, 6H), 1.43 (s, 9H), 1.09 (d, J=7.1 Hz, 3H).

Step 2: Methyl 2-(3-((tert-butoxycarbonyl)amino)bicyclo[1.1.1]pentan-1-yl)-2-methylpropanoate

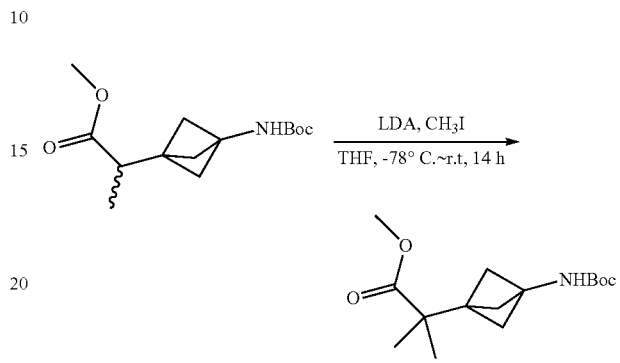

To a solution of methyl 2-(3-((tert-butoxycarbonyl)amino)bicyclo[1.1.1]pentan-1-yl)propanoate (1.4 g, 5.20 mmol) in THF (10.0 mL) was added LDA (5.72 mL, 11.44 mmol) with stirring at ~78° C. under N$_2$ atmosphere. After stirring at −78° C. for 1 h, MeI (0.355 ml, 7.96 mmol) was added at −78° C., then the reaction was slowly allowed to −15° C. The reaction was monitored by LCMS, after stirring at 15° C. for 14 h, the reaction was finished. The reaction was quenched by the addition of MeOH (10 mL), then the solvent was removed by concentration, the residue was purified by reversed phase HPLC on a GILSON 281 instrument fitted with a YMC-Actus Pro C18 150*30 5 u using water (0.1% TFA) and acetonitrile as eluents, followed by lyophilization to afford the title compound as an oil. MS (ESI) m/z: 184.1 [M−Boc+H$^+$], 228.0 [M−t−Bu+H$^+$]. $^1$H NMR (400 MHz, CD$_3$OD) δ 3.65 (s, 3H), 1.84 (s, 6H), 1.43 (s, 9H), 1.14 (s, 6H).

Step 3: Methyl 2-(3-aminobicyclo[1.1.1]pentan-1-yl)-2-methylpropanoate Hydrochloride

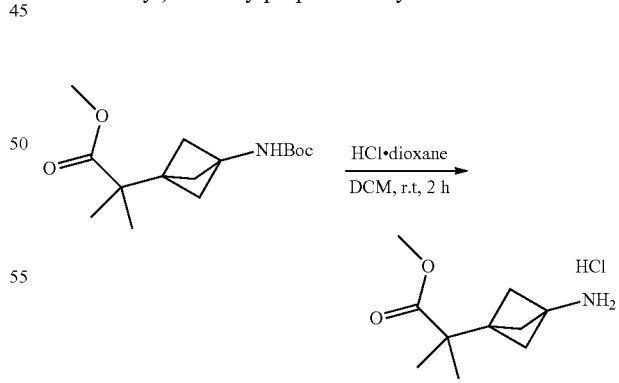

To a solution of methyl 2-(3-((tert-butoxycarbonyl)amino)bicyclo[1.1.1]pentan-1-yl)-2-methylpropanoate (200 mg, 0.706 mmol) in DCM (3.0 mL) were added 4.0 M HCl in dioxane (2.0 mL, 8.00 mmol,) with stirring at ~15° C. After the addition was complete, the reaction mixture was stirred at the same temperature. The reaction was monitored by TLC (petroleum ether:EtOAC=5:1), after stirring at 15°

C. for 2 h, the reaction was finished. Then the solvent was removed by concentration to afford the title compound as an oil, which was used for next step without further purification.

Step 4: Methyl 2-(3-(3,4-dichlorobenzamido)bicyclo[1.1.1]pentan-1-yl)-2-methylpropanoate

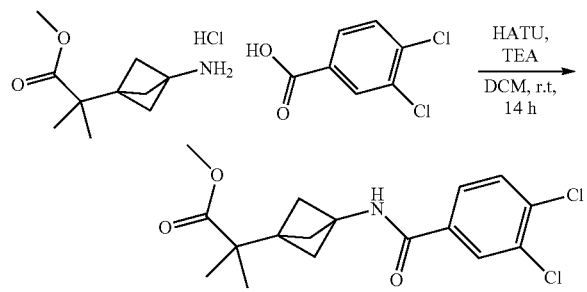

To a solution of methyl 2-(3-aminobicyclo[1.1.1]pentan-1-yl)-2-methylpropanoate hydrochloride (74 mg, 0.337 mmol) and TEA (0.141 ml, 1.010 mmol) in DCM (5.0 mL) were added HATU (141 mg, 0.370 mmol) and 3,4-dichlorobenzoic acid (65 mg, 0.340 mmol) with stirring at ~15° C. After the addition was complete, the reaction mixture was stirred at 15° C. The reaction was monitored by LCMS, after stirring at 15° C. for 14 h, the reaction was finished. The reaction mixture was concentrated. The residue was purified by Pre-TLC using (petroleum ether/ethyl acetate 3:1 as eluent) to afford the title compound as a solid. MS (ESI) m/z: 356.1 [M+H$^+$]. $^1$H NMR (400 MHz, CD$_3$OD) δ 7.96 (d, J=1.8 Hz, 1H), 7.69-7.74 (m, 1H), 7.59-7.64 (m, 1H), 3.68 (s, 3H), 2.03 (s, 6H), 1.18 (s, 6H).

Step 5: 2-(3-(3,4-Dichlorobenzamido)bicyclo[1.1.1]pentan-1-yl)-2-methylpropanoic Acid

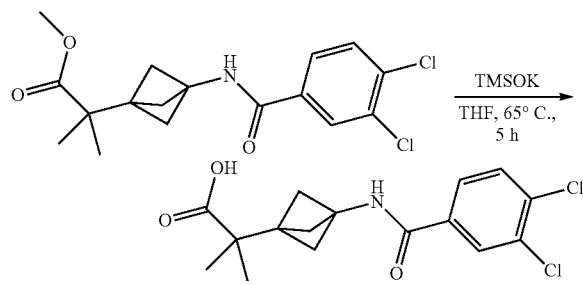

To a solution of methyl 2-(3-(3,4-dichlorobenzamido)bicyclo[1.1.1]pentan-1-yl)-2-methylpropanoate (96 mg, 0.269 mmol) in THF (1.0 mL) was added potassium trimethylsilanolate (277 mg, 2.156 mmol) with stirring at ~20° C. under N$_2$ atmosphere. After the addition was complete, the reaction mixture was stirred at 65° C. The reaction was monitored by LCMS. After stirring at 65° C. for 5 h, the reaction was finished. The reaction was cooled to RT. HCl Dioxane (0.4 N diluted with THF) was added until pH~6. Then the mixture was concentrated to afford the title compound as a solid, which was used in next step without further purification. MS (ESI) m/z: 342.0 [M+H$^+$].

Step 6: 3,4-Dichloro-N-(3-(1-((4-fluorophenyl)amino)-2-methyl-1-oxopropan-2-yl)bicyclo[1.1.1]pentan-1-yl)benzamide

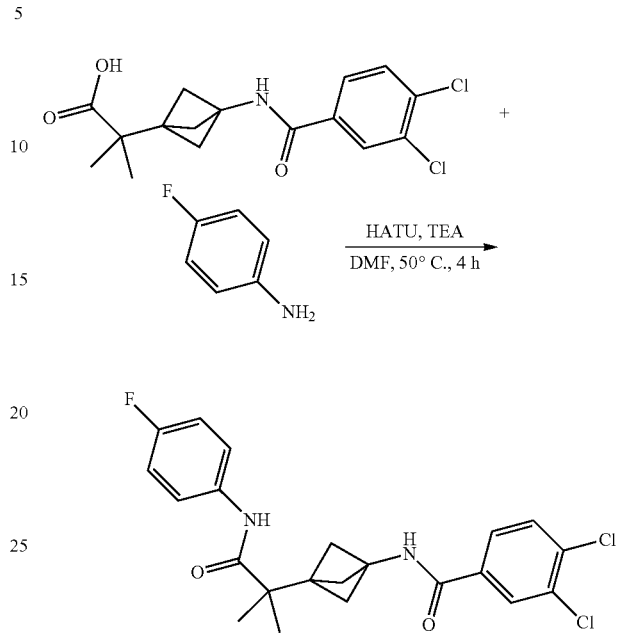

To a solution of 2-(3-(3,4-dichlorobenzamido)bicyclo[1.1.1]pentan-1-yl)-2-methylpropanoic acid (45 mg, 0.131 mmol) and TEA (0.06 mL, 0.430 mmol) in DMF (5.0 mL) were added HATU (50 mg, 0.131 mmol) and 4-fluoroaniline (20 mg, 0.180 mmol) with stirring at ~15° C. After the addition was complete, the reaction mixture was stirred at 50° C. The reaction was monitored by LCMS, after stirring at 50° C. for 4 h, the reaction was finished. The reaction mixture was purified by reversed phase HPLC on a GILSON 281 instrument fitted with Boston Green ODS (150*30 mm*5 μm) using water (0.1% TFA)-MeCN as eluents (Mobile phase A water (0.1% TFA), Mobile phase B acetonitrile, Detective wavelength 220 nm) followed by lyophilization to afford the title compound as a solid. MS (ESI) m/z: 435.2 [M+H$^+$]. $^1$H NMR (400 MHz, CDCl$_3$) δ 7.83 (d, J=2.2 Hz, 1H), 7.54-7.60 (m, 1H), 7.49-7.53 (m, 1H), 7.42-7.48 (m, 2H), 7.22 (s, 1H), 7.03 (t, J=8.8 Hz, 2H), 6.48 (s, 1H), 2.15 (s, 6H), 1.30 (s, 6H).

Example 102: 3-Chloro-N-(3-(1-((4-fluorophenyl)amino)-2-methyl-1-oxopropan-2-yl)bicyclo[1.1.1]pentan-1-yl)benzamide

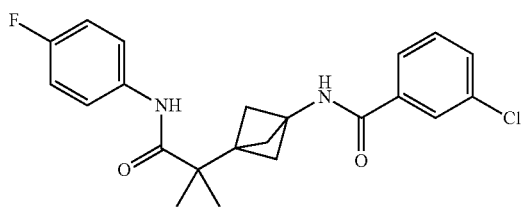 [SMILES: CC(C)(C(=O)Nc1ccc(F)cc1)C12CC(NC(=O)c3cccc(Cl)c3)(C1)C2]

Step 1: Methyl 2-(3-(3-chlorobenzamido)bicyclo[1.1.1]pentan-1-yl)-2-methylpropanoate

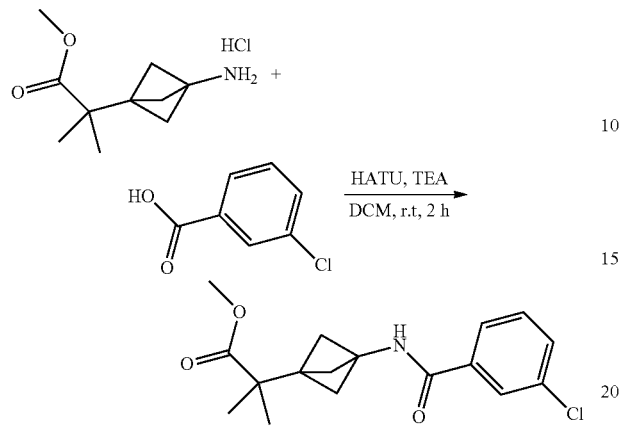

To a solution of methyl 2-(3-aminobicyclo[1.1.1]pentan-1-yl)-2-methylpropanoate hydrochloride (74 mg, 0.337 mmol) and TEA (0.14 mL, 1.010 mmol) in DCM (5.0 mL) were added HATU (141 mg, 0.370 mmol) and 3-chlorobenzoic acid (65 mg, 0.415 mmol) with stirring at ~15° C. After the addition was complete, the reaction mixture was stirred at 15° C. The reaction was monitored by LCMS, after stirring at 15° C. for 2 h, the reaction was finished. Then the solvent was removed off by concentration. The residue was purified by Pre-TLC (petroleum ether/ethyl acetate 3:1 as eluent) to afford the title compound as a solid. MS (ESI) m/z: 322.1 [M+H$^+$]. $^1$H NMR (400 MHz, CD$_3$OD) δ 7.81 (s, 1H) 7.72 (d, J=7.8 Hz, 1H) 7.51-7.57 (m, 1H) 7.41-7.47 (m, 1H) 7.41-7.47 (m, 1H) 3.68 (s, 3H) 2.04 (s, 6H) 1.18 (s, 6H).

Step 2: 2-(3-(3-Chlorobenzamido)bicyclo[1.1.1]pentan-1-yl)-2-methylpropanoic Acid

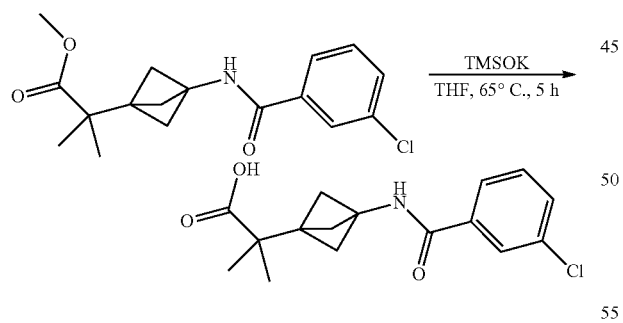

To a solution of methyl 2-(3-(3-chlorobenzamido)bicyclo[1.1.1]pentan-1-yl)-2-methylpropanoate (55 mg, 0.171 mmol) in THF (6 mL) was added potassium trimethylsilanolate (175 mg, 1.367 mmol) with stirring at ~20° C. under N$_2$ atmosphere. After the addition was complete, the reaction mixture was stirred at 65° C. The reaction was monitored by LCMS, after stirring at 65° C. for 5 h, the reaction was finished. The reaction was cooled to RT. Then HCl Dioxane (0.4 N diluted with THF) was added until pH~6. Then the mixture was concentrated to afford the title compound as a solid, which was used in next step without further purification. MS (ESI) m/z: 308.1[M+H$^+$].

Step 3: 3-Chloro-N-(3-(1-((4-fluorophenyl)amino)-2-methyl-1-oxopropan-2-yl)bicyclo[1.1.1]pentan-1-yl)benzamide

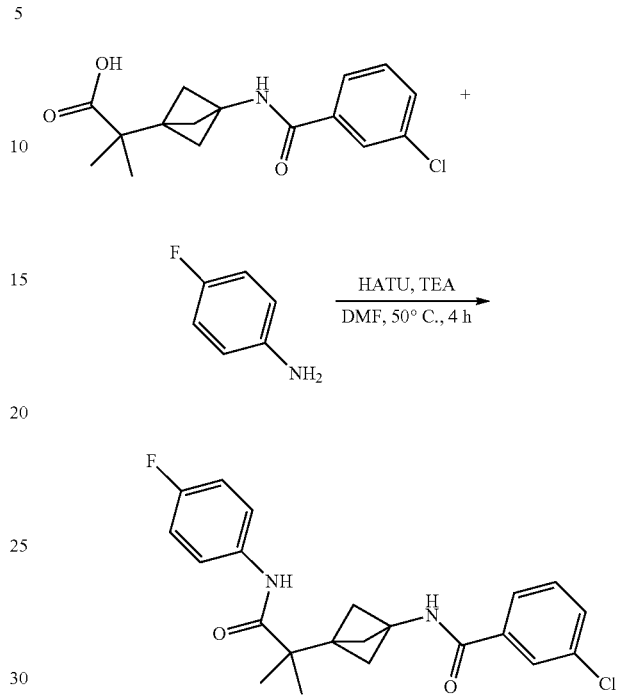

To a solution of 2-(3-(3-chlorobenzamido)bicyclo[1.1.1]pentan-1-yl)-2-methylpropanoic acid (25 mg, 0.081 mmol) and TEA (0.04 ml, 0.287 mmol) in DMF (5.0 mL) were added HATU (34 mg, 0.089 mmol) and 4-fluoroaniline (10 mg, 0.090 mmol) with stirring at −15° C. After the addition was complete, the reaction mixture was stirred at 50° C. The reaction was monitored by LCMS, after stirring at 50° C. for 4 h, the reaction was finished. The reaction mixture was purified by reversed phase HPLC on a GILSON 281 instrument fitted with Boston Green ODS (150*30 mm*5 μm) using water (0.1% TFA)-MeCN as eluents (Mobile phase A water (0.1% TFA), Mobile phase B acetonitrile, Detective wavelength 220 nm) followed by lyophilization to afford the title compound as a solid. MS (ESI) m/z: 401.1 [M+H$^+$]. $^1$H NMR (400 MHz, CDCl$_3$) δ 7.72 (s, 1H), 7.62 (d, J=7.9 Hz, 1H), 7.43-7.50 (m, 3H), 7.34-7.40 (m, 1H), 7.22 (s, 1H), 7.03 (t, J=8.8 Hz, 2H), 6.47 (br s, 1H), 2.15 (s, 6H), 1.31 (s, 6H).

Example 103: 3,4-Dichloro-N-(3-(2-(4-fluorobenzamido)propan-2-yl)bicyclo[1.1.1]pentan-1-yl)benzamide

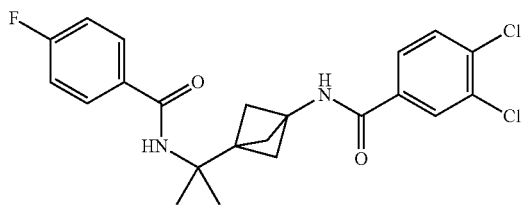 [SMILES: CC(C)(NC(=O)c1ccc(F)cc1)C12CC(NC(=O)c3ccc(Cl)c(Cl)c3)(C1)C2]

Step 1: 3-((Tert-butoxycarbonyl)amino)bicyclo[1.1.1]pentane-1-carboxylic Acid

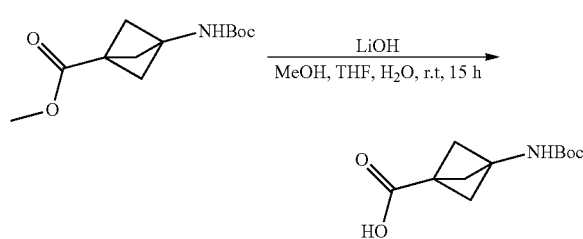

To a solution of methyl 3-((tert-butoxycarbonyl)amino)bicyclo[1.1.1]pentane-1-carboxylate (3 g, 12.43 mmol) in MeOH (16 mL), THF (16 mL) and water (5 mL) was added lithium hydroxide (0.893 g, 37.3 mmol) at ~15° C. After the addition was complete, the reaction was stirred at the same temperature. The reaction was monitored by TLC (Pet.ether:EtOAc=3:1). After stirring at 15° C. for 15 h, the reaction was finished. The reaction was cooled to 0° C., diluted with water (30 mL), acidified by 1N HCl to pH~6, and extracted with EtOAc (40 mL×4). The organic layer was separated, dried over Na$_2$SO$_4$ and filtered. The filtrate was concentrated to afford the title compound as a solid, which was used in the next step without further purification. $^1$H NMR (400 MHz, CD$_3$OD) δ 2.21 (s, 6H) 1.44 (br s, 9H)

Step 2: Tert-butyl (3-(methoxy(methyl)carbamoyl)bicyclo[1.1.1]pentan-1-yl)carbamate

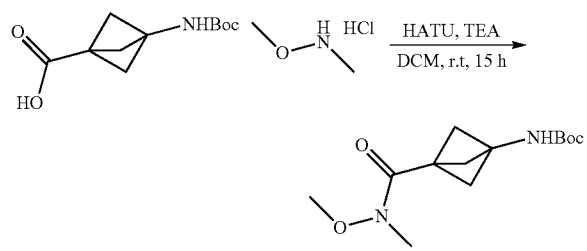

To a solution of 3-((tert-butoxycarbonyl)amino)bicyclo[1.1.1]pentane-1-carboxylic acid (2.8 g, 12.32 mmol) in DCM (30 mL) were added HATU (7 g, 18.41 mmol), N,O-dimethylhydroxylamine hydrochloride (1.202 g, 12.32 mmol) and DIEA (6.5 mL, 37.2 mmol) at ~15° C. After the addition was finished, the reaction was stirred at 15° C. The reaction was monitored by LCMS, after stirring at 15° C. for 15 h, the reaction was finished. The reaction was poured into water (20 mL) and extracted by DCM (30 mL×3). The organic layers were collected, washed with brine (20 mL), and dried over anhydrous Na$_2$SO$_4$. After filtration, the filtrate was concentrated in vacuo. The residue was purified by flash silica gel chromatography (ISCO®; Agela® Flash Column Silica-CS (40 g), Eluent of 0~32% Ethyl acetate/Petroleum ether gradient @ 40 mL/min) to afford the title compound as a solid. MS (ESI) m/z: 271.1 [M+H$^+$]; $^1$H NMR (400 MHz, CD$_3$OD) δ 3.71 (s, 3H) 3.18 (s, 3H) 2.29 (s, 6H) 1.44 (br s, 9H)

Step 3: 3-Amino-N-methoxy-N-methylbicyclo[1.1.1]pentane-1-carboxamide Hydrochloride

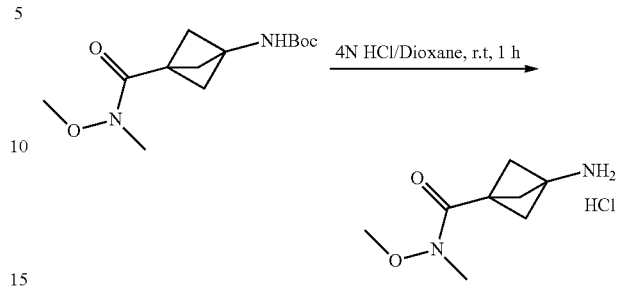

To a solution of tert-butyl (3-(methoxy(methyl)carbamoyl)bicyclo[1.1.1]pentan-1-yl)carbamate (500 mg, 1.850 mmol) in DCM (5 mL) was added 4M HCl in dioxane (5 mL, 20.00 mmol) at ~20° C. After the addition was finished, the reaction was stirred at 20° C. The reaction was monitored by TLC (pet.ether/EtOAc=1:1). After stirring at 20° C. for 1 h, the reaction was finished. The reaction solvent was removed under reduced pressure to afford the title compound as an oil, which was used in the next step without further purification. $^1$H NMR (500 MHz, CD$_3$OD) δ 3.73-3.75 (m, 3H) 3.20 (s, 3H) 2.40 (s, 6H)

Step 4: 3-(3,4-Dichlorobenzamido)-N-methoxy-N-methylbicyclo[1.1.1]pentane-1-carboxamide

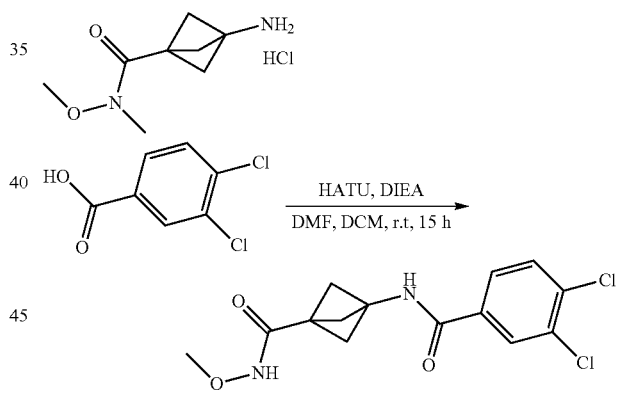

To a solution of 3-amino-N-methoxy-N-methylbicyclo[1.1.1]pentane-1-carboxamide hydrochloride (380 mg, 1.839 mmol) in DCM (5 mL) and DMF (2 mL) were added HATU (2 g, 5.26 mmol), 3,4-dichlorobenzoic acid (351 mg, 1.839 mmol) and DIEA (1.5 mL, 8.59 mmol) at ~10° C. After the addition was finished, the reaction was stirred at the same temperature. The reaction was monitored by LCMS. After stirring at 10° C. for 15 h, the reaction was finished. The reaction was poured into water (20 mL) and extracted by EtOAc (30 mL×2). The organic layers were collected, washed with brine (20 mL), and dried over anhydrous Na$_2$SO$_4$. After filtration, the filtrate was concentrated in vacuo. The residue was purified by flash silica gel chromatography (ISCO®; Agela® Flash Column Silica-CS (12 g), Eluent of 0-48% Ethyl acetate/Petroleum ether gradient @ 30 mL/min) to afford the title compound as a solid. MS (ESI) m/z: 343.0[M+H$^+$]; $^1$H NMR (500 MHz, CD$_3$OD) δ 7.99 (br d, J=2.1 Hz, 1H) 7.97 (d, J=2.1 Hz, 1H)

7.73 (dd, J=8.4, 2.1 Hz, 1H) 7.63 (d, J=8.4 Hz, 1H) 3.74 (s, 3H) 3.21 (br s, 3H) 2.48 (s, 6H)

Step 5: N-(3-Acetylbicyclo[1.1.1]pentan-1-yl)-3,4-dichlorobenzamide

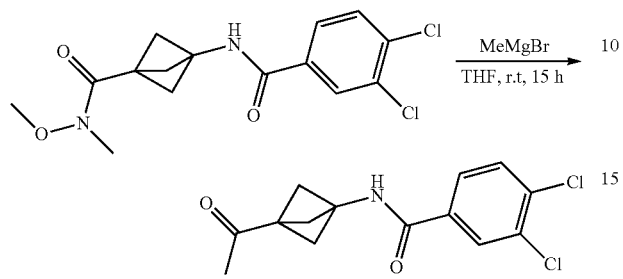

To a stirred solution of 3-(3,4-dichlorobenzamido)-N-methoxy-N-methylbicyclo[1.1.1]pentane-1-carboxamide (400 mg, 1.165 mmol) in THF (10 mL) was added methylmagnesium bromide (2 mL, 6.00 mmol) (3 M) at 0° C. under N₂. After the addition was complete, the mixture was stirred at −15° C. The reaction was monitored by TLC (Petroleum ether/EtOAc). After stirring at 15° C. for 15 h, the reaction was finished. The reaction was quenched with saturated NH₄Cl (15 mL), then extracted with EtOAc (10 mL×3), the organic layer was separated, dried over Na₂SO₄ and filtered. The filtrate was concentrated and purified by silica gel chromatography (ISCO®; Agela® Flash Column Silica-CS (4 g), Eluent of 0-38% Ethyl acetate/Petroleum ether gradient @ 30 mL/min) to afford the title compound as a solid. ¹H NMR (400 MHz, CDCl₃) δ 7.85 (d, J=2.14 Hz, 1H) 7.57-7.61 (m, 1H) 7.50-7.55 (m, 1H) 6.5 (br s, 1H) 2.46 (s, 6H) 2.20 (s, 3H)

Step 6: (Z)—N-(3-(1-((Tert-butylsulfinyl)imino)ethyl)bicyclo[1.1.1]pentan-1-yl)-3,4-dichlorobenzamide

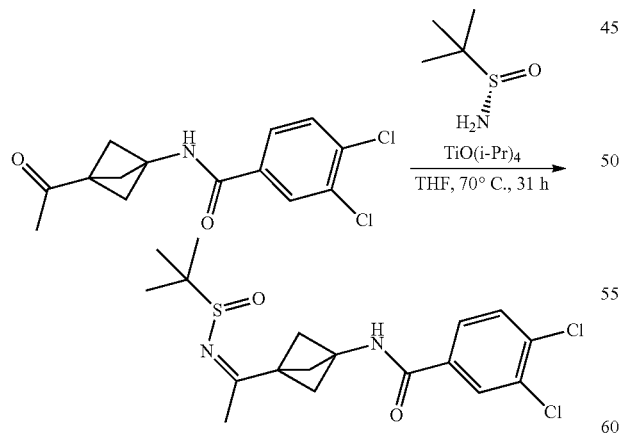

To a solution of N-(3-acetylbicyclo[1.1.1]pentan-1-yl)-3,4-dichlorobenzamide (270 mg, 0.906 mmol) in THF (5 mL) were added (S)-2-methylpropane-2-sulfinamide (330 mg, 2.71 mmol) and tetraisopropoxytitanium (1030 mg, 3.62 mmol) at −15° C. After the addition was finished, the reaction was stirred at 70° C. The reaction was monitored by LCMS, after stirring at 70° C. for around 31 h, the reaction was finished. Water (3 mL) was added to the mixture, then filtered. The filtrate was extracted by EtOAc (5 mL×2), then the organic layers were collected, washed with brine, and dried over Na₂SO₄. After filtration, the filtrate was concentrated in vacuo. The residue was purified by flash silica gel chromatography (ISCO®; Agela® Flash Column Silica-CS (4 g), Eluent of 0-30% Ethyl acetate/Petroleum ether gradient @30 mL/min) to afford the title compound as a solid. MS (ESI) m/z: 401.1 [M+H⁺]; ¹H NMR (500 MHz, CD₃OD) δ 7.97 (d, J=2.0 Hz, 1H) 7.71-7.75 (m, 1H) 7.59-7.63 (m, 1H) 2.36-2.40 (m, 6H) 2.33 (s, 3H) 1.23 (s, 8H)

Step 7: N-(3-(2-((tert-butylsulfinyl)amino)propan-2-yl)bicyclo[1.1.1]pentan-1-yl)-3,4-dichlorobenzamide

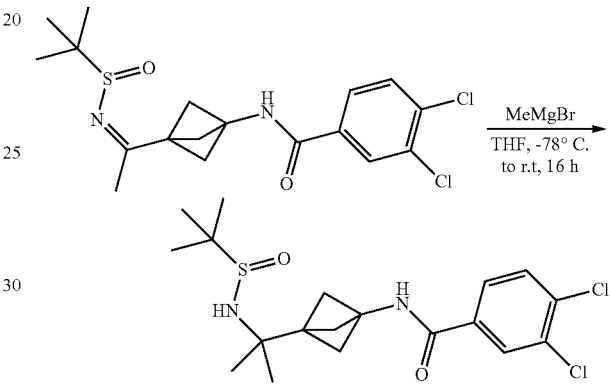

To a stirred solution of (Z)—N-(3-(1-((tert-butylsulfinyl)imino)ethyl)bicyclo[1.1.1]pentan-1-yl)-3,4-dichlorobenzamide (200 mg, 0.498 mmol) in THF (2 mL) was added methylmagnesium bromide (0.83 ml, 2.490 mmol) (3 M in Ethyl Ether) at −78° C. After the addition was finished, the reaction was stirred at ~15° C. The reaction was monitored by LC-MS, after stirring at 15° C. for 16 h, the reaction was finished. The reaction was quenched by saturated NH₄Cl (3 mL), then extracted by EtOAc (2 mL×2), the organic layers were collected, washed with brine, dried over Na₂SO₄. After filtration, the filtrate was concentrated in vacuo. The residue was purified by prep-TLC (DCM/MeOH=10:1) to afford the title compound as an oil. MS (ESI) m/z: 417.1 [M+H⁺]

Step 8: N-(3-(2-aminopropan-2-yl)bicyclo[1.1.1]pentan-1-yl)-3,4-dichlorobenzamide hydrochloride

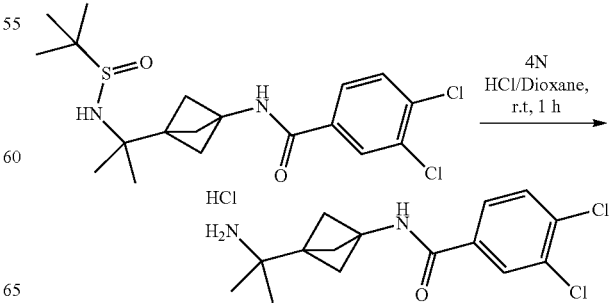

A mixture of 3,4-dichloro-N-(3-(2-(1,1-dimethylethylsulfinamido)propan-2-yl)bicyclo[1.1.1]pentan-1-yl)benzamide (25 mg, 0.060 mmol) in 4M HCl in dioxane (300 μL, 1.200 mmol) was stirred at ~15° C. The reaction was monitored by TLC (DCM/MeOH=10:1), after stirring at RT for 1 h, the reaction was finished. The reaction mixture was concentrated under reduced pressure to afford the title compound as a solid. MS (ESI) m/z: 313.1 [M+H$^+$]

Step 9: 3,4-Dichloro-N-(3-(2-(4-fluorobenzamido)propan-2-yl)bicyclo[1.1.1]pentan-1-yl)benzamide

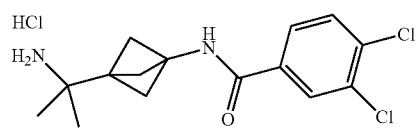

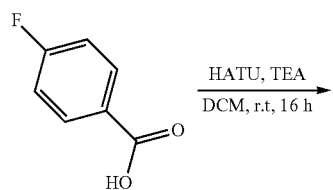

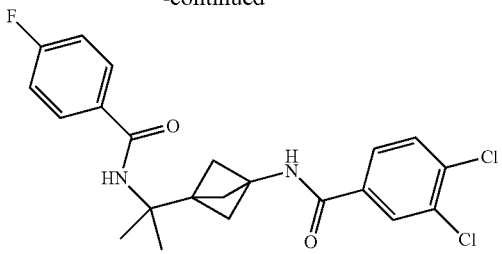

To a stirred solution of N-(3-(2-aminopropan-2-yl)bicyclo[1.1.1]pentan-1-yl)-3,4-dichlorobenzamide hydrochloride (18 mg, 0.051 mmol) and 4-fluorobenzoic acid (8 mg, 0.057 mmol) in CH$_2$Cl$_2$ (1 mL) were added HATU (20 mg, 0.053 mmol) and TEA (16 mg, 0.158 mmol) at ~15° C. After the addition was finished, the reaction was stirred at 15° C. The reaction was monitored by LC-MS. After stirring at 15° C. for ~16 h, the reaction was finished. The solvent was removed under reduced pressure. The residue was purified by reverse phase HPLC on a EJ instrument fitted with a Boston Green ODS 150*30 5 u using water (0.1% TFA)-CH$_3$CN as eluents, followed by concentration (below 50° C.) to afford the title compound as a solid. MS (ESI) m/z: 435.1 [M+H$^+$]; $^1$H NMR (500 MHz, CD$_3$OD) δ 9.05 (s, 1H) 7.96 (d, J=2.1 Hz, 1H) 7.75-7.81 (m, 2H) 7.72 (dd, J=8.4, 2.1 Hz, 1H) 7.61 (d, J=8.4 Hz, 1H) 7.55 (s, 1H) 7.13-7.20 (m, 2H) 2.09-2.17 (m, 6H) 1.43-1.50 (m, 6H)

Scheme for the preparation of Examples 104 and 105:

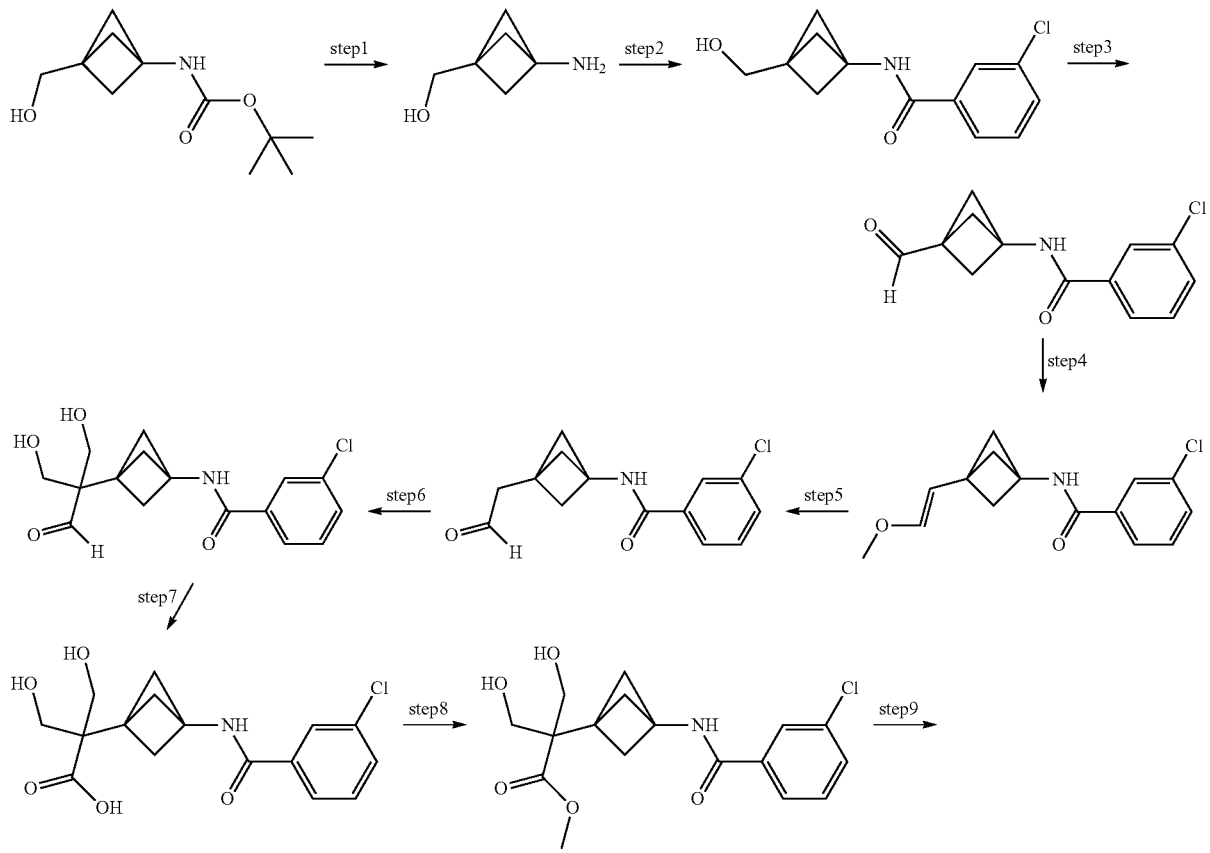

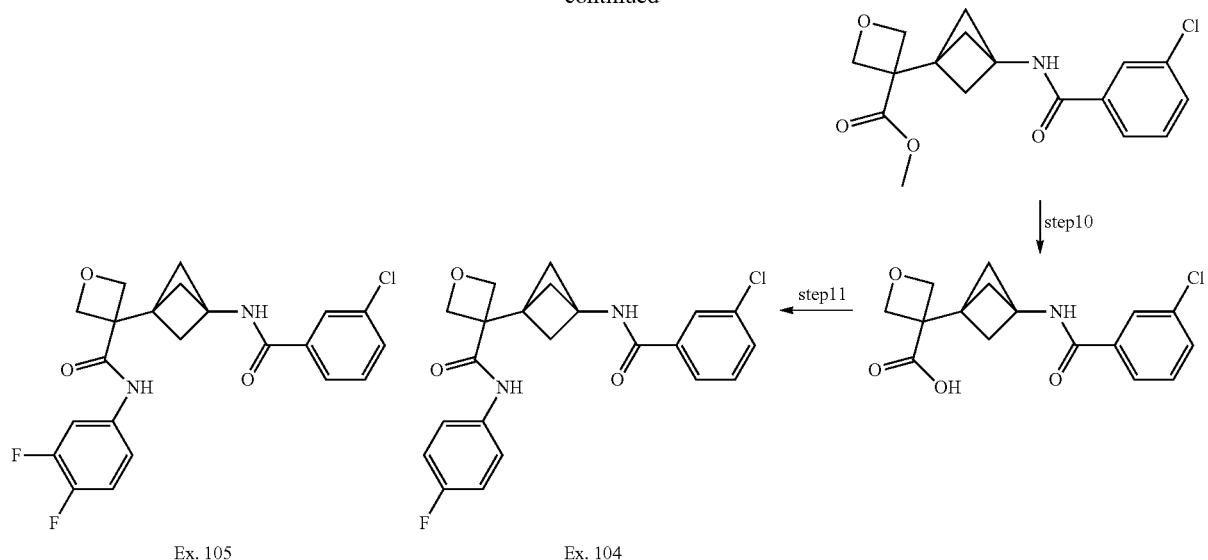

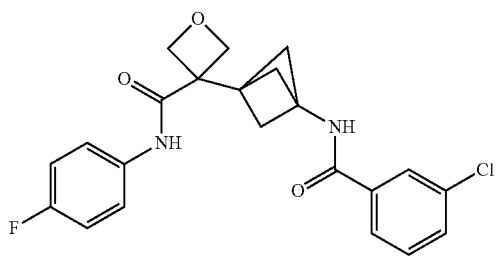 [SMILES: O=C(NC12CC(C3(C(=O)Nc4ccc(F)cc4)COC3)(C1)C2)c1cccc(Cl)c1]

Example 104. 3-(3-(3-Chlorobenzamido)bicyclo[1.1.1]pentan-1-yl)-N-(4-fluorophenyl)oxetane-3-carboxamide Step 1. (3-Aminobicyclo[1.1.1]pentan-1-yl)methanol, HCl Dissolved tert-butyl (3-(hydroxymethyl)bicyclo[1.1.1]pentan-1-yl)carbamate (500 mg, 2.344 mmol) in HCl (4.0 M in dioxane) (17.6 ml, 70.3 mmol). The mixture was stirred at RT for about 3 h. The mixture was concentrated in vacuo to give the desired product as a solid in quantitative yield. LCMS m/z (M+H) calc'd: 114.08; found 114.18 Step 2. 3-Chloro-N-(3-(hydroxymethyl)bicyclo[1.1.1]pentan-1-yl)benzamide To the stirred solution of 3-chlorobenzoic acid (328 mg, 2.093 mmol) and HATU (730 mg, 1.919 mmol) in DMF (4361 µl) were added DIEA (Aldrich) (1219 µl, 6.98 mmol) and (3-aminobicyclo[1.1.1]pentan-1-yl)methanol, HCl (261 mg, 1.744 mmol). The mixture was stirred at RT overnight. The mixture was diluted with EtOAc (30 ml), then washed with water (~10 ml). The aqueous was extracted with EtOAc (10 ml) for one more time. Organic phases were combined, dried over $Na_2SO_4$, filtered and concentrated. The residue was purified by Teledyne Isco system, using 40 g silica CombiFlash gold column and 0-100% EtOAc in hexane as eluting solvent, to afford the desired product as a solid. LCMS m/z (M+H) calc'd: 252.07; found (M+H): 252.09.

Step 3. 3-Chloro-N-(3-formylbicyclo[1.1.1]pentan-1-yl)benzamide

To the stirred solution of 3-chloro-N-(3-(hydroxymethyl)bicyclo[1.1.1]pentan-1-yl)benzamide (430 mg, 1.708 mmol) in anhydrous DCM (17.1 ml) were added pyridine (415 µl, 5.12 mmol) and Dess-Martin Periodinane (869 mg, 2.050 mmol) at 0° C. The mixture was slowly warmed up to RT and stirred at RT overnight. The reaction mixture was partitioned between EtOAc and water (150 ml:50 ml). The organic phase was separated and washed with 10% $Na_2S_2O_3$ aqueous (50 ml). The organic phase was separated, dried over $Na_2SO_4$, filtered and concentrated. The residue was then purified using Isco CombiFlash system and 0-100% EtOAc in hexane as an eluent to afford the desired product as a solid. LCMS m/z (M+H) calc'd: 250.06; found (M+H): 250.08; (M+H+H2O): 268.08.

Step 4. 3-Chloro-N-(3-(2-methoxyvinyl)bicyclo[1.1.1]pentan-1-yl)benzamide

To the stirred suspension of (methoxymethyl)triphenylphosphonium chloride (736 mg, 2.147 mmol) in anhydrous THF (4472 µl) was added potassium tert-butoxide (1.0 M in THF, Aldrich) (2080 µl, 2.080 mmol) dropwise at −55° C. The reaction was allowed to stir at −55° C. for 20 min, then warmed up to −30° C. over 30 min. To this mixture was slowly added 3-chloro-N-(3-formylbicyclo[1.1.1]pentan-1-yl)benzamide in THF (4472 µl) at this temperature. The reaction was allowed to stir for 30 min below −20° C., then slowly warmed up to RT, and stirred at RT for about 2 h. The reaction was monitored by LCMS and TLC until starting material was consumed, then quenched with addition of saturated ammonium chloride (20 ml) and diluted with ethyl acetate (50 ml). The aqueous was extracted with EtOAc for additional two times (50 ml×3). The organic phases were combined, dried over $Na_2SO_4$, filtered and concentrated. The residue was purified by column chromatography using Isco CombiFlash system, 40 g Isco RediSep silica gold column and 0-80% EtOAc in hexane as an eluent to give the desired product as a solid. LCMS m/z (M+H) calc'd: 278.09; found (M+H): 278.10.

Step 5. 3-Chloro-N-(3-(2-oxoethyl)bicyclo[1.1.1]pentan-1-yl)benzamide

To a stirred solution of (E)-3-chloro-N-(3-(2-methoxyvinyl)bicyclo[1.1.1]pentan-1-yl)benzamide (220 mg, 0.792 mmol) in acetone (8911 µl) and water (990 µl) was added p-toluenesulfonic acid monohydrate (196 mg, 1.030 mmol). The mixture was stirred at RT for 2 h. LCMS check showed reaction not completed. To the mixture was added more p-toluenesulfonic acid monohydrate (30.1 mg, 0.158 mmol). The mixture was stirred at room temperature overnight. The mixture was partitioned between EtOAc and water (20 ml:10 ml). The aqueous was extracted with EtOAc for three times. Organic phases were combined, dried over $Na_2SO_4$, filtered and concentrated in vacuo. The residue was purified by Teledyne Isco system, using 40 g silica CombiFlash gold column and 0-100% EtOAc in hexane as eluting solvent to give the desired product as a solid. LCMS m/z (M+H) calc'd: 264.07; found (M+H): 264.10.

Step 6. 3-Chloro-N-(3-(2-formyl-1,3-dihydroxypropan-2-yl)bicyclo[1.1.1]pentan-1-yl)benzamide To a stirred solution of 3-chloro-N-(3-(2-oxoethyl)bicyclo[1.1.1]pentan-1-yl)benzamide (127 mg, 0.482 mmol) in THF (2408 µl) were added trientyl amine (6.71 µl, 0.048 mmol); NaOH (1.0 M in water) (48.2 µl, 0.048 mmol) and formaldehyde (37% aqueous) (108 µl, 1.445 mmol). The mixture was stirred at RT overnight. LCMS showed desired product as the major product. To this mixture was added HCl (1.0 M in water) (96 µl, 0.096 mmol) to adjust the pH~7, then the mixture was evaporated to dryness to give the desired product as a solid, which was used as in the next step. LCMS m/z (M+H) calc'd: 324.09; found (M+H): 324.11.

Step 7. 2-(3-(3-Chlorobenzamido)bicyclo[1.1.1]pentan-1-yl)-3-hydroxy-2-(hydroxymethyl)propanoic Acid To a stirred solution of 3-chloro-N-(3-(2-formyl-1,3-dihydroxypropan-2-yl)bicyclo[1.1.1]pentan-1-yl)benzamide (0.156 g, 0.482 mmol) in THF (7.71 ml) and water (1.928 ml) were added sulfamic acid (0.140 g, 1.446 mmol) and sodium chloride (0.065 g, 0.578 mmol) at 0° C. The mixture was stirred at 0° C. for 5 min, then potassium dihydrogen phosphate (0.394 g, 2.89 mmol) was added. The mixture was stirred at RT for 60 min, LCMS monitored until the aldehyde was consumed. To the mixture was added EtOAc (15 ml) and water (5 ml). The aqueous was extracted with EtOAc for three times (15 ml×3). Organic phases were combined, washed with sat. NaCl (~5 ml), separated, dried over $Na_2SO_4$ and then filtered. The filtrate was concentrated in vacuo to give the desired product as a solid, which was used as in the next step. LCMS m/z (M+H) calc'd: 340.09; found (M+H): 340.22.

Step 8. Methyl 2-(3-(3-chlorobenzamido)bicyclo[1.1.1]pentan-1-yl)-3-hydroxy-2-(hydroxymethyl)propanoate To a stirred solution of 2-(3-(3-chlorobenzamido)bicyclo[1.1.1]pentan-1-yl)-3-hydroxy-2-(hydroxymethyl)propanoic acid (164 mg, 0.482 mmol) in DCM (2008 µl) and MeOH (2008 µl) was added TMS-Diazomethane (2.0 M in hexane) (Aldrich) (482 µl, 0.964 mmol) at 0° C. The mixture was stirred at RT for about 60 min. LCMS check reaction completed and the desired product as the major product. The mixture was concentrated, and the residue was purified by reversed HPLC using Isco CombiFlash system and Isco RediSep C18 gold column (50 g) and 0-100% acetonitrile-water to give the desired product as a solid after lyophilization. LCMS m/z (M+H) calc'd: 354.10; found (M+H): 354.15.

Step 9. Methyl 3-(3-(3-chlorobenzamido)bicyclo[1.1.1]pentan-1-yl)oxetane-3-carboxylate To the stirred solution of methyl 2-(3-(3-chlorobenzamido)bicyclo[1.1.1]pentan-1-yl)-3-hydroxy-2-(hydroxymethyl)propanoate (51 mg, 0.144 mmol), zinc dimethyldithiocarbamate (57.3 mg, 0.187 mmol) and triphenylphosphine (49.2 mg, 0.187 mmol) in anhydrous THF (1442 µl) was added DEAD (40% in toluene, Aldrich) (85 µl, 0.187 mmol) at 0° C. The mixture was stirred at RT overnight. LCMS check showed desired product, and no more starting material. The mixture was diluted with EtOAc (~10 ml) and filtered. The filtrate was concentrated and purified on silica gel column (ISCO gold 12 g) using 0-100% EtOAc/hexane as eluting solvent to give the desired product as a solid. LC-Mass m z (M+H) calc'd: 336.09; found (M+H): 336. 09.

Step 10. 3-(3-(3-Chlorobenzamido)bicyclo[1.1.1]pentan-1-yl)oxetane-3-carboxylic Acid To the stirred solution of methyl 3-(3-(3-chlorobenzamido)bicyclo[1.1.1]pentan-1-yl)oxetane-3-carboxylate (50 mg, 0.149 mmol) in THF (567 µl) were added water (142 µl), MeOH (284 µl) and sodium hydroxide (2.0 M in water) (Aldrich) (298 µl, 0.596 mmol) at RT. The mixture was stirred at RT for about 1.5 h. LCMS monitored. The reaction was quenched with addition of HCl (6.0 M in water) (Aldrich) (99 µl, 0.596 mmol) (to make pH~6-7), then the mixture was partitioned between EtOAc (10 ml) and sat. NaCl (~2 ml). The aqueous was extracted with EtOAc for one more time (10 ml), and organic phases were combined, dried over $Na_2SO_4$, filtered and concentrated in vacuo to give the desired product as a solid. LC-Mass m z (M+H) calc'd: 322.08; found (M+H): 322.10.

Step 11. 3-(3-(3-Chlorobenzamido)bicyclo[1.1.1]pentan-1-yl)-N-(4-fluorophenyl)oxetane-3-carboxamide To the stirred solution of 3-(3-(3-chlorobenzamido)bicyclo[1.1.1]pentan-1-yl)oxetane-3-carboxylic acid (20 mg, 0.062 mmol) and HATU (26.0 mg, 0.068 mmol) in DMF (777 µl) were added DIEA (32.6 µl, 0.186 mmol) and 4-fluoroaniline (11.81 µl, 0.124 mmol). The mixture was stirred at RT overnight. LCMS showed desired product as the major product. The mixture was diluted with DMSO (0.5 ml) and purified by the mass-directed reverse phase HPLC purification using the following condition: Reverse HPLC on a 19×100 mm, Waters CSH C18 column, 5µ particle size, flow rate 25 ml/min, linear gradient, 30% ACN/$H_2O$ to 65% ACN/$H_2O$, total run time 12 mins, buffering with 0.16% TFA. The final purified product was collected as a solid after lyophilization.

LCMS m/z (M+H) calc'd: 415.11; found (M+H): 415.27.
$^1$H NMR (500 MHz, $CD_3OD$): δ 7.83-7.82 (m, 1H); 7.74 (d, J=7.5 Hz, 1H); 7.59-7.53 (m, 3H); 7.45 (t, J=7.5 Hz, 1H); 7.09 (t, J=7.5 Hz, 2H); 4.95 (d, J=5 Hz, 2H); 4.63 (d, J=5 Hz, 2H); 2.25 (s, 6H) Example 105. 3-(3-(3-Chlorobenzamido)bicyclo[1.1.1]pentan-1-yl)-N-(3,4-difluorophenyl)oxetane-3-carboxamide

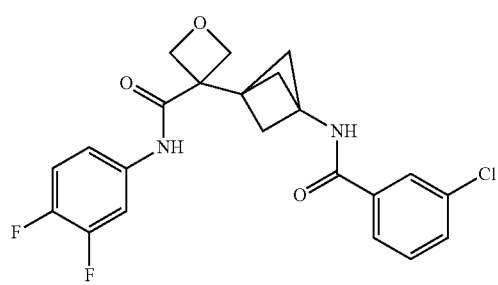 [SMILES: O=C(NC12CC(C3(C(=O)Nc4ccc(F)c(F)c4)COC3)(C1)C2)c1cccc(Cl)c1]

The title compound was synthesized following the procedures described in Example 104 except that in the final step 3,4-difluoroaniline was used in place of 4-fluoroaniline. LCMS m/z (M+H) calc'd: 433.11; found (M+H): 433.26. $^1$H NMR (500 MHz, CD$_3$OD): 7.83-7.82 (m, 1H); 7.74 (d, J=7.5 Hz, 1H); 7.72-7.68 (m, 1H); 7.55 (d, J=10 Hz, 1H); 7.45 (t, J 10 Hz, 1H); 7.31-7.22 (m, 2H); 4.94 (d, J=5 Hz, 2H); 4.62 (d, J=5 Hz, 2H); 2.24 (s, 6H)

The compounds in Table 10 were prepared in a similar way as Example 104 except that 3,4-difluorobenzoyl chloride is used in Step 2, and the general Scheme is as shown below:

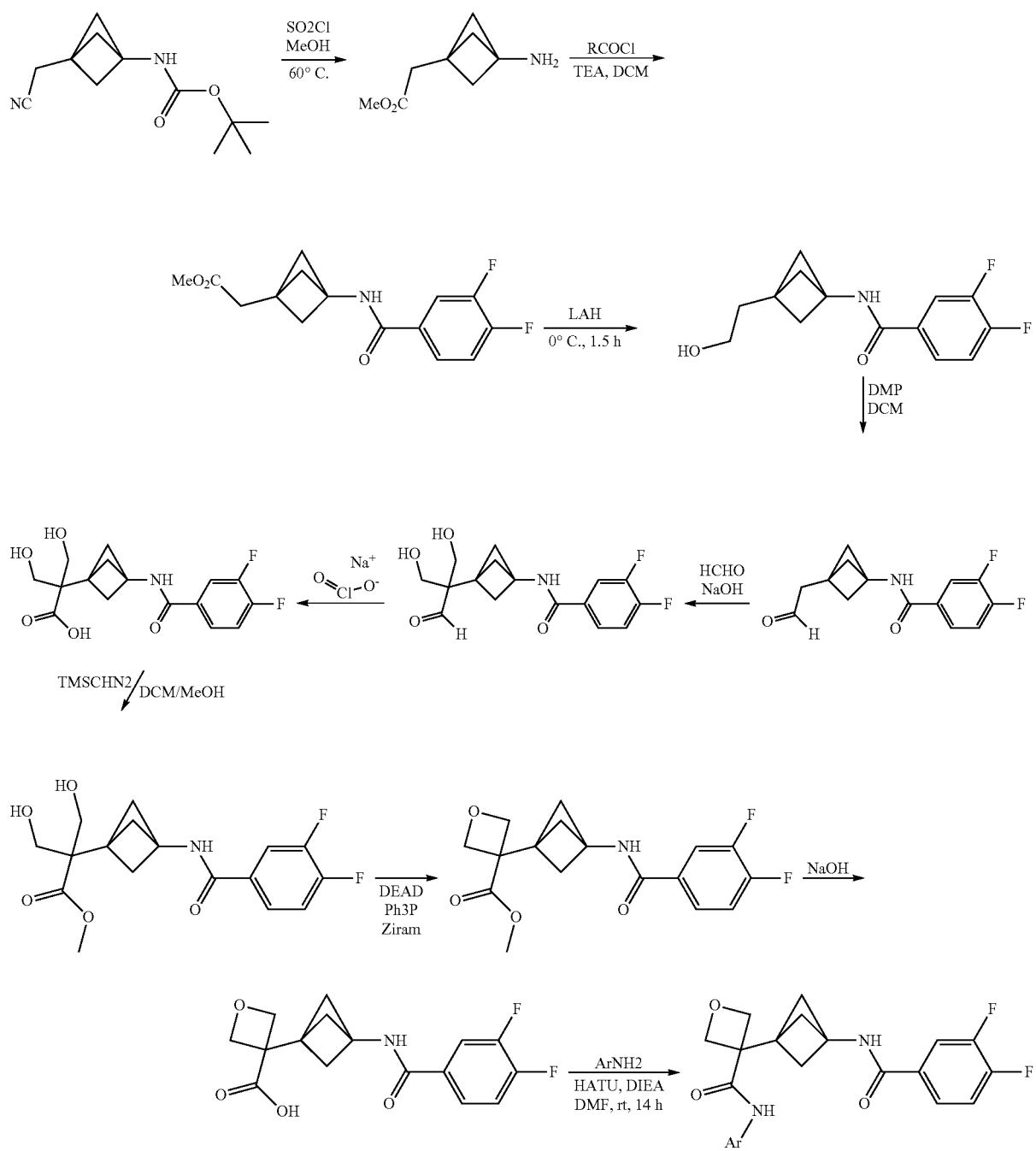

TABLE 10

| Ex. # | Structure | Chemical Name | Mass [M + H]+ |
|---|---|---|---|
| 106 | 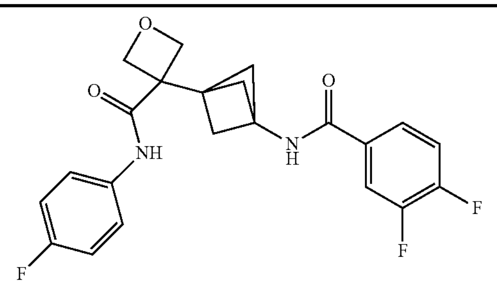 | 3-(3-(3,4-difluorobenzamido)bicyclo[1.1.1]pentan-1-yl)-N-(4-fluorophenyl)oxetane-3-carboxamide | 417.18 |
| 107 | 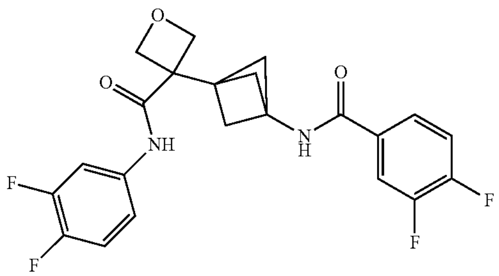 [SMILES: O=C(NC12CC(C3(C(=O)Nc4ccc(F)c(F)c4)COC3)(C1)C2)c1ccc(F)c(F)c1] | 3-(3-(3,4-difluorobenzamido)bicyclo[1.1.1]pentan-1-yl)-N-(3,4-difluorophenyl)oxetane-3-carboxamide | 435.27 |

Example 108. N-(4-Chlorophenyl)-3-(3-(3,4-difluorobenzamido)bicyclo[1.1.1]pentan-1-yl)oxetane-3-carboxamide

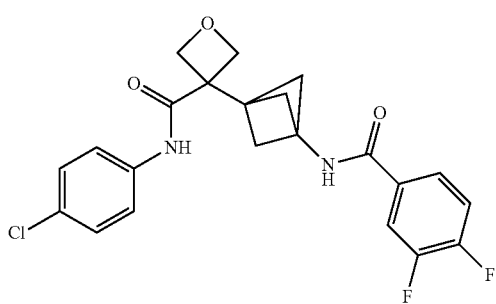 [SMILES: O=C(NC12CC(C3(C(=O)Nc4ccc(Cl)cc4)COC3)(C1)C2)c1ccc(F)c(F)c1]

Step 1. Methyl 2-(3-aminobicyclo[1.1.1]pentan-1-yl)acetate, HCl

To a stirred solution of dry methanol (36.4 ml, 900 mmol) in a vial was added thionyl chloride (1970 µl, 27.0 mmol) dropwise, followed by addition of tert-butyl (3-(cyanomethyl)bicyclo[1.1.1]pentan-1-yl)carbamate (1000 mg, 4.50 mmol). The mixture was brought to 60° C. and stirred at 60° C. overnight. The mixture was cooled to RT, and evaporated to dryness to give the title compound as a solid. LCMS m/z (M+H) calc'd: 156.09; found (M+H): 156.15.

Step 2. Methyl 2-(3-(3,4-difluorobenzamido)bicyclo [1.1.1]pentan-1-yl)acetate

To the stirred solution of methyl 2-(3-aminobicyclo[1.1.1]pentan-1-yl)acetate, HCl (504 mg, 2.63 mmol) in CH₂C₂ (13.1 ml) were added TEA (1466 µl, 10.52 mmol) and 3,4-difluorobenzoyl chloride (431 µl, 3.42 mmol) at 0° C. The mixture was then stirred at RT overnight. The mixture was purified by Teledyne Isco system, using 80 g silica CombiFlash gold column and 0-100% EtOAc in hexane as eluting solvent to afford the title compound as a solid. LCMS m/z (M+H) calc'd: 296.10; found (M+H): 296.19.

Step 3. 3,4-Difluoro-N-(3-(2-hydroxyethyl)bicyclo [1.1.1]pentan-1-yl)benzamide

To a stirred solution of methyl 2-(3-(3,4-difluorobenzamido)bicyclo[1.1.1]pentan-1-yl)acetate (450 mg, 1.524 mmol) in dry THF (15.2 ml) was added LAH (1.0 M in THF) (1753 µl, 1.753 mmol) at –0° C. under N₂ atmosphere. The mixture was stirred at –0° C. under N₂ atmosphere for about 1.5 h. The resulting reaction mixture was quenched with addition of sat. NH₄Cl dropwise (~10 ml), and then partitioned between EtOAc (50 ml) and sat. NH₄Cl/1N HCl (10 ml:10 ml). The aqueous was extracted with EtOAc for two times (50 ml×2). The organic phases were separated, combined, dried over Na₂SO₄, filtered, and concentrated in vacuo to afford the title compound as a solid. LCMS m/z (M+H) calc'd: 268.11; found (M+H):268.23.

Step 4. 3,4-Difluoro-N-(3-(2-oxoethyl)bicyclo [1.1.1]pentan-1-yl)benzamide

To the stirred solution of 3,4-difluoro-N-(3-(2-hydroxyethyl)bicyclo[1.1.1]pentan-1-yl)benzamide (407 mg, 1.523 mmol) in DCM (1.52E+04 µl) was added Dess-MartinPeriodinane (710 mg, 1.675 mmol) at 0° C. The mixture was slowly warmed up to RT and stirred at RT for 60 min. The mixture was then purified using Isco CombiFlash system, using 80 g silica CombiFlash gold column and 0-100% EtOAc in hexane as eluting solvent to afford the title compound as a solid. LCMS m/z (M+H) calc'd: 266.09; found (M+H): 266.21.

Step 5. 3,4-Difluoro-N-(3-(2-formyl-1,3-dihydroxypropan-2-yl)bicyclo[1.1.1]pentan-1-yl)benzamide To a stirred solution of 3,4-difluoro-N-(3-(2-oxoethyl) bicyclo[1.1.1]pentan-1-yl)benzamide (400 mg, 1.508 mmol)

in THF (7540 μl) were added TEA (21.02 μl, 0.151 mmol); NaOH (2.0 M in water) (151 μl, 0.302 mmol) and formaldehyde (37% aqueous) (337 μl, 4.52 mmol). The mixture was stirred at RT overnight. To the mixture was added HCl (1.0 M in water) (~75 μl, 0.452 mmol) to make the pH~7, then the mixture was evaporated to dryness to give the crude title compound as a solid, which was used as is in next step. LCMS m/z (M+H) calc'd: 326.11; found (M+H): 326.13.

Step 6. 2-(3-(3,4-Difluorobenzamido)bicyclo[1.1.1]pentan-1-yl)-3-hydroxy-2-(hydroxymethyl)propanoic Acid To a stirred solution of 3,4-difluoro-N-(3-(2-formyl-1,3-dihydroxypropan-2-yl)bicyclo[1.1.1]pentan-1-yl)benzamide (0.491 g, 1.508 mmol) in THF (20.11 ml) and water (5.03 ml) were added sulfamic acid (0.439 g, 4.52 mmol) and sodium chloride (0.205 g, 1.810 mmol) at 0° C. The mixture was stirred at 0° C. for 5 min, then added potassium dihydrogen phosphate (1.231 g, 9.05 mmol). The mixture was stirred at RT for about 1 h. LCMS monitored. To the mixture was added EtOAc (50 ml) and water (15 ml). The aqueous was extracted with EtOAc for three times (50 ml×3). Organic phases were combined, washed with sat. NaCl (~15 ml), separated and dried over Na$_2$SO$_4$, then filtered. The filtrate was concentrated in vacuo to give the crude title compound as a solid, which was used as is in the next step.
LCMS m/z (M+H) calc'd: 342.11; found (M+H): 342.15.

Step 7. Methyl 2-(3-(3,4-difluorobenzamido)bicyclo[1.1.1]pentan-1-yl)-3-hydroxy-2-(hydroxymethyl) propanoate To a stirred solution of 2-(3-(3,4-difluorobenzamido)bicyclo[1.1.1]pentan-1-yl)-3-hydroxy-2-(hydroxymethyl)propanoic acid (515 mg, 1.508 mmol) in MeOH (9425 μl) and DCM (9425 μl) were added TMS-Diazomethane (2.0 M in hexane) (1508 μl, 3.02 mmol) dropwise at 0° C. The mixture was stirred at RT for about 2 h. LCMS monitored. The reaction was then quenched with addition of acetic acid (86 μl, 1.508 mmol), and then concentrated. The residue was purified by Teledyne Isco system, 40 g silica CombiFlash gold column and 0-100% EtOAc in hexane as eluting solvent to give the title compound as a solid. LCMS m/z (M+H) calc'd: 356.12; found (M+H): 356.12.

Step 8. Methyl 3-(3-(3,4-difluorobenzamido)bicyclo[1.1.1]pentan-1-yl)oxetane-3-carboxylate To the stirred suspension of methyl 2-(3-(3,4-difluorobenzamido)bicyclo[1.1.1]pentan-1-yl)-3-hydroxy-2-(hydroxymethyl)propanoate (310 mg, 0.872 mmol), zinc dimethyl dithiocarbamate (TCI) (347 mg, 1.134 mmol) and triphenyl phosphine (297 mg, 1.134 mmol) in THF (8724 μl) was added DEAD (40% in toluene) (517 μl, 1.134 mmol) at 0° C. The mixture was stirred at RT overnight. The mixture was diluted with EtOAc (~50 ml) and filtered. The filtrate was concentrated and purified by Isco system on IscoCombi Flash silica gold column (40 g) using 0-100% EtOAc/hexane as eluting solvent to afford the title compound as a solid. LCMS m/z (M+H) calc'd: 338.11; found (M+H): 338.09.

Step 9. 3-(3-(3,4-Difluorobenzamido)bicyclo[1.1.1]pentan-1-yl)oxetane-3-carboxylic Acid To the stirred solution of methyl 3-(3-(3,4-difluorobenzamido)bicyclo[1.1.1]pentan-1-yl)oxetane-3-carboxylate (269 mg, 0.797 mmol) in THF (3038 μl) and MeOH (1519 μl) were added water (759 μl) and sodium hydroxide (2.0 M in water) (1595 μl, 3.19 mmol) at RT. The mixture was stirred at RT for about 1.5 h until the starting material was consumed. LCMS monitored. The reaction was quenched with addition of HCl (6.0 M in water) (~532 μl, 3.19 mmol) to make pH~6-7, then the mixture was partitioned between EtOAc (30 ml) and sat. NaCl (~10 ml). The aqueous was extracted with EtOAc for one more time (30 ml). Organic phases were combined, dried over Na$_2$SO$_4$, filtered and concentrated in vacuo to give the title product as a solid. LCMS m/z (M+H) calc'd: 324.10; found (M+H): 324.12.

Step 10. N-(4-Chlorophenyl)-3-(3-(3,4-difluorobenzamido)bicyclo[1.1.1]pentan-1-yl)oxetane-3-carboxamide To the stirred solution of 3-(3-(3,4-difluorobenzamido)bicyclo[1.1.1]pentan-1-yl)oxetane-3-carboxylic acid (30 mg, 0.093 mmol) and HATU (Aldrich) (38.8 mg, 0.102 mmol) in DMF (1160 μl) were added DIEA (Aldrich) (48.6 μl, 0.278 mmol) and 4-chloroaniline (23.68 mg, 0.186 mmol). The mixture was stirred at RT overnight. LCMS showed desired product as the major product. The mixture was diluted with DMSO (0.5 ml) and purified by the mass-directed reverse phase HPLC purification using the following condition (Reverse HPLC on a 19×100 mm, Waters CSH C18 column, 5μ particle size, flow rate 25 ml/min, linear gradient, 30% ACN/H$_2$O to 65% ACN/H$_2$O, total run time 12 min, buffering with 0.16% TFA), followed by lyophilization to give the title compound as a solid. LCMS m/z (M+H) calc'd: 433.11; found (M+H): 433.26. $^1$H NMR (500 MHz, CD$_3$OD): 7.77-7.72 (m, 1H); 7.68-7.65 (m, 1H); 7.59 (d, J 8.9 Hz, 2H); 7.38-7.36 (m, 1H); 7.34 (d, J=8.9 Hz, 2H); 4.94 (d, J=6.4 Hz, 2H); 4.62 (d, J=6.4 Hz, 2H); 2.24 (s, 6H)

The compounds in Table 11 were prepared by parallel synthesis according to the below general procedure. The starting 2-(3-aminobicyclo[1.1.1]pentan-1-yl)-N-(4-fluorophenyl)propanamide was obtained from tert-butyl (3-(1-((4-fluorophenyl)amino)-1-oxopropan-2-yl)bicyclo[1.1.1]pentan-1-yl)carbamate by tert-butoxycarbonyl deprotection in a similar fashion to that shown for Example 33, Step 1A). The carboxylic acids used were commercially available.

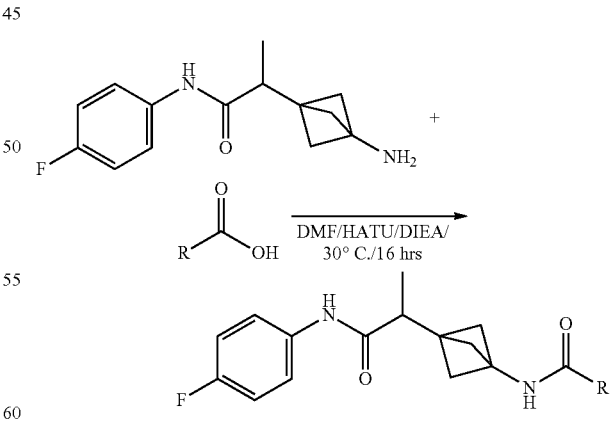

A 0.24 M HATU solution in DMF was prepared. In an 8 mL vial was added 2-(3-aminobicyclo [1.1.1] pentan-b-yl)-N-(4-fluorophenyl) propanamide (9.93 mg, 40 mol, 1 eq.), carboxylic acid monomers (80 μmol, 2.0 eq.), and N, N-diisopropylethylamine (15.5 mg, 120 μmol, 3.0 eq.) in DMF (200 μL) to give a reaction mixture. Then 200 μL solution of HATU (48 µmol, 1.2 eq.) was added to the reaction vials above. The vials were capped and shaken at 30° C. for 16 h. After the reactions were completed, the reaction mixtures were concentrated by Speedvac. The residue was dissolved in ACN/H₂O and purified by preparative HPLC to give pure final product.

TABLE 11

| Ex. # | Structure | Chemical Name | Mass [M + H]+ |
|---|---|---|---|
| 109 | 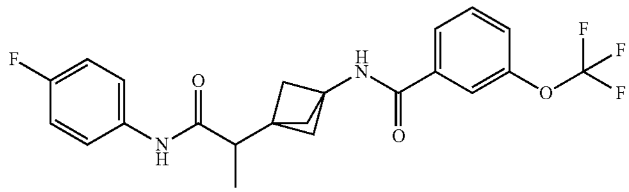 [SMILES: CC(C(=O)Nc1ccc(F)cc1)C12CC(NC(=O)c3cccc(OC(F)(F)F)c3)(C1)C2] | N-[3-[2-(4-fluoroanilino)-1-methyl-2-oxo-ethyl]-1-bicyclo[1.1.1]pentanyl]-3-(trifluoromethoxy)benzamide | 437 |
| 110 | 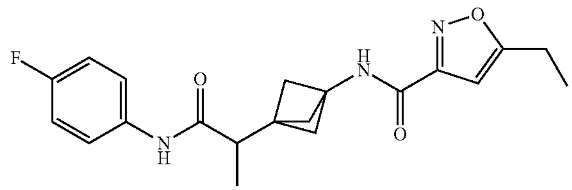 [SMILES: CCc1cc(C(=O)NC23CC(C(C)C(=O)Nc4ccc(F)cc4)(C2)C3)no1] | 5-ethyl-N-[3-[2-(4-fluoroanilino)-1-methyl-2-oxo-ethyl]-1-bicyclo[1.1.1]pentanyl]isoxazole-3-carboxamide | 372 |
| 111 | 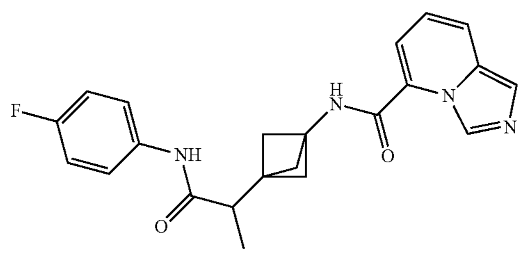 [SMILES: CC(C(=O)Nc1ccc(F)cc1)C12CC(NC(=O)c3cccc4cncn34)(C1)C2] | N-[3-[2-(4-fluoroanilino)-1-methyl-2-oxo-ethyl]-1-bicyclo[1.1.1]pentanyl]imidazo[1,5-a]pyridin-2-ium-5-carboxamide | 393 |
| 112 | 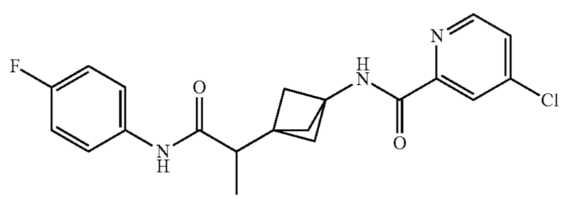 [SMILES: CC(C(=O)Nc1ccc(F)cc1)C12CC(NC(=O)c3cc(Cl)ccn3)(C1)C2] | 4-chloro-N-[3-[2-(4-fluoroanilino)-1-methyl-2-oxo-ethyl]-1-bicyclo[1.1.1]pentanyl]pyridin-1-ium-2-carboxamide | 388 |
| 113 | 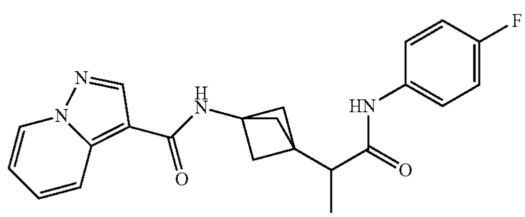 [SMILES: CC(C(=O)Nc1ccc(F)cc1)C12CC(NC(=O)c3cnn4ccccc34)(C1)C2] | N-[3-[2-(4-fluoroanilino)-1-methyl-2-oxo-ethyl]-1-bicyclo[1.1.1]pentanyl]pyrazolo[1,5-a]pyridin-1-ium-3-carboxamide | 393 |
| 114 | 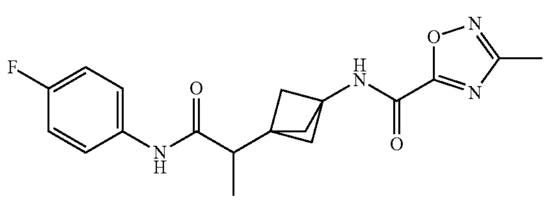 [SMILES: Cc1noc(C(=O)NC23CC(C(C)C(=O)Nc4ccc(F)cc4)(C2)C3)n1] | N-[3-[2-(4-fluoroanilino)-1-methyl-2-oxo-ethyl]-1-bicyclo[1.1.1]pentanyl]-3-methyl-1,2,4-oxadiazole-5-carboxamide | 359 |
| 115 | 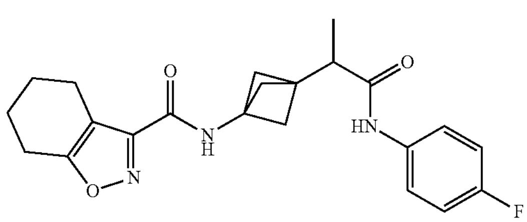 [SMILES: CC(C(=O)Nc1ccc(F)cc1)C12CC(NC(=O)c3noc4c3CCCC4)(C1)C2] | N-[3-[2-(4-fluoroanilino)-1-methyl-2-oxo-ethyl]-1-bicyclo[1.1.1]pentanyl]-4,5,6,7-tetrahydro-1,2-benzoxazole-3-carboxamide | 398 |

TABLE 11-continued

| Ex. # | Structure | Chemical Name | Mass [M + H]+ |
|---|---|---|---|
| 116 | 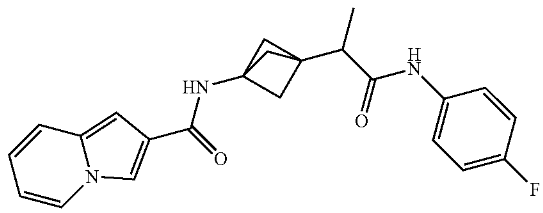 [SMILES: CC(C(=O)Nc1ccc(F)cc1)C12CC(NC(=O)c3cc4ccccn4c3)(C1)C2] | N-[3-[2-(4-fluoroanilino)-1-methyl-2-oxo-ethyl]-1-bicyclo[1.1.1]pentanyl]indolizine-2-carboxamide | 392 |
| 117 | 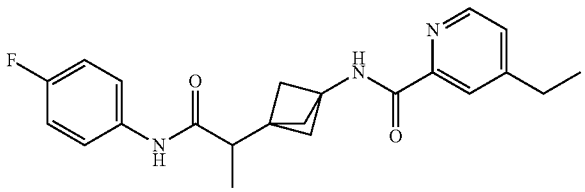 [SMILES: CCc1ccnc(C(=O)NC23CC(C(C)C(=O)Nc4ccc(F)cc4)(C2)C3)c1] | 4-ethyl-N-[3-[2-(4-fluoroanilino)-1-methyl-2-oxo-ethyl]-1-bicyclo[1.1.1]pentanyl]pyridin-1-ium-2-carboxamide | 382 |
| 118 | 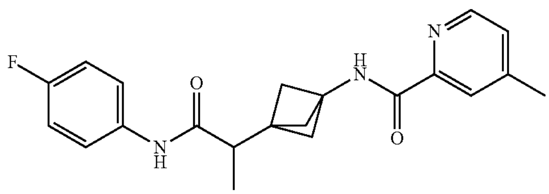 [SMILES: Cc1ccnc(C(=O)NC23CC(C(C)C(=O)Nc4ccc(F)cc4)(C2)C3)c1] | N-[3-[2-(4-fluoroanilino)-1-methyl-2-oxo-ethyl]-1-bicyclo[1.1.1]pentanyl]-4-methyl-pyridin-1-ium-2-carboxamide | 368 |
| 119 | 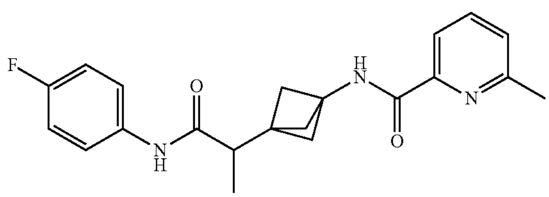 [SMILES: Cc1cccc(C(=O)NC23CC(C(C)C(=O)Nc4ccc(F)cc4)(C2)C3)n1] | N-[3-[2-(4-fluoroanilino)-1-methyl-2-oxo-ethyl]-1-bicyclo[1.1.1]pentanyl]-6-methyl-pyridin-1-ium-2-carboxamide | 368 |
| 120 | 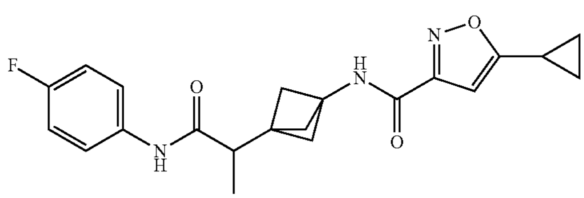 [SMILES: CC(C(=O)Nc1ccc(F)cc1)C12CC(NC(=O)c3cc(C4CC4)on3)(C1)C2] | 5-cyclopropyl-N-[3-[2-(4-fluoroanilino)-1-methyl-2-oxo-ethyl]-1-bicyclo[1.1.1]pentanyl]isoxazole-3-carboxamide | 384 |
| 121 | 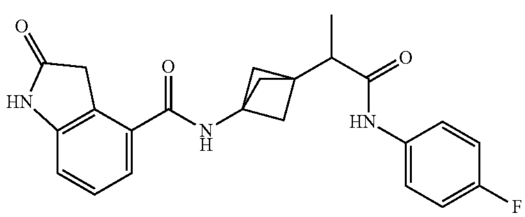 [SMILES: CC(C(=O)Nc1ccc(F)cc1)C12CC(NC(=O)c3cccc4c3CC(=O)N4)(C1)C2] | N-[3-[2-(4-fluoroanilino)-1-methyl-2-oxo-ethyl]-1-bicyclo[1.1.1]pentanyl]-2-oxo-indoline-4-carboxamide | 408 |
| 122 | 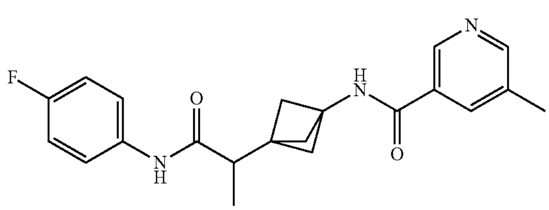 [SMILES: Cc1cncc(C(=O)NC23CC(C(C)C(=O)Nc4ccc(F)cc4)(C2)C3)c1] | N-[3-[2-(4-fluoroanilino)-1-methyl-2-oxo-ethyl]-1-bicyclo[1.1.1]pentanyl]-5-methyl-pyridin-1-ium-3-carboxamide | 368 |

TABLE 11-continued

| Ex. # | Structure | Chemical Name | Mass [M + H]+ |
|---|---|---|---|
| 123 | 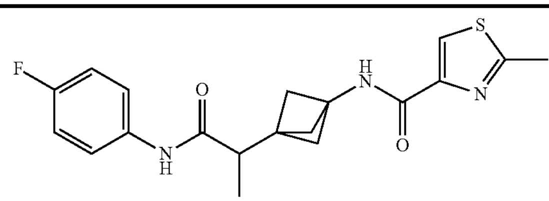 | N-[3-[2-(4-fluoroanilino)-1-methyl-2-oxo-ethyl]-1-bicyclo[1.1.1]pentanyl]-2-methyl-thiazole-4-carboxamide | 374 |
| 124 | 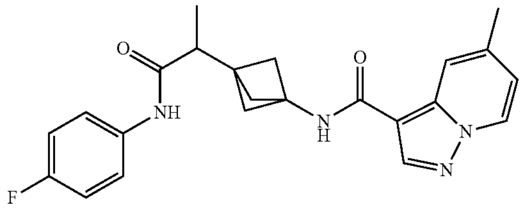 [SMILES: Cc1ccn2ncc(C(=O)NC34CC(C(C)C(=O)Nc5ccc(F)cc5)(C3)C4)c2c1] | N-[3-[2-(4-fluoroanilino)-1-methyl-2-oxo-ethyl]-1-bicyclo[1.1.1]pentanyl]-5-methyl-pyrazolo[1,5-a]pyridin-1-ium-3-carboxamide | 407 |
| 125 | 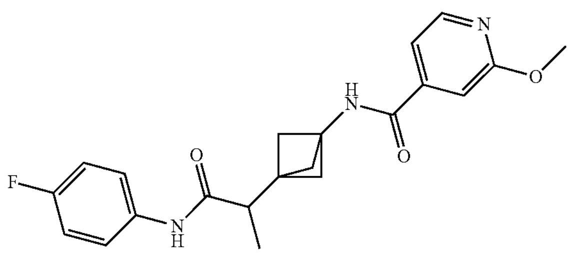 [SMILES: COc1cc(C(=O)NC23CC(C(C)C(=O)Nc4ccc(F)cc4)(C2)C3)ccn1] | N-[3-[2-(4-fluoroanilino)-1-methyl-2-oxo-ethyl]-1-bicyclo[1.1.1]pentanyl]-2-methoxy-pyridin-1-ium-4-carboxamide | 384 |
| 126 | 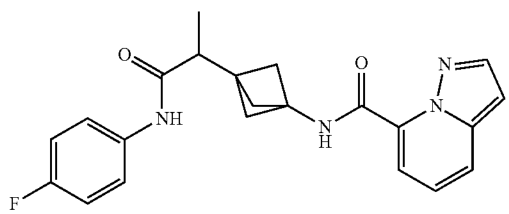 [SMILES: CC(C(=O)Nc1ccc(F)cc1)C12CC(NC(=O)c3cccc4ccnn34)(C1)C2] | N-[3-[2-(4-fluoroanilino)-1-methyl-2-oxo-ethyl]-1-bicyclo[1.1.1]pentanyl]pyrazolo[1,5-a]pyridin-1-ium-7-carboxamide | 393 |
| 127 | 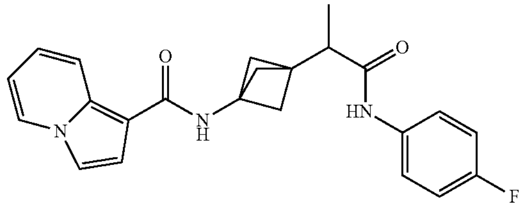 [SMILES: CC(C(=O)Nc1ccc(F)cc1)C12CC(NC(=O)c3ccn4ccccc34)(C1)C2] | N-[3-[2-(4-fluoroanilino)-1-methyl-2-oxo-ethyl]-1-bicyclo[1.1.1]pentanyl]indolizine-1-carboxamide | 392 |
| 128 | 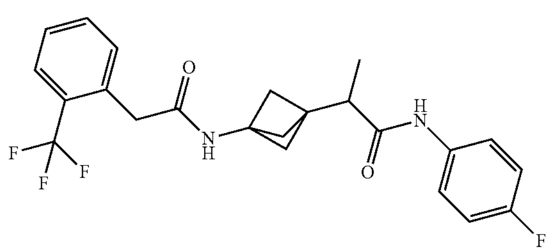 [SMILES: CC(C(=O)Nc1ccc(F)cc1)C12CC(NC(=O)Cc3ccccc3C(F)(F)F)(C1)C2] | N-(4-fluorophenyl)-2-[3-[[2-[2-(trifluoromethyl)phenyl]acetyl]amino]-1-bicyclo[1.1.1]pentanyl]propanamide | 435 |
| 129 | 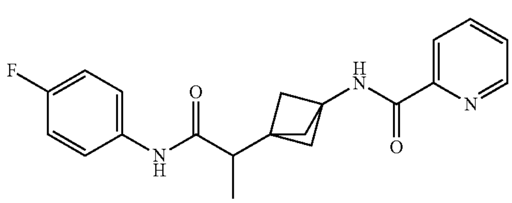 [SMILES: CC(C(=O)Nc1ccc(F)cc1)C12CC(NC(=O)c3ccccn3)(C1)C2] | N-[3-[2-(4-fluoroanilino)-1-methyl-2-oxo-ethyl]-1-bicyclo[1.1.1]pentanyl]pyridin-1-ium-2-carboxamide | 354 |

TABLE 11-continued

| Ex. # | Structure | Chemical Name | Mass [M + H]+ |
|---|---|---|---|
| 130 | 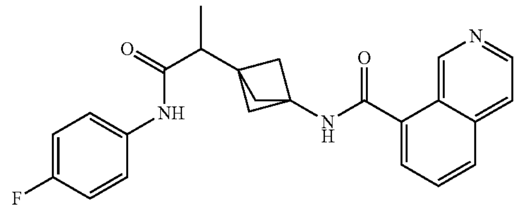 [SMILES: CC(C(=O)Nc1ccc(F)cc1)C12CC(NC(=O)c3cccc4ccncc34)(C1)C2] | N-[3-[2-(4-fluoroanilino)-1-methyl-2-oxo-ethyl]-1-bicyclo[1.1.1]pentanyl]isoquinolin-2-ium-8-carboxamide | 404 |
| 131 | 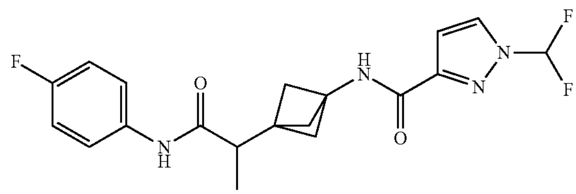 [SMILES: CC(C(=O)Nc1ccc(F)cc1)C12CC(NC(=O)c3ccn(C(F)F)n3)(C1)C2] | 1-(difluoromethyl)-N-[3-[2-(4-fluoroanilino)-1-methyl-2-oxo-ethyl]-1-bicyclo[1.1.1]pentanyl]pyrazole-3-carboxamide | 393 |
| 132 | 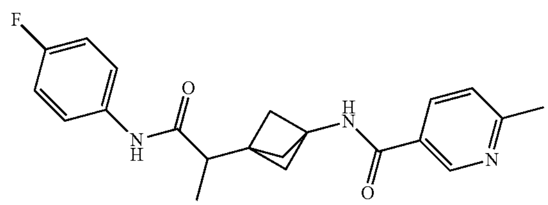 [SMILES: Cc1ccc(C(=O)NC23CC(C(C)C(=O)Nc4ccc(F)cc4)(C2)C3)cn1] | N-[3-[2-(4-fluoroanilino)-1-methyl-2-oxo-ethyl]-1-bicyclo[1.1.1]pentanyl]-6-methyl-pyridin-1-ium-3-carboxamide | 368 |
| 133 | 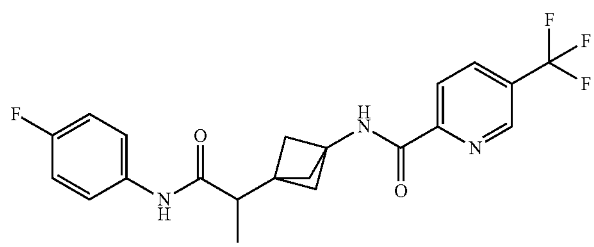 [SMILES: CC(C(=O)Nc1ccc(F)cc1)C12CC(NC(=O)c3ccc(C(F)(F)F)cn3)(C1)C2] | N-[3-[2-(4-fluoroanilino)-1-methyl-2-oxo-ethyl]-1-bicyclo[1.1.1]pentanyl]-5-(trifluoromethyl)pyridin-1-ium-2-carboxamide | 422 |
| 134 | 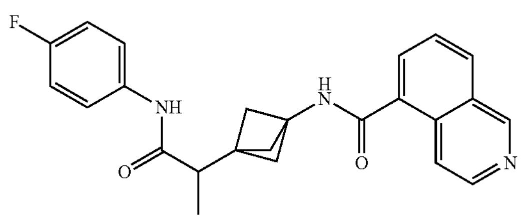 [SMILES: CC(C(=O)Nc1ccc(F)cc1)C12CC(NC(=O)c3cccc4cnccc34)(C1)C2] | N-[3-[2-(4-fluoroanilino)-1-methyl-2-oxo-ethyl]-1-bicyclo[1.1.1]pentanyl]isoquinolin-2-ium-5-carboxamide | 404 |
| 135 | 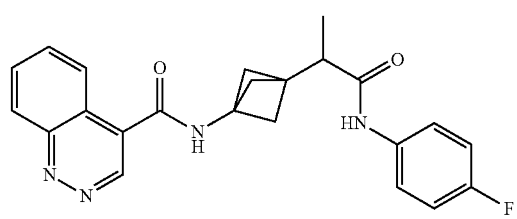 [SMILES: CC(C(=O)Nc1ccc(F)cc1)C12CC(NC(=O)c3cnnc4ccccc34)(C1)C2] | N-[3-[2-(4-fluoroanilino)-1-methyl-2-oxo-ethyl]-1-bicyclo[1.1.1]pentanyl]cinnoline-4-carboxamide | 405 |
| 136 | 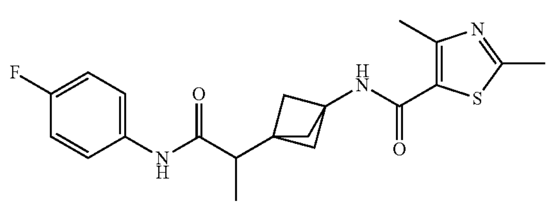 [SMILES: Cc1nc(C)c(C(=O)NC23CC(C(C)C(=O)Nc4ccc(F)cc4)(C2)C3)s1] | N-[3-[2-(4-fluoroanilino)-1-methyl-2-oxo-ethyl]-1-bicyclo[1.1.1]pentanyl]-2,4-dimethyl-thiazole-5-carboxamide | 388 |

TABLE 11-continued

| Ex. # | Structure | Chemical Name | Mass [M + H]+ |
|---|---|---|---|
| 137 | 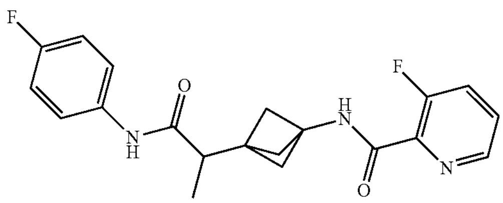 [SMILES: CC(C(=O)Nc1ccc(F)cc1)C12CC(NC(=O)c3ncccc3F)(C1)C2] | 3-fluoro-N-[3-[2-(4-fluoroanilino)-1-methyl-2-oxo-ethyl]-1-bicyclo[1.1.1]pentanyl]pyridin-1-ium-2-carboxamide | 372 |
| 138 | 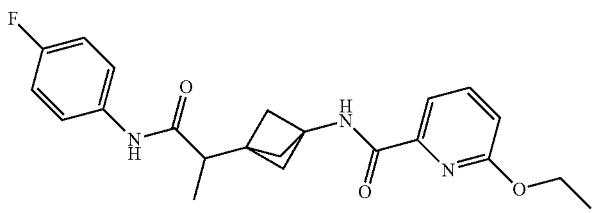 [SMILES: CCOc1cccc(C(=O)NC23CC(C(C)C(=O)Nc4ccc(F)cc4)(C2)C3)n1] | 6-ethoxy-N-[3-[2-(4-fluoroanilino)-1-methyl-2-oxo-ethyl]-1-bicyclo[1.1.1]pentanyl]pyridin-1-ium-2-carboxamide | 398 |
| 139 | 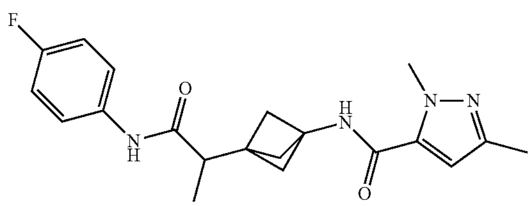 [SMILES: Cc1cc(C(=O)NC23CC(C(C)C(=O)Nc4ccc(F)cc4)(C2)C3)n(C)n1] | N-[3-[2-(4-fluoroanilino)-1-methyl-2-oxo-ethyl]-1-bicyclo[1.1.1]pentanyl]-2,5-dimethyl-pyrazole-3-carboxamide | 371 |
| 140 | 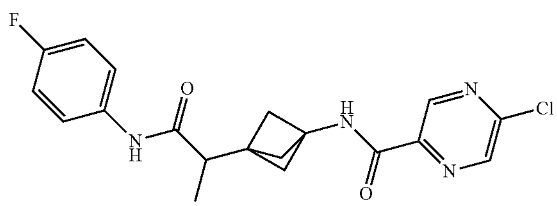 [SMILES: CC(C(=O)Nc1ccc(F)cc1)C12CC(NC(=O)c3cnc(Cl)cn3)(C1)C2] | 5-chloro-N-[3-[2-(4-fluoroanilino)-1-methyl-2-oxo-ethyl]-1-bicyclo[1.1.1]pentanyl]pyrazine-2-carboxamide | 389 |
| 141 | 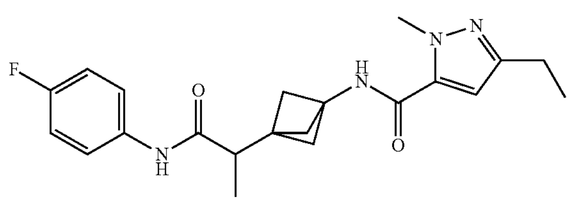 [SMILES: CCc1cc(C(=O)NC23CC(C(C)C(=O)Nc4ccc(F)cc4)(C2)C3)n(C)n1] | 5-ethyl-N-[3-[2-(4-fluoroanilino)-1-methyl-2-oxo-ethyl]-1-bicyclo[1.1.1]pentanyl]-2-methyl-pyrazole-3-carboxamide | 385 |
| 142 | 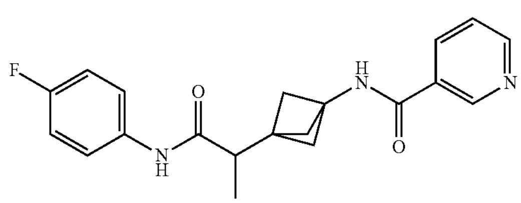 [SMILES: CC(C(=O)Nc1ccc(F)cc1)C12CC(NC(=O)c3cccnc3)(C1)C2] | N-[3-[2-(4-fluoroanilino)-1-methyl-2-oxo-ethyl]-1-bicyclo[1.1.1]pentanyl]pyridin-1-ium-3-carboxamide | 354 |
| 143 | 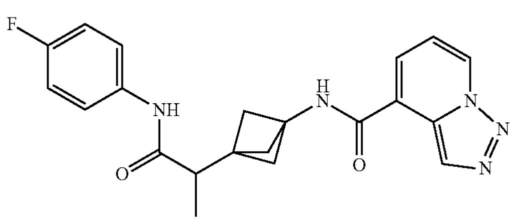 [SMILES: CC(C(=O)Nc1ccc(F)cc1)C12CC(NC(=O)c3cccn4nncc34)(C1)C2] | N-[3-[2-(4-fluoroanilino)-1-methyl-2-oxo-ethyl]-1-bicyclo[1.1.1]pentanyl]triazolo[1,5-a]pyridin-1-ium-4-carboxamide | 394 |

TABLE 11-continued

| Ex. # | Structure | Chemical Name | Mass [M + H]+ |
|---|---|---|---|
| 144 | 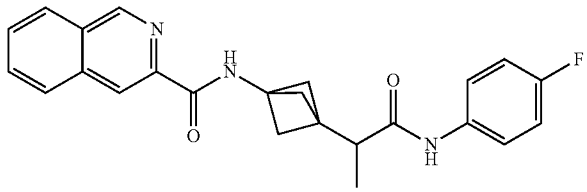 [SMILES: CC(C(=O)Nc1ccc(F)cc1)C12CC(NC(=O)c3cc4ccccc4cn3)(C1)C2] | N-[3-[2-(4-fluoroanilino)-1-methyl-2-oxo-ethyl]-1-bicyclo[1.1.1]pentanyl]isoquinolin-2-ium-3-carboxamide | 404 |

Compounds in Table 12 were prepared in a similar way as described for Example 16-2 from the chiral precursor (S)-2-(3-aminobicyclo[1.1.1]pentan-1-yl)-N-(4-fluorophenyl) propanamide hydrochloride, which was prepared as described in Example 32. The carboxylic acid monomers used were commercially available.

TABLE 12

| Ex. # | Structure | Chemical Name | Mass [M + H]+ |
|---|---|---|---|
| 145 | 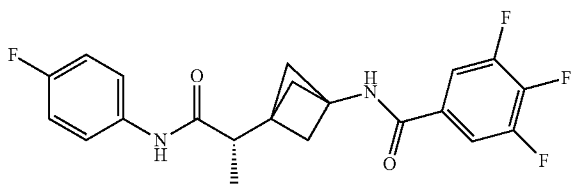 [SMILES: C[C@H](C(=O)Nc1ccc(F)cc1)C12CC(NC(=O)c3cc(F)c(F)c(F)c3)(C1)C2] | (S)-3,4,5-trifluoro-N-(3-(1-((4-fluorophenyl)amino)-1-oxopropan-2-yl)bicyclo[1.1.1]pentan-1-yl)benzamide | 407.02 |
| 146 | 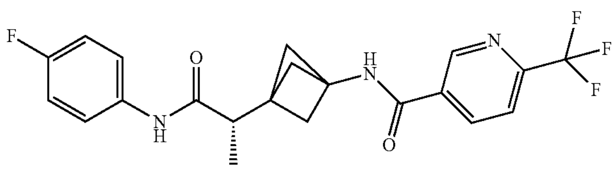 [SMILES: C[C@H](C(=O)Nc1ccc(F)cc1)C12CC(NC(=O)c3ccc(C(F)(F)F)nc3)(C1)C2] | (S)-N-(3-(1-((4-fluorophenyl)amino)-1-oxopropan-2-yl)bicyclo[1.1.1]pentan-1-yl)-6-(trifluoromethyl)nicotinamide | 422.08 |
| 147 | 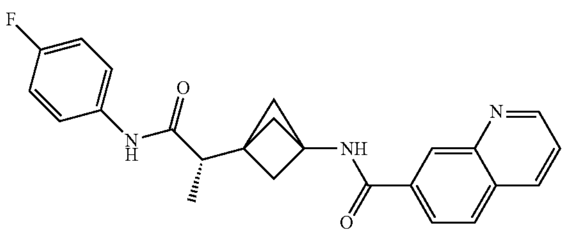 [SMILES: C[C@H](C(=O)Nc1ccc(F)cc1)C12CC(NC(=O)c3ccc4cccnc4c3)(C1)C2] | (S)-N-(3-(1-((4-fluorophenyl)amino)-1-oxopropan-2-yl)bicyclo[1.1.1]pentan-1-yl)quinoline-7-carboxamide | 404.13 |
| 148 | 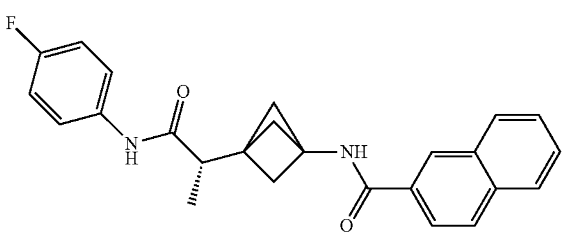 | (S)-N-(3-(1-((4-fluorophenyl)amino)-1-oxopropan-2-yl)bicyclo[1.1.1]pentan-1-yl)-2-naphthamide | 403.12 |
| 149 | 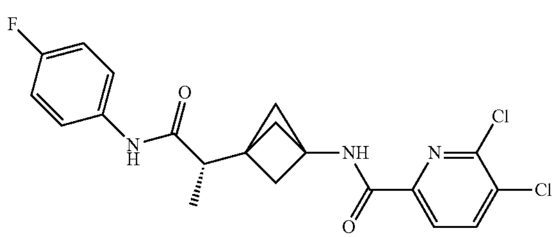 [SMILES: C[C@H](C(=O)Nc1ccc(F)cc1)C12CC(NC(=O)c3ccc(Cl)c(Cl)n3)(C1)C2] | (S)-5,6-dichloro-N-(3-(1-((4-fluorophenyl)amino)-1-oxopropan-2-yl)bicyclo[1.1.1]pentan-1-yl)picolinamide | 421.95 |

TABLE 12-continued

| Ex. # | Structure | Chemical Name | Mass [M + H]+ |
|---|---|---|---|
| 150 | 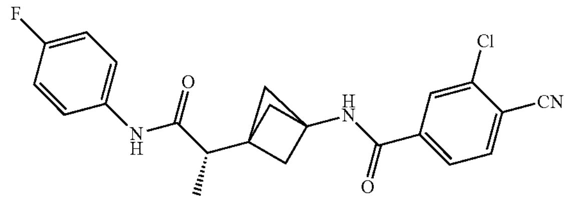 [SMILES: C[C@H](C(=O)Nc1ccc(F)cc1)C12CC(NC(=O)c3ccc(C#N)c(Cl)c3)(C1)C2] | (S)-3-chloro-4-cyano-N-(3-(1-((4-fluorophenyl)amino)-1-oxopropan-2-yl)bicyclo[1.1.1]pentan-1-yl)benzamide | 412.11 |
| 151 | 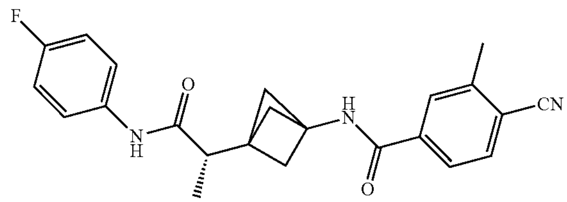 [SMILES: Cc1cc(C(=O)NC23CC([C@H](C)C(=O)Nc4ccc(F)cc4)(C2)C3)ccc1C#N] | (S)-4-cyano-N-(3-(1-((4-fluorophenyl)amino)-1-oxopropan-2-yl)bicyclo[1.1.1]pentan-1-yl)-3-methylbenzamide | 392.11 |
| 152 | 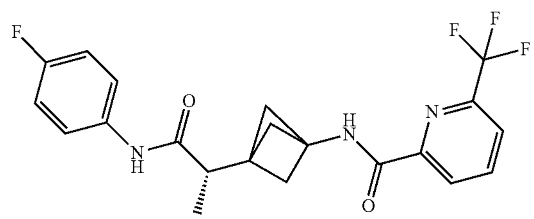 [SMILES: C[C@H](C(=O)Nc1ccc(F)cc1)C12CC(NC(=O)c3cccc(C(F)(F)F)n3)(C1)C2] | (S)-N-(3-(1-((4-fluorophenyl)amino)-1-oxopropan-2-yl)bicyclo[1.1.1]pentan-1-yl)-6-(trifluoromethyl)picolinamide | 422.06 |
| 153 | 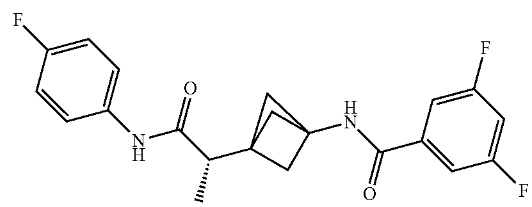 [SMILES: C[C@H](C(=O)Nc1ccc(F)cc1)C12CC(NC(=O)c3cc(F)cc(F)c3)(C1)C2] | (S)-3,5-difluoro-N-(3-(1-((4-fluorophenyl)amino)-1-oxopropan-2-yl)bicyclo[1.1.1]pentan-1-yl)benzamide | 389 |
| 154 | 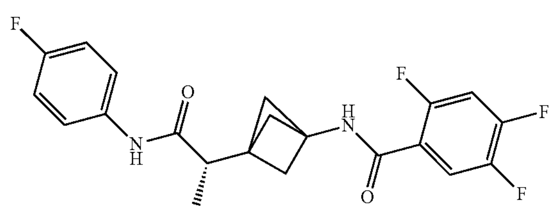 [SMILES: C[C@H](C(=O)Nc1ccc(F)cc1)C12CC(NC(=O)c3cc(F)c(F)cc3F)(C1)C2] | (S)-2,4,5-trifluoro-N-(3-(1-((4-fluorophenyl)amino)-1-oxopropan-2-yl)bicyclo[1.1.1]pentan-1-yl)benzamide | 407 |

Biological Assays

IDO1 Cellular Assay in Hela Cells Stimulated with IFNγ

Hela cells were cultured in complete Hela culture medium (9000 EMEM, 10% heat-inactivated fetal bovine serum) and expanded to about 1×109 cells. The cells were then collected and frozen down at 10×106 cells/vial in 1 mL frozen medium (90% complete Hela culture medium, 10% DMSO).

Compounds to be tested were serially diluted in ten 3-fold steps in DMSO starting from 10 mM DMSO stocks in Echo low volume plate(s). Compound dilutions or DMSO alone were then dispensed from the dilution plate(s) into Greiner black 384-well assay plate(s) (catalog #781086, 50 nL/well) using an Echo 550 acoustic liquid handler (Labcyte).

Frozen Hela cells were thawed and transferred into Hela assay medium (99% complete Hela culture medium, 1% Pen/Strep) with 20 mL medium/vial of cells. The cells were spun down at 250 g in a table top centrifuge for 5 min and suspended in same volume of Hela assay medium. The cells were then counted and adjusted to a density of 2×105 cells/ml in Hela assay medium. Sterile L-tryptophan were added to the cells with final concentration of 300 uM L-tryptophan. A small aliquot (2 mL/plate) of Hela cells were set aside and were not treated with IFNγ, to serve as the Max-E control. The rest of Hela cells were added with sterile IFNγ (Cat #285-IF, R & D systems) with a final concentration of 100 ng/mL.

Hela cells with and without IFNγ were dispensed to the respective wells of 384-well assay plates containing the compounds. The plates were incubated for about 48 hours at a 37° C., 5% CO₂ incubator. Afterwards, 12 μL of 0.5 M methyl isonipecotate in dimethyl sulfoxide were added into each well and the plates were sealed and incubated at 37° C. without CO₂ overnight. The plates were centrifuged for 1 min at 200×g. The resulting fluorescence was measured in a Spectramax plate reader (Molecular Devices) with a 400 nm excitation filter and a 510 nm emission filter.

The fluorescence intensity of each well was corrected for the background observed in wells with non-IFNγ-treated cells and was expressed as a fraction of the intensity observed in wells of IFNγ-treated cells and DMSO only. Potencies were calculated by linear least squares fit to the four parameter logistic $IC_{50}$ equation.

The biological activity data using the IDO1 enzyme assay and IDO1 cellular assay described above are summarized in the table below. Compounds disclosed herein generally have $IC_{50}$ of about 0.1 nM to about 20,000 nM, or more specifically, about 1 nM to about 10,000 nM, or more specifically, about 5 nM to about 5,000 nM, or more specifically, about 10 nM to about 1,000 nM, or still more specifically, about 10 nM to about 500 nM. Such a result is indicative of the intrinsic activity of the compounds in use as an inhibitor of an IDO enzyme. Specific $IC_{50}$ activity data for the exemplified compounds disclosed herein is provided in the following table.

| Ex. No. | IDO1 HELA Cell Assay, $IC_{50}$, nM |
| --- | --- |
| 1 | 3.054 |
| 2 | 230 |
| 3 | 6.295 |
| 4 | 47.85 |
| 5 | 2.123 |
| 6 | 38.56 |
| 7 | 1.049 |
| 8 | 3.1 |
| 9 | 1.546 |
| 10 | 36.4 |
| 11 | 1.574 |
| 12 | 97.94 |
| 13 | 132.8 |
| 14 | 6.16 |
| 15 | 4.456 |
| 16 | 182.6 |
| 17 | 5.257 |
| 18 | 2.907 |
| 19 | 563.8 |
| 20 | 29.17 |
| 21 | 908.4 |
| 22 | 28.74 |
| 23 | 107 |
| 24 | 4.126 |
| 25 | 83.23 |
| 26 | 377 |
| 27 | 104.2 |
| 28 | 72.16 |
| 29 | 275.7 |
| 30 | 47.72 |
| 31 | >10000 |
| 32 | 114.7 |
| 33 | 7183 |
| 34 | 26.95 |
| 35 | 121.9 |
| 36 | 2.137 |
| 37 | 134.8 |
| 38 | 2.002 |
| 39 | 200.9 |
| 40 | 2.351 |
| 41 | 404.6 |
| 42 | 5.022 |
| 43 | 153 |
| 44 | 2.282 |
| 45 | 109.3 |
| 46 | 2.121 |
| 47 | 152.4 |
| 48 | 1.715 |
| 49 | 249.6 |
| 50 | 3.288 |
| 51 | 226 |
| 52 | 2.495 |
| 53 | 123.2 |
| 54 | 187.5 |
| 55 | 151.8 |
| 56 | 2.507 |
| 57 | 15.74 |
| 58 | 16.62 |
| 59 | 6.524 |
| 60 | 157 |
| 61 | 10.99 |
| 62 | 30.94 |
| 63 | 11.38 |
| 64 | 11.39 |
| 65 | 28.07 |
| 66 | 13.11 |
| 67 | 98.01 |
| 68 | 13.85 |
| 69 | 23.61 |
| 70 | 19.71 |
| 71 | 26.91 |
| 72 | 34.78 |
| 73 | 48.35 |
| 74 | 55.65 |
| 75 | 175.8 |
| 76 | 217.5 |
| 77 | 6.266 |
| 78 | 21.78 |
| 79 | 20.37 |
| 80 | 58.55 |
| 81 | 15.44 |
| 82 | 30.26 |
| 83 | 39.03 |
| 84 | 77.24 |
| 85 | 73.18 |
| 86 | 84.83 |
| 87 | 90.32 |
| 88 | 315.1 |
| 89 | 65.37 |
| 90 | 117.9 |
| 91 | 121.9 |
| 92 | 6.433 |
| 93 | 104.8 |
| 94 | 7.78 |
| 95 | 60.57 |
| 96 | 78.44 |
| 97 | 259.9 |
| 98 | 23.17 |
| 99 | 111.5 |
| 100 | 3.348 |
| 101 | 16.86 |
| 102 | 19.22 |
| 103 | 46.93 |
| 104 | 20.68 |
| 105 | 35.85 |
| 106 | |
| 107 | |
| 108 | |
| 109 | 11.2 |
| 110 | 17.67 |
| 111 | 34.2 |
| 112 | 40.36 |
| 113 | 47.33 |
| 114 | 59.61 |
| 115 | 66.96 |
| 116 | 69.18 |
| 117 | 73.5 |
| 118 | 89.4 |
| 119 | 112.6 |
| 120 | 125.1 |
| 121 | 130.9 |
| 122 | 132.2 |
| 123 | 147 |
| 124 | 152.9 |
| 125 | 178.4 |
| 126 | 180.1 |
| 127 | 185.9 |
| 128 | 194.5 |
| 129 | 231.5 |
| 130 | 247.4 |
| 131 | 247.9 |
| 132 | 252.1 |
| 133 | 259.1 |
| 134 | 266.8 |
| 135 | 275.8 |

-continued

| Ex. No. | IDO1 HELA Cell Assay, IC$_{50}$, nM |
|---|---|
| 136 | 318.3 |
| 137 | 386.8 |
| 138 | 387.9 |
| 139 | 396 |
| 140 | 399 |
| 141 | 415.3 |
| 142 | 418.3 |
| 143 | 448.3 |
| 144 | 463.1 |
| 145 | 3.038 |
| 146 | 217.5 |
| 147 | 175.8 |
| 148 | 19.71 |
| 149 | 26.91 |
| 150 | 48.35 |
| 151 | 55.65 |
| 152 | 34.78 |
| 153 | |
| 154 | |

IDO1 Human whole blood Assay

Compounds to be tested were serially diluted in ten 3-fold steps in DMSO starting from 10 mM. 3 µL of compound dilutions or DMSO alone were then dispensed from the dilution plate into a polypropylene 96-well assay plate containing 97 µL of RPMI using an Echo 555 acoustic liquid handler (Labcyte). LPS and IFNγ was prepared in RPMI to a 10× of final conc. (1000 ng/mL), final concentration is 100 ng/mL.

Human whole blood was drawn in sodium heparin coated tubes from healthy internal donors. Two hundred forty µL of blood was transferred to each of the wells of a v-bottom 96 well plate. Thirty µL of compound was transferred from intermediate dilution plate, and incubated for 15 min. Thirty µL from stimulants was then transferred to blood and mixed thoroughly. Plate was covered with breathable membrane and incubated at 37° C. for overnight (18 h).

On day 2 isotope labeled standard of kynurenine and tryptophan was made in water at 10× concentration and 30 µL was added to the blood at 3 µM final concentration. The assay plates were centrifuged at 300×G for 10 min with no brake to separate plasma from red blood cells. Sixty µL of plasma samples was removed without disturbing red blood cells. Plasma was diluted with RPMI in 1:1 ratio and proteins were precipitated out with two volume of acetonitrile. The plates were centrifuged at 4000×G for 60 min. Twenty µL of supernatant was carefully transferred to a 384 well plate containing 40 µL of 0.1% formic acid in water and analyzed by LC/MS/MS.

LC/MS/MS analyses were performed using Thermo Fisher's LX4-TSQ Quantum Ultra system. This system consists of four Agilent binary high-performance liquid chromatography (HPLC) pumps and a TSQ Quantum Ultra triple quadruple MS/MS instrument. For each sample, 5 µL were injected onto an Atlantis T3 column (2.1 mm×150 mm, 3 µm particle size) from Waters. The mobile phase gradient pumped at 0.8 mL/min was used to elute the analytes from the column at 25° C. The elution started at 0% B increasing linearly to 25% B at 6.5 min, holding at 25% for 1 min, re-equilibrating to 10 min. Mobile phase A consisted of 0.1% formic acid in water. Mobile phase B consisted of 0.1% of formic acid in acetonitrile. Data was acquired in positive mode using a HESI interface. The operational parameters for the TSQ Quantum Ultra instrument were a spray voltage of 4000 V, capillary temperature of 380° C., vaporizer temperature 400° C., sheath gas 60 arbitrary units, Aux gas 20 arbitrary units, tube lens 85 and collision gas 1.2 mTorr. SRM chromatograms of kynurenine (Q1: 209.2>Q3:94.0) and internal standard (Q1: 215.3>Q3:98.2) were collected for 90 sec. The peak area was integrated by Xcalibur Quan software. The ratios between the kynurenine generated in the reaction and 2D6-Kynurenine spiked-in internal standard were used to generate percentage inhibition and IC$_{50}$ values. Compounds were titrated and IC$_{50}$'s were calculated by 4 parameter sigmoidal curve fitting formula.

The biological activity data of selective compounds using the IDO1 human whole blood assay described above are summarized in the table below.

| Ex. No. | IDO1 human whole blood assay, IC$_{50}$, nM |
|---|---|
| 1 | 113 |
| 5 | 44.74 |
| 7 | 48.23 |
| 8 | 780.7 |
| 9 | 923.8 |
| 11 | 524.7 |
| 14 | 406.1 |
| 15 | 1099 |
| 17 | 178.9 |
| 24 | 400.9 |
| 36 | 138.2 |
| 46 | 139.2 |
| 52 | 53.26 |
| 56 | 328 |
| 77 | 452.4 |
| 100 | 453.8 |
| 145 | 49.04 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of formula (I), or a pharmaceutically acceptable salt thereof:

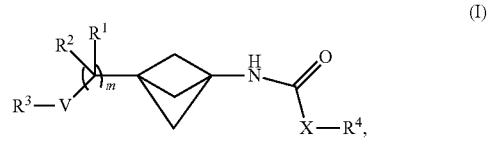

wherein:

m is 1;

V is selected from

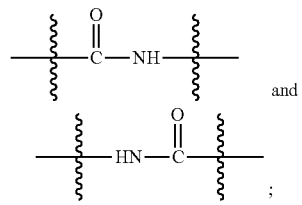

and

X is selected from a bond, O and N(R$^a$); where R$^a$ is selected from hydrogen and C$_{1-6}$ alkyl;

each occurrence of $R^1$ and $R^2$ is independently selected from:
(i) hydrogen,
(ii) $C_{1-6}$ alkyl, and
(iii) $C_{3-6}$ cycloalkyl;
or alternatively, le and $R^2$ together with the carbon to which they are attached form a $C_{3-6}$ cycloalkyl or a 4-6 membered heterocyclyl; wherein the $C_{3-6}$ cycloalkyl is optionally substituted with $C_{1-6}$ alkyl; and
each occurrence of $R^3$ and $R^4$ is independently selected from:
(i) $C_{1-6}$ alkyl, optionally substituted with one to four substituents independently selected from halogen and phenyl,
(ii) $C_{3-6}$ cycloalkyl,
(iii) aryl, and
(iv) heterocyclyl;
wherein each of the phenyl of (i), aryl of (iii) and heterocyclyl of (iv) is optionally substituted with one to four substituents independently selected from:
(a) halogen,
(b) $C_{1-6}$ alkyl, optionally substituted with one to four halogens,
(c) —O—$C_{1-6}$ alkyl, optionally substituted with one to four halogens,
(d) $C_{3-6}$ cycloalkyl, optionally substituted with one to four halogens, and
(e) —CN.

2. The compound of claim 1, or a pharmaceutically acceptable salt thereof, wherein:
each occurrence of $R^1$ and $R^2$ is independently selected from:
(i) hydrogen,
(ii) $C_{1-6}$ alkyl, and
(iii) $C_{3-6}$ cycloalkyl;
or alternatively, $R^1$ and $R^2$ together with the carbon to which they are attached form a $C_{3-6}$ cycloalkyl or a 4-6 membered saturated heterocyclyl; wherein the $C_{3-6}$ cycloalkyl is optionally substituted with $C_{1-6}$ alkyl.

3. The compound of claim 1, or a pharmaceutically acceptable salt thereof, wherein:
$R^1$ is hydrogen; and
$R^2$ is methyl;
or alternatively, $R^1$ and $R^2$ together with the carbon to which they are attached form a $C_{3-6}$ cycloalkyl or oxetanyl; wherein the $C_{3-6}$ cycloalkyl is optionally substituted with methyl.

4. The compound of claim 1, or a pharmaceutically acceptable salt thereof, wherein $R^3$ is selected from:
(i) phenyl,
(ii) naphthyl and
(iii) pyridinyl;
wherein each of the phenyl of (i), naphthyl of (ii) and pyridinyl of (iii) is optionally substituted with one to four substituents independently selected from:
(a) halogen, and
(b) $C_{1-6}$ alkyl, optionally substituted with one to three halogens.

5. The compound of claim 4, or a pharmaceutically acceptable salt thereof, wherein $R^3$ is selected from:
(i) phenyl, and
(ii) pyridinyl;
wherein each of the phenyl of (i) and pyridinyl of (ii) is optionally substituted with a halogen.

6. The compound of claim 1, or a pharmaceutically acceptable salt thereof, wherein $R^4$ is selected from:
(i) phenyl,
(ii) naphthyl and
(iii) a heterocyclyl selected from furanyl, imidazolyl, isothiazolyl, isoxazolyl, oxadiazolyl, oxazolyl, pyranyl, pyrazinyl, pyrazolyl, pyridazinyl, pyridinyl, pyrimidinyl, pyrrolyl, tetrahydropyrazinyl, tetrahydropyridazinyl, tetrahydropyridinyl, tetrahydropyrimidinyl, tetrazolyl, thiadiazolyl, thiazolyl, thienyl, thiophenyl, triazolyl, imidazo[1,5-a]pyridinyl, indolinyl, indolizinyl, isoquinolinyl, pyrazolo[1,5-a]pyridinyl, quinolinyl, 4,5,6,7-tetrahydro-1,2-benzoxazolyl and triazolo[1,5-a]pyridinyl;
wherein each of the phenyl of (i), naphthyl of (ii) and heterocyclyl of (iii) is optionally substituted with one to four substituents independently selected from:
(a) halogen,
(b) $C_{1-6}$ alkyl, optionally substituted with one to four halogens,
(c) —O—$C_{1-6}$ alkyl, optionally substituted with one to four halogens,
(d) $C_{3-6}$ cycloalkyl, optionally substituted with one to four halogens, and
(e) —CN.

7. The compound of claim 6, or a pharmaceutically acceptable salt thereof, wherein $R^4$ is selected from:
(i) phenyl, and
(ii) a heterocyclyl selected from isoxazolyl, oxadiazolyl, pyrazinyl, pyrazolyl, pyridinyl, pyrimidinyl, thiazolyl, imidazo[1,5-a]pyridinyl, indolinyl, indolizinyl, isoquinolinyl, pyrazolo[1,5-a]pyridinyl, quinolinyl, 4,5,6,7-tetrahydro-1,2-benzoxazolyl and triazolo[1,5-a]pyridinyl;
wherein each of the phenyl of (i) and heterocyclyl of (ii) is optionally substituted with one to three substituents independently selected from:
(a) halogen,
(b) $C_{1-4}$ alkyl, optionally substituted with one to four halogens,
(c) —O—$C_{1-4}$ alkyl, optionally substituted with one to four halogens, and
(d) CN.

8. The compound of claim 1, or a pharmaceutically acceptable salt thereof, wherein:
each occurrence of $R^1$ and $R^2$ is independently selected from:
(i) hydrogen,
(ii) $C_{1-6}$ alkyl, and
(iii) $C_{3-6}$ cycloalkyl;
or alternatively, $R^1$ and $R^2$ together with the carbon to which they are attached form a $C_{3-6}$ cycloalkyl;
$R^3$ is selected from:
(i) phenyl,
(ii) naphthyl and
(iii) pyridinyl;
wherein each of the phenyl of (i), naphthyl of (ii) and pyridinyl of (iii) is optionally substituted with one to four substituents independently selected from:
(a) halogen, and
(b) $C_{1-6}$ alkyl; and
$R^4$ is selected from:
(i) phenyl,
(ii) naphthyl and
(iii) a heterocyclyl selected from isoxazolyl, oxadiazolyl, pyrazinyl, pyrazolyl, pyridinyl, pyrimidinyl, thiazolyl, imidazo[1,5-a]pyridinyl, indolinyl, indolizinyl, isoquinolinyl, pyrazolo[1,5-a]pyridinyl, quinolinyl, 4,5,6,7-tetrahydro-1,2-benzoxazolyl and triazolo[1,5-a]pyridinyl;

wherein each of the phenyl of (i), naphthyl of (ii) and heterocyclyl of (iii) is optionally substituted with one to four substituents independently selected from:
(a) halogen,
(b) $C_{1-6}$ alkyl, optionally substituted with one to four halogens,
(c) —O—$C_{1-6}$ alkyl, optionally substituted with one to four halogens, and
(d) CN.

9. The compound of claim 1, or a pharmaceutically acceptable salt thereof, wherein:
$R^1$ is hydrogen;
$R^2$ is selected from:
(i) hydrogen, and
(ii) $C_{1-6}$ alkyl;
or alternatively, le and $R^2$ together with the carbon to which they are attached form a $C_{3-6}$cycloalkyl;
$R^3$ is selected from:
(i) phenyl, and
(ii) pyridinyl;
wherein each of the phenyl of (i) and pyridinyl of (ii) is optionally substituted with a halogen; and
$R^4$ is selected from:
(i) phenyl,
(ii) naphthyl and
(iii) a heterocyclyl selected from isoxazolyl, oxadiazolyl, pyrazinyl, pyrazolyl, pyridinyl, pyrimidinyl, thiazolyl, imidazo[1,5-a]pyridinyl, indolinyl, indolizinyl, isoquinolinyl, pyrazolo[1,5-a]pyridinyl, quinolinyl, 4,5,6,7-tetrahydro-1,2-benzoxazolyl and triazolo[1,5-a]pyridinyl;
wherein each of the phenyl of (i), naphthyl of (ii) and heterocyclyl of (iii) is optionally substituted with one to four substituents independently selected from:
(a) halogen,
(b) $C_{1-4}$ alkyl, optionally substituted with one to four halogens,
(c) —O—$C_{1-4}$ alkyl, optionally substituted with one to four halogens, and
(d) CN.

10. The compound of claim 1 of formula (Ib), or a pharmaceutically acceptable salt thereof:

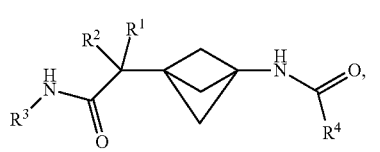

(Ib)

wherein:
$R^1$ is hydrogen;
$R^2$ is selected from:
(i) hydrogen, and
(ii) $C_{1-6}$ alkyl;
or alternatively, le and $R^2$ together with the carbon to which they are attached form a $C_{3-6}$ cycloalkyl or a 4-6 membered saturated heterocyclyl;
$R^3$ is selected from:
(i) phenyl, and
(ii) pyridinyl;
wherein each of the phenyl of (i) and pyridinyl of (ii) is optionally substituted with a halogen; and $R^4$ is selected from:
(i) phenyl,
(ii) naphthyl and
(iii) a heterocyclyl selected from isoxazolyl, oxadiazolyl, pyrazinyl, pyrazolyl, pyridinyl, pyrimidinyl, thiazolyl, imidazo[1,5-a]pyridinyl, indolinyl, indolizinyl, isoquinolinyl, pyrazolo[1,5-a]pyridinyl, quinolinyl, 4,5,6,7-tetrahydro-1,2-benzoxazolyl and triazolo[1,5-a]pyridinyl;
wherein each of the phenyl of (i), naphthyl of (ii) and heterocyclyl of (iii) is optionally substituted with one to four substituents independently selected from:
(a) halogen,
(b) $C_{1-4}$ alkyl, optionally substituted with one to four halogens,
(c) —O—$C_{1-4}$ alkyl, optionally substituted with one to four halogens, and
(d) CN.

11. The compound of claim 1 of formula (Id), or a pharmaceutically acceptable salt thereof:

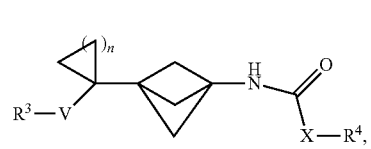

(Id)

wherein:
n is 1, 2 or 3;
V is selected from

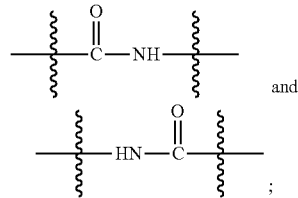

and
;

X is selected from a bond, O and N($R^a$); wherein $R^a$ is selected from hydrogen and methyl;
$R^3$ is selected from:
(i) phenyl, and
(ii) pyridinyl;
wherein each of the phenyl of (i) and pyridinyl of (ii) is optionally substituted with a halogen; and
$R^4$ is selected from:
(i) phenyl,
(ii) naphthyl and
(iii) a heterocyclyl selected from isoxazolyl, oxadiazolyl, pyrazinyl, pyrazolyl, pyridinyl, pyrimidinyl, thiazolyl, imidazo[1,5-a]pyridinyl, indolinyl, indolizinyl, isoquinolinyl, pyrazolo[1,5-a]pyridinyl, quinolinyl, 4,5,6,7-tetrahydro-1,2-benzoxazolyl and triazolo[1,5-a]pyridinyl;
wherein each of the phenyl of (i), naphthyl of (ii) and heterocyclyl of (iii) is optionally substituted with one to four substituents independently selected from:
(a) halogen,
(b) $C_{1-4}$ alkyl, optionally substituted with one to four halogens,
(c) —O—$C_{1-4}$ alkyl, optionally substituted with one to four halogens, and
(d) CN.

12. The compound of claim 1 of formula (If), or a pharmaceutically acceptable salt thereof:

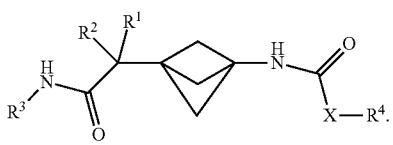

wherein:
R¹ is hydrogen;
R² is selected from:
  (i) hydrogen, and
  (ii) $C_{1-6}$ alkyl;
or alternatively, le and R² together with the carbon to which they are attached form a $C_{3-6}$ cycloalkyl;
R³ is selected from:
  (i) phenyl, and
  (ii) pyridinyl;
wherein each of the phenyl of (i) and pyridinyl of (ii) is optionally substituted with a halogen; and
R⁴ is selected from:
  (i) $C_{1-6}$ alkyl, optionally substituted with an aryl; and
  (ii) $C_{3-6}$ cycloalkyl.

13. The compound of claim 1 of formula (Ih), or a pharmaceutically acceptable salt thereof:

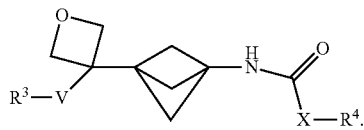

wherein:
V is selected from

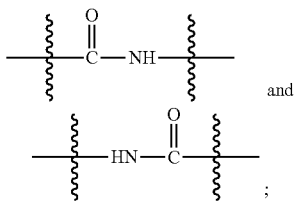

X is selected from a bond, O and N(Rᵃ); wherein Rᵃ is selected from hydrogen and methyl;
R³ is selected from:
  (i) phenyl, and
  (ii) pyridinyl;
wherein each of the phenyl of (i) and pyridinyl of (ii) is optionally substituted with a halogen; and
R⁴ is selected from:
  (i) phenyl,
  (ii) naphthyl and
  (iii) a heterocyclyl selected from isoxazolyl, oxadiazolyl, pyrazinyl, pyrazolyl, pyridinyl, pyrimidinyl, thiazolyl, imidazo[1,5-a]pyridinyl, indolinyl, indolizinyl, isoquinolinyl, pyrazolo[1,5-a]pyridinyl, quinolinyl, 4,5,6,7-tetrahydro-1,2-benzoxazolyl and triazolo[1,5-a]pyridinyl;

wherein each of the phenyl of (i), naphthyl of (ii) and heterocyclyl of (iii) is optionally substituted with one to four substituents independently selected from:
  (a) halogen,
  (b) $C_{1-4}$ alkyl, optionally substituted with one to four halogens,
  (c) —O—$C_{1-4}$ alkyl, optionally substituted with one to four halogens, and
  (d) CN.

14. A compound selected from:
3-chloro-N-(3-(1-((4-fluorophenyl)amino)-1-oxopropan-2-yl)bicyclo[1.1.1]pentan-1-yl)benzamide,
3-chloro-N-(3-(1-((4-fluorophenyl) carbamoyl) cyclobutyl) bicyclo [1.1.1] pentan-1-yl) benzamide,
3-cyano-N-(3-(1-((4-fluorophenyl)carbamoyl)cyclobutyl)bicyclo[1.1.1]pentan-1-yl)benzamide,
3,4-dichloro-N-(3-(1-((4-fluorophenyl)carbamoyl)cyclobutyl)bicyclo[1.1.1]pentan-1-yl)benzamide,
3-chloro-N-(3-(1-((4-chlorophenyl)amino)-1-oxopropan-2-yl)bicyclo [1.1.1] pentan-1-yl) benzamide,
3,4-dichloro-N-(3-(1-((4-fluorophenyl)amino)-1-oxopropan-2-yl)bicyclo[1.1.1]pentan-1-yl)benzamide,
3-chloro-N-(3-(1-((4-chloro-3-fluorophenyl)amino)-1-oxopropan-2-yl)bicyclo[1.1.1]pentan-1-yl)benzamide,
N-(3-(1-((4-chlorophenyl)amino)-1-oxopropan-2-yl)bicyclo[1.1.1]pentan-1-yl)-3-cyanobenzamide,
3,4-dichloro-N-(3-(1-((6-fluoropyridin-3-yl)amino)-1-oxopropan-2-yl)bicyclo[1.1.1]pentan-1-yl)benzamide,
3-chloro-N-(3-(1-((6-chloropyridin-3-yl)amino)-1-oxopropan-2-yl)bicyclo[1.1.1]pentan-1-yl)benzamide,
N-(3-(1-((6-chloropyridin-3-yl)amino)-1-oxopropan-2-yl)bicyclo[1.1.1]pentan-1-yl)bicyclo[4.2.0]octa-1(6),2,4-triene-3-carboxamide,
cyclopropyl (3-(1-((4-chlorophenyl)amino)-1-oxopropan-2-yl)bicyclo [1.1.1] pentan-1-yl) carbamate,
3, 4-dichloro-N-(3-(1-(4-fluorobenzamido)ethyl) bicyclo [1.1.1] pentan-1-yl) benzamide, benzyl (3-(1-(4-fluorobenzamido)cyclopropyl)bicyclo[1.1.1]pentan-1-yl) carbamate,
3,4-dichloro-N-(3-(1-(4-fluorobenzamido)cyclopropyl) bicyclo[1.1.1]pentan-1-yl)benzamide,
5-chloro-N-(3-(1-(4-fluorobenzamido)cyclopropyl)bicyclo[1.1.1]pentan-1-yl)pi colinamide,
N-(3-(1-(4-fluorobenzamido)cyclopropyl)bicyclo[1.1.1] pentan-1-yl)-5-(trifluoromethyl)picolinamide,
4-(difluoromethyl)-N-(3-(1-(4-fluorobenzamido)cyclopropyl)bicyclo[1.1.1]pen tan-1-yl)picolinamide,
N-(3-(1-(4-fluorobenzamido)cyclopropyl)bicyclo[1.1.1] pentan-1-yl)-3-methyl-1,2,4-oxadiazole-5-carboxamide,
3-cyclopropyl-N-(3-(1-(4-fluorobenzamido)cyclopropyl) bicyclo[1.1.1]pentan-1-yl)-1,2,4-oxadiazole-5-carboxamide,
N-(3-(1-(4-fluorobenzamido)cyclopropyl)bicyclo[1.1.1] pentan-1-yl)-5-methyl-1,2,4-oxadiazole-3-carboxamide,
tert-butyl (R)-(3-(1-((4-fluorophenyl)amino)-1-oxopropan-2-yl)bicyclo[1.1.1]pentan-1-yl)carbamate,
tert-butyl (S)-(3-(1-((4-fluorophenyl)amino)-1-oxopropan-2-yl)bicyclo[1.1.1]pentan-1-yl)carbamate,
(R)-6-chloro-N-(3-(1-((4-fluorophenyl)amino)-1-oxopropan-2-yl)bicyclo[1.1.1]pentan-1-yl)picolinamide,
(S)-6-chloro-N-(3-(1-((4-fluorophenyl)amino)-1-oxopropan-2-yl)bicyclo[1.1.1]pentan-1-yl)picolinamide,
3-chloro-4-fluoro-N-[3-[(1R)-2-(4-fluoroanilino)-1-methyl-2-oxo-ethyl]-1-bicyclo[1.1.1]pentanyl]benzamide, 3-chloro-N-[3-[(1R)-2-(4-fluoroanilino)-1-methyl-2-oxo-ethyl]-1-bicyclo[1.1.1]pentanyl]-4-methyl-benzamide,
4-chloro-N-[3-[(1R)-2-(4-fluoroanilino)-1-methyl-2-oxo-ethyl]-1-bicyclo[1.1.1]pentanyl]-3-methyl-benzamide,
3-chloro-2-fluoro-N-[3-[(1R)-2-(4-fluoroanilino)-1-methyl-2-oxo-ethyl]-1-bicyclo[1.1.1]pentanyl]benzamide,
4-fluoro-N-[3-[(1R)-2-(4-fluoroanilino)-1-methyl-2-oxo-ethyl]-1-bicyclo[1.1.1]pentanyl]-3-methyl-benzamide,
3-chloro-5-fluoro-N-[3-[(1R)-2-(4-fluoroanilino)-1-methyl-2-oxo-ethyl]-1-bicyclo[1.1.1]pentanyl]benzamide,
3-fluoro-N-[3-[(1R)-2-(4-fluoroanilino)-1-methyl-2-oxo-ethyl]-1-bicyclo[1.1.1]pentanyl]-4-methyl-benzamide,
N-[3-[(1R)-2-(4-fluoroanilino)-1-methyl-2-oxo-ethyl]-1-bicyclo[1.1.1]pentanyl]-3-(trifluoromethyl)benzamide,
3,4-difluoro-N-[3-[(1R)-2-(4-fluoroanilino)-1-methyl-2-oxo-ethyl]-1-bicyclo[1.1.1]pentanyl]benzamide,
3-chloro-N-[3-[(1R)-2-(4-fluoroanilino)-1-methyl-2-oxo-ethyl]-1-bicyclo[1.1.1]pentanyl]-4-methyl-benzamide,
4-chloro-N-[3-[(1R)-2-(4-fluoroanilino)-1-methyl-2-oxo-ethyl]-1-bicyclo[1.1.1]pentanyl]-3-methyl-benzamide,
4-fluoro-N-[3-[(1R)-2-(4-fluoroanilino)-1-methyl-2-oxo-ethyl]-1-bicyclo[1.1.1]pentanyl]-3-methyl-benzamide,
4-chloro-3-fluoro-N-[3-[(1S)-2-(4-fluoroanilino)-1-methyl-2-oxo-ethyl]-1-bicyclo[1.1.1]pentanyl]benzamide,
3-chloro-4-fluoro-N-[3-[(1S)-2-(4-fluoroanilino)-1-methyl-2-oxo-ethyl]-1-bicyclo[1.1.1]pentanyl]benzamide,
3-chloro-N-[3-[(1S)-2-(4-fluoroanilino)-1-methyl-2-oxo-ethyl]-1-bicyclo[1.1.1]pentanyl]-4-methyl-benzamide,
4-chloro-N-[3-[(1S)-2-(4-fluoroanilino)-1-methyl-2-oxo-ethyl]-1-bicyclo[1.1.1]pentanyl]-3-methyl-benzamide,
3-chloro-2-fluoro-N-[3-[(1S)-2-(4-fluoroanilino)-1-methyl-2-oxo-ethyl]-1-bicyclo[1.1.1]pentanyl]benzamide,
4-chloro-2-fluoro-N-[3-[(1S)-2-(4-fluoroanilino)-1-methyl-2-oxo-ethyl]-1-bicyclo[1.1.1]pentanyl]benzamide,
3-chloro-N-[3-[(1S)-2-(4-fluoroanilino)-1-methyl-2-oxo-ethyl]-1-bicyclo[1.1.1]pentanyl]-2-methyl-benzamide,
4-fluoro-N-[3-[(1S)-2-(4-fluoroanilino)-1-methyl-2-oxo-ethyl]-1-bicyclo[1.1.1]pentanyl]-3-methyl-benzamide,
3-chloro-5-fluoro-N-[3-[(1S)-2-(4-fluoroanilino)-1-methyl-2-oxo-ethyl]-1-bicyclo[1.1.1]pentanyl]benzamide,
5-chloro-2-fluoro-N-[3-[(1S)-2-(4-fluoroanilino)-1-methyl-2-oxo-ethyl]-1-bicyclo[1.1.1]pentanyl]benzamide,
N-[3-[(1S)-2-(4-fluoroanilino)-1-methyl-2-oxo-ethyl]-1-bicyclo[1.1.1]pentanyl]-4-methyl-pyrimidin-1-ium-2-carboxamide,
3-fluoro-N-[3-[(1S)-2-(4-fluoroanilino)-1-methyl-2-oxo-ethyl]-1-bicyclo[1.1.1]pentanyl]-4-methyl-benzamide,
5-chloro-N-[3-[(1S)-2-(4-fluoroanilino)-1-methyl-2-oxo-ethyl]-1-bicyclo[1.1.1]pentanyl]pyridin-1-ium-3-carboxamide,
6-chloro-N-[3-[(1S)-2-(4-fluoroanilino)-1-methyl-2-oxo-ethyl]-1-bicyclo[1.1.1]pentanyl]pyridin-1-ium-3-carboxamide,
6-chloro-N-[3-[(1S)-2-(4-fluoroanilino)-1-methyl-2-oxo-ethyl]-1-bicyclo[1.1.1]pentanyl]-5-methyl-pyridin-1-ium-2-carboxamide,
N-[3-[(1S)-2-(4-fluoroanilino)-1-methyl-2-oxo-ethyl]-1-bicyclo[1.1.1]pentanyl]-3-(trifluoromethyl)benzamide,
5,6-dichloro-N-[3-[(1S)-2-(4-fluoroanilino)-1-methyl-2-oxo-ethyl]-1-bicyclo[1.1.1]pentanyl]pyridin-1-ium-3-carboxamide,
N-[3-[(1S)-2-(4-fluoroanilino)-1-methyl-2-oxo-ethyl]-1-bicyclo[1.1.1]pentanyl]-5,6-dimethyl-pyridin-1-ium-2-carboxamide,
5-fluoro-N-[3-[(1S)-2-(4-fluoroanilino)-1-methyl-2-oxo-ethyl]-1-bicyclo[1.1.1]pentanyl]-6-methyl-pyridin-1-ium-3-carboxamide,
N-[3-[(1S)-2-(4-fluoroanilino)-1-methyl-2-oxo-ethyl]-1-bicyclo[1.1.1]pentanyl]-2-(trifluoromethyl)pyridin-1-ium-4-carboxamide,
4-fluoro-N-[3-[(1S)-2-(4-fluoroanilino)-1-methyl-2-oxo-ethyl]-1-bicyclo[1.1.1]pentanyl]-3-methoxy-benzamide,
N-[3-[(1S)-2-(4-fluoroanilino)-1-methyl-2-oxo-ethyl]-1-bicyclo[1.1.1]pentanyl]-5-(trifluoromethyl)pyridin-1-ium-3-carboxamide,
3,4-difluoro-N-[3-[(1S)-2-(4-fluoroanilino)-1-methyl-2-oxo-ethyl]-1-bicyclo[1.1.1]pentanyl]benzamide,
(S)—N-(3-(1-((4-fluorophenyl)amino)-1-oxopropan-2-yl)bicyclo[1.1.1]pentan-1-yl)-2-naphthamide,
(S)-5,6-dichloro-N-(3-(1-((4-fluorophenyl)amino)-1-oxopropan-2-yl)bicyclo[1.1.1]pentan-1-yl)picolinamide,
(S)—N-(3-(1-((4-fluorophenyl)amino)-1-oxopropan-2-yl)bicyclo[1.1.1]pentan-1-yl)-6-(trifluoromethyl)picolinamide,
(S)-3-chloro-4-cyano-N-(3-(1-((4-fluorophenyl)amino)-1-oxopropan-2-yl)bicyclo[1.1.1]pentan-1-yl)benzamide,
(S)-4-cyano-N-(3-(1-((4-fluorophenyl)amino)-1-oxopropan-2-yl)bicyclo[1.1.1]pentan-1-yl)-3-methylbenzamide,
(S)—N-(3-(1-((4-fluorophenyl)amino)-1-oxopropan-2-yl)bicyclo[1.1.1]pentan-1-yl)quinoline-7-carboxamide,
(S)—N-(3-(1-((4-fluorophenyl)amino)-1-oxopropan-2-yl)bicyclo[1.1.1]pentan-1-yl)-6-(trifluoromethyl)nicotinamide,
cyclopentyl (S)-(3-(1-((4-fluorophenyl)amino)-1-oxopropan-2-yl)bicyclo[1.1.1]pentan-1-yl)carbamate,
benzyl (S)-(3-(1-((4-fluorophenyl)amino)-1-oxopropan-2-yl)bicyclo[1.1.1]pentan-1-yl)carbamate,
isopropyl (S)-(3-(1-((4-fluorophenyl)amino)-1-oxopropan-2-yl)bicyclo[1.1.1]pentan-1-yl)carbamate,
cyclopropyl (S)-(3-(1-((4-fluorophenyl)amino)-1-oxopropan-2-yl)bicyclo[1.1.1]pentan-1-yl)carbamate,
(S)-2-(3-(3-(3-chlorophenyl)ureido)bicyclo[1.1.1]pentan-1-yl)-N-(4-fluorophenyl)propanamide,
(S)-2-(3-(3-(3,4-difluorophenyl)ureido)bicyclo[1.1.1]pentan-1-yl)-N-(4-fluorophenyl)propanamide,
(S)-2-(3-(3-(3-chloro-4-fluorophenyl)ureido)bicyclo[1.1.1]pentan-1-yl)-N-(4-fluorophenyl)propanamide,
(S)-2-(3-(3-(3-chloro-2-methylphenyl)ureido)bicyclo[1.1.1]pentan-1-yl)-N-(4-fluorophenyl)propanamide,
(S)—N-(4-fluorophenyl)-2-(3-(3-(4-fluorophenyl)ureido)bicyclo[1.1.1]pentan-1-yl)propanamide,
(S)—N-(4-fluorophenyl)-2-(3-(3-(naphthalen-1-yl)ureido)bicyclo[1.1.1]pentan-1-yl)propanamide,
(S)—N-(4-fluorophenyl)-2-(3-(3-(3-(trifluoromethyl)phenyl)ureido)bicyclo[1.1.1]pentan-1-yl)propanamide,
(R)-3,4-dichloro-N-(3-(1-((5,6-difluoropyridin-3-yl)amino)-1-oxopropan-2-yl) bicyclo[1.1.1]pentan-1-yl)benzamide, (R)-3,4-dichloro-N-(3-(1-((6-chloro-5-fluoropyridin-3-yl)amino)-1-oxopropan-2-yl)bicyclo[1.1.1]pentan-1-yl)benzamide,
(R)-3,4-dichloro-N-(3-(1-((2-chloropyrimidin-5-yl)amino)-1-oxopropan-2-yl)bicyclo[1.1.1]pentan-1-yl)benzamide,
(R)-3,4-dichloro-N-(3-(1-((3,4-difluorophenyl)amino)-1-oxopropan-2-yl)bicyclo[1.1.1]pentan-1-yl)benzamide,
(R)-3,4-dichloro-N-(3-(1-oxo-1-((4-(trifluoromethyl)phenyl)amino)propan-2-yl)bicyclo[1.1.1]pentan-1-yl)benzamide,
(S)-3,4-dichloro-N-(3-(1-((5,6-dichloropyridin-3-yl)amino)-1-oxopropan-2-yl)bicyclo[1.1.1]pentan-1-yl)benzamide,
(S)-3-chloro-5-(2-(3-(3,4-dichlorobenzamido)bicyclo[1.1.1]pentan-1-yl)propanamido)pyridin-1-ium,
(S)-3,4-dichloro-N-(3-(1-((4-fluoro-3-(trifluoromethyl)phenyl)amino)-1-oxopropan-2-yl)bicyclo[1.1.1]pentan-1-yl)benzamide,
(S)-3,4-dichloro-N-(3-(1-((3-chloro-4-fluorophenyl)amino)-1-oxopropan-2-yl)bicyclo[1.1.1]pentan-1-yl)benzamide,
(S)-3,4-dichloro-N-(3-(1-((3,4-difluorophenyl)amino)-1-oxopropan-2-yl)bicyclo[1.1.1]pentan-1-yl)benzamide,
(S)-3,4-dichloro-N-(3-(1-oxo-1-((4-(trifluoromethyl)phenyl)amino)propan-2-yl)bicyclo[1.1.1]pentan-1-yl)benzamide,
(S)-3,4-dichloro-N-(3-(1-oxo-1-((3-(trifluoromethyl)phenyl)amino)propan-2-yl)bicyclo[1.1.1]pentan-1-yl)benzamide,
3,4-dichloro-N-(3-(1-((4-fluorophenyl)carbamoyl)cyclopropyl)bicyclo[1.1.1]pentan-1-yl)benzamide,
3,4-dichloro-N-(3-(1-((4-fluorophenyl)amino)-2-methyl-1-oxopropan-2-yl)bicyclo[1.1.1]pentan-1-yl)benzamide,
3-chloro-N-(3-(1-((4-fluorophenyl)amino)-2-methyl-1-oxopropan-2-yl)bicyclo[1.1.1]pentan-1-yl)benzamide,
3,4-dichloro-N-(3-(2-(4-fluorobenzamido)propan-2-yl)bicyclo[1.1.1]pentan-1-yl)benzamide,
3-(3-(3-chlorobenzamido)bicyclo[1.1.1]pentan-1-yl)-N-(4-fluorophenyl)oxetane-3-carboxamide,
3-(3-(3-chlorobenzamido)bicyclo[1.1.1]pentan-1-yl)-N-(3,4-difluorophenyl)oxetane-3-carboxamide,
3-(3-(3,4-difluorobenzamido)bicyclo[1.1.1]pentan-1-yl)-N-(4-fluorophenyl)oxetane-3-carboxamide,
3-(3-(3,4-difluorobenzamido)bicyclo[1.1.1]pentan-1-yl)-N-(3,4-difluorophenyl)oxetane-3-carboxamide,
N-(4-chlorophenyl)-3-(3-(3,4-difluorobenzamido)bicyclo[1.1.1]pentan-1-yl)oxetane-3-carboxamide,
N-[3-[2-(4-fluoroanilino)-1-methyl-2-oxo-ethyl]-1-bicyclo[1.1.1]pentanyl]-3-(trifluoromethoxy)benzamide,
5-ethyl-N-[3-[2-(4-fluoroanilino)-1-methyl-2-oxo-ethyl]-1-bicyclo[1.1.1]pentanyl]isoxazole-3-carboxamide,
N-[3-[2-(4-fluoroanilino)-1-methyl-2-oxo-ethyl]-1-bicyclo[1.1.1]pentanyl]imidazo[1,5-a]pyridin-2-ium-5-carboxamide,
4-chloro-N-[3-[2-(4-fluoroanilino)-1-methyl-2-oxo-ethyl]-1-bicyclo[1.1.1]pentanyl]pyridin-1-ium-2-carboxamide,
N-[3-[2-(4-fluoroanilino)-1-methyl-2-oxo-ethyl]-1-bicyclo[1.1.1]pentanyl]pyrazolo[1,5-a]pyridin-1-ium-3-carboxamide,
N-[3-[2-(4-fluoroanilino)-1-methyl-2-oxo-ethyl]-1-bicyclo[1.1.1]pentanyl]-3-methyl-1,2,4-oxadiazole-5-carboxamide,
N-[3-[2-(4-fluoroanilino)-1-methyl-2-oxo-ethyl]-1-bicyclo[1.1.1]pentanyl]-4,5,6,7-tetrahydro-1,2-benzoxazole-3-carboxamide,
N-[3-[2-(4-fluoroanilino)-1-methyl-2-oxo-ethyl]-1-bicyclo[1.1.1]pentanyl]indolizine-2-carboxamide,
4-ethyl-N-[3-[2-(4-fluoroanilino)-1-methyl-2-oxo-ethyl]-1-bicyclo[1.1.1]pentanyl]pyridin-1-ium-2-carboxamide,
N-[3-[2-(4-fluoroanilino)-1-methyl-2-oxo-ethyl]-1-bicyclo[1.1.1]pentanyl]-4-methyl-pyridin-1-ium-2-carboxamide,
N-[3-[2-(4-fluoroanilino)-1-methyl-2-oxo-ethyl]-1-bicyclo[1.1.1]pentanyl]-6-methyl-pyridin-1-ium-2-carboxamide,
5-cyclopropyl-N-[3-[2-(4-fluoroanilino)-1-methyl-2-oxo-ethyl]-1-bicyclo[1.1.1]pentanyl]isoxazole-3-carboxamide,
N-[3-[2-(4-fluoroanilino)-1-methyl-2-oxo-ethyl]-1-bicyclo[1.1.1]pentanyl]-2-oxo-indoline-4-carboxamide,
N-[3-[2-(4-fluoroanilino)-1-methyl-2-oxo-ethyl]-1-bicyclo[1.1.1]pentanyl]-5-methyl-pyridin-1-ium-3-carboxamide,
N-[3-[2-(4-fluoroanilino)-1-methyl-2-oxo-ethyl]-1-bicyclo[1.1.1]pentanyl]-2-methyl-thiazole-4-carboxamide,
N-[3-[2-(4-fluoroanilino)-1-methyl-2-oxo-ethyl]-1-bicyclo[1.1.1]pentanyl]-5-methyl-pyrazolo[1,5-a]pyridin-1-ium-3-carboxamide,
N-[3-[2-(4-fluoroanilino)-1-methyl-2-oxo-ethyl]-1-bicyclo[1.1.1]pentanyl]-2-methoxy-pyridin-1-ium-4-carboxamide,
N-[3-[2-(4-fluoroanilino)-1-methyl-2-oxo-ethyl]-1-bicyclo[1.1.1]pentanyl]pyrazolo[1,5-a]pyridin-1-ium-7-carboxamide,
N-[3-[2-(4-fluoroanilino)-1-methyl-2-oxo-ethyl]-1-bicyclo[1.1.1]pentanyl]indolizine-1-carboxamide,
N-(4-fluorophenyl)-2-[3-[[2-[2-(trifluoromethyl)phenyl]acetyl]amino]-1-bicyclo[1.1.1]pentanyl]propanamide,
N-[3-[2-(4-fluoroanilino)-1-methyl-2-oxo-ethyl]-1-bicyclo[1.1.1]pentanyl]pyridin-1-ium-2-carboxamide,
N-[3-[2-(4-fluoroanilino)-1-methyl-2-oxo-ethyl]-1-bicyclo[1.1.1]pentanyl]isoquinolin-2-ium-8-carboxamide,
1-(difluoromethyl)-N-[3-[2-(4-fluoroanilino)-1-methyl-2-oxo-ethyl]-1-bicyclo[1.1.1]pentanyl]pyrazole-3-carboxamide,
N-[3-[2-(4-fluoroanilino)-1-methyl-2-oxo-ethyl]-1-bicyclo[1.1.1]pentanyl]-6-methyl-pyridin-1-ium-3-carboxamide,
N-[3-[2-(4-fluoroanilino)-1-methyl-2-oxo-ethyl]-1-bicyclo[1.1.1]pentanyl]-5-(trifluoromethyl)pyridin-1-ium-2-carboxamide,
N-[3-[2-(4-fluoroanilino)-1-methyl-2-oxo-ethyl]-1-bicyclo[1.1.1]pentanyl]isoquinolin-2-ium-5-carboxamide,
N-[3-[2-(4-fluoroanilino)-1-methyl-2-oxo-ethyl]-1-bicyclo[1.1.1]pentanyl]cinnoline-4-carboxamide,
N-[3-[2-(4-fluoroanilino)-1-methyl-2-oxo-ethyl]-1-bicyclo[1.1.1]pentanyl]-2,4-dimethyl-thiazole-5-carboxamide,
3-fluoro-N-[3-[2-(4-fluoroanilino)-1-methyl-2-oxo-ethyl]-1-bicyclo[1.1.1]pentanyl]pyridin-1-ium-2-carboxamide,
6-ethoxy-N-[3-[2-(4-fluoroanilino)-1-methyl-2-oxo-ethyl]-1-bicyclo[1.1.1]pentanyl]pyridin-1-ium-2-carboxamide,
N-[3-[2-(4-fluoroanilino)-1-methyl-2-oxo-ethyl]-1-bicyclo[1.1.1]pentanyl]-2,5-dimethyl-pyrazole-3-carboxamide, 5-chloro-N-[3-[2-(4-fluoroanilino)-1-methyl-2-oxo-ethyl]-1-bicyclo[1.1.1]pentanyl]pyrazine-2-carboxamide, 5-ethyl-N-[3-[2-(4-fluoroanilino)-1-methyl-2-oxo-ethyl]-1-bicyclo[1.1.1]pentanyl]-2-methyl-pyrazole-3-carboxamide, N-[3-[2-(4-fluoroanilino)-1-methyl-2-oxo-ethyl]-1-bicyclo[1.1.1]pentanyl]pyridin-1-ium-3-carboxamide, N-[3-[2-(4-fluoroanilino)-1-methyl-2-oxo-ethyl]-1-bicyclo[1.1.1]pentanyl]triazolo[1,5-a]pyridin-1-ium-4-carboxamide, N-[3-[2-(4-fluoroanilino)-1-methyl-2-oxo-ethyl]-1-bicyclo[1.1.1]pentanyl]isoquinolin-2-ium-3-carboxamide, (S)-3,4,5-trifluoro-N-(3-(1-((4-fluorophenyl)amino)-1-oxopropan-2-yl)bicyclo[1.1.1]pentan-1-yl)benzamide, (S)—N-(3-(1-((4-fluorophenyl)amino)-1-oxopropan-2-yl)bicyclo[1.1.1]pentan-1-yl)-6-(trifluoromethyl)nicotinamide, (S)—N-(3-(1-((4-fluorophenyl)amino)-1-oxopropan-2-yl)bicyclo[1.1.1]pentan-1-yl)quinoline-7-carboxamide, (S)—N-(3-(1-((4-fluorophenyl)amino)-1-oxopropan-2-yl)bicyclo[1.1.1]pentan-1-yl)-2-naphthamide, (S)-5,6-dichloro-N-(3-(1-((4-fluorophenyl)amino)-1-oxopropan-2-yl)bicyclo[1.1.1]pentan-1-yl)picolinamide, (S)-3-chloro-4-cyano-N-(3-(1-((4-fluorophenyl)amino)-1-oxopropan-2-yl)bicyclo[1.1.1]pentan-1-yl)benzamide, (S)-4-cyano-N-(3-(1-((4-fluorophenyl)amino)-1-oxopropan-2-yl)bicyclo[1.1.1]pentan-1-yl)-3-methylbenzamide, (S)—N-(3-(1-((4-fluorophenyl)amino)-1-oxopropan-2-yl)bicyclo[1.1.1]pentan-1-yl)-6-(trifluoromethyl)picolinamide, (S)-3,5-difluoro-N-(3-(1-((4-fluorophenyl)amino)-1-oxopropan-2-yl)bicyclo[1.1.1]pentan-1-yl)benzamide, and (S)-2,4,5-trifluoro-N-(3-(1-((4-fluorophenyl)amino)-1-oxopropan-2-yl)bicyclo[1.1.1]pentan-1-yl)benzamide;

or a pharmaceutically acceptable salt thereof.

15. A composition which comprises an inert carrier and a compound of claim 1 or a pharmaceutically acceptable salt thereof.

16. A method for treating or preventing an IDO-associated disease or disorder in a mammalian subject which comprises administering to the subject an effective amount of a compound of claim 1 or a pharmaceutically acceptable salt thereof.

17. A method for treating an IDO-associated disease or disorder in a mammalian subject which comprises administering to the subject an effective amount of a compound of claim 1 or a pharmaceutically acceptable salt thereof in combination with another anti-cancer agent.

18. The method of claim 16, wherein the IDO-associated disease or disorder is a cancer, viral infection, HCV infection, depression, neurodegenerative disorders, trauma, age-related cataracts, organ transplantation, and autoimmune diseases.

19. The method of claim 18, wherein the cancer is selected from colon cancer, pancreas cancer, breast cancer, prostate cancer, lung cancer, brain cancer, ovarian cancer, cervical cancer, testes cancer, renal cancer, head and neck cancer, lymphoma, leukemia and melanoma.

* * * * *